US006949633B1

(12) United States Patent
Monforte et al.

(10) Patent No.: US 6,949,633 B1
(45) Date of Patent: Sep. 27, 2005

(54) PRIMERS USEFUL FOR SIZING NUCLEIC ACIDS

(75) Inventors: Joseph Albert Monforte, Berkeley, CA (US); Christopher Hank Becker, Palo Alto, CA (US); Thomas Andrew Shaler, Menlo Park, CA (US); Daniel Joseph Pollart, Alameda, CA (US)

(73) Assignee: Sequenom, Inc., San Diego, CA (US)

( * ) Notice: Subject to any disclaimer, the term of this patent is extended or adjusted under 35 U.S.C. 154(b) by 0 days.

(21) Appl. No.: 09/139,386

(22) Filed: Aug. 25, 1998

Related U.S. Application Data

(63) Continuation-in-part of application No. 08/639,363, filed on Apr. 26, 1996, now Pat. No. 5,830,655, which is a continuation-in-part of application No. 08/445,751, filed on May 22, 1995, now Pat. No. 5,700,642.

(51) Int. Cl.$^7$ .................. C07H 19/00; C07H 21/00; C07H 21/04
(52) U.S. Cl. .................. 536/22.1; 536/23.1; 536/24.33; 536/25.32
(58) Field of Search .............................. 536/22.1, 23.1, 536/24.33, 25.32

(56) References Cited

U.S. PATENT DOCUMENTS

| | | | |
|---|---|---|---|
| 4,139,346 A | 2/1979 | Rabbani | 422/56 |
| 4,515,781 A | 5/1985 | Torrence et al. | 514/44 |
| 4,582,789 A | 4/1986 | Sheldon, III et al. | 435/6 |
| 4,604,363 A | 8/1986 | Newhouse et al. | 436/177 |
| 4,656,127 A | 4/1987 | Mundy | 435/6 |
| 4,683,194 A | 7/1987 | Saiki et al. | 435/6 |
| 4,683,195 A | 7/1987 | Mullis et al. | 435/6 |
| 4,683,202 A | 7/1987 | Mullis | 435/91 |
| 4,711,955 A | 12/1987 | Ward et al. | 536/25.32 |
| 4,725,677 A | 2/1988 | Köster et al. | 536/27 |
| 4,729,947 A | 3/1988 | Middendorf et al. | 435/6 |
| 4,775,619 A | 10/1988 | Urdea | 435/6 |
| 4,806,546 A | 2/1989 | Carrico et al. | 536/27 |
| 4,818,681 A | 4/1989 | Dattagupta | 435/6 |
| 4,882,127 A | 11/1989 | Rosenthal et al. | 422/50 |
| 4,920,264 A | 4/1990 | Becker | 250/282 |
| 4,998,617 A | 3/1991 | Ladd, Jr. et al. | 206/219 |
| 5,003,059 A | 3/1991 | Brennan | 536/27 |
| 5,059,654 A | 10/1991 | Hou et al. | 525/54.1 |
| 5,062,935 A | 11/1991 | Schlag et al. | 204/157.41 |
| 5,064,754 A | 11/1991 | Mills | 435/6 |
| 5,106,585 A | 4/1992 | Minami et al. | |
| 5,118,605 A | 6/1992 | Urdea | 435/6 |
| 5,118,937 A | 6/1992 | Hillenkamp et al. | 250/282 |
| 5,135,870 A | 8/1992 | Williams et al. | 436/173 |
| 5,143,854 A | 9/1992 | Pirrung et al. | 436/518 |
| 5,149,625 A | 9/1992 | Church et al. | 435/6 |
| 5,175,209 A | 12/1992 | Beattie et al. | 525/54.11 |
| 5,198,540 A | 3/1993 | Köster | 536/25.3 |
| 5,210,412 A | 5/1993 | Levis et al. | 250/288 |
| 5,221,518 A | 6/1993 | Mills | 422/62 |
| 5,237,016 A | 8/1993 | Ghosh et al. | 525/329.4 |
| 5,242,974 A | 9/1993 | Holmes | 525/54.11 |
| 5,288,644 A | 2/1994 | Beavis et al. | 436/94 |
| 5,300,774 A | 4/1994 | Buttrill | 250/287 |
| 5,306,619 A * | 4/1994 | Edwards et al. | 435/6 |
| 5,338,688 A | 8/1994 | Deeg et al. | 436/180 |
| 5,350,676 A | 9/1994 | Oberhardt et al. | 435/13 |
| 5,364,760 A | 11/1994 | Chu et al. | 435/6 |
| 5,376,788 A | 12/1994 | Standing et al. | 250/287 |
| 5,380,833 A | 1/1995 | Urdea | 536/22.1 |
| 5,403,711 A | 4/1995 | Walder et al. | 435/6 |
| 5,405,746 A | 4/1995 | Uhlen | 435/6 |
| 5,427,929 A * | 6/1995 | Richards et al. | 435/91.2 |
| 5,430,136 A | 7/1995 | Urdea et al. | 536/243 |
| 5,436,143 A | 7/1995 | Hyman | 435/91.2 |
| 5,459,039 A | 10/1995 | Modrich et al. | 435/6 |
| 5,484,701 A | 1/1996 | Cocuzza et al. | 435/6 |
| 5,492,806 A | 2/1996 | Drmanac et al. | 435/5 |
| 5,498,545 A | 3/1996 | Vestal | 436/47 |
| 5,503,980 A | 4/1996 | Cantor | 435/6 |
| 5,506,348 A | 4/1996 | Pieles | 536/23.1 |
| 5,508,169 A | 4/1996 | Deugau et al. | 435/6 |
| 5,512,295 A | 4/1996 | Kornberg et al. | 424/450 |
| 5,512,439 A | 4/1996 | Hornes et al. | 435/6 |
| 5,514,548 A | 5/1996 | Krebber et al. | 435/6 |
| 5,525,464 A | 6/1996 | Drmanac et al. | 435/6 |
| 5,527,675 A | 6/1996 | Coull et al. | 435/6 |

(Continued)

FOREIGN PATENT DOCUMENTS

| | | |
|---|---|---|
| DE | 3930312 | 4/1990 |
| DE | 4011991 | 10/1990 |
| DE | 19617011 | 4/1996 |

(Continued)

OTHER PUBLICATIONS

"Time of Flight Mass Spectrometry of DNA for Rapid Sequence Determination. Technical Progress Report, Jul. 31, 1991 –Jul. 31, 1992", Arizona State University, Tempe, AZ (1992).

Adler et al., "Cell Membrane Coating with Glutaraldehyde: Application to a Versatile Solid–Phase Assay for Thyroid Membrane Proteins and Molecules Interecting with Thyroid Membranes", *Anal. Biochem.*, 148:320–327 (1985).

Ali, S. and Wallace, R. B., "Intrinsic polymorphism of variable number tandem repeat loci in the human genome", *Nucl. Acids Res.*, 16:8487–8496 (1988).

(Continued)

*Primary Examiner*—Kenneth R. Horlick
*Assistant Examiner*—Joyce Tung
(74) *Attorney, Agent, or Firm*—Bruce D. Grant; BioTechnology Law Group

(57) ABSTRACT

The present invention provides modified oligonucleotide primers designed to incorporate a cleavable moiety so that a 3' portion of the primer (linked to an extension product) can be released from an upstream 5' portion of the primer. Upon selective cleavage of the cleavable site, primer extension products that contain about five or fewer base pairs of the primer sequence are released, to provide more useful sizing and sequence information per fragment than extension products containing the entire primer.

22 Claims, 25 Drawing Sheets

U.S. PATENT DOCUMENTS

| | | | | |
|---|---|---|---|---|
| 5,538,897 A | | 7/1996 | Yates et al. ................... | 436/89 |
| 5,547,835 A | | 8/1996 | Köster .......................... | 435/6 |
| 5,571,669 A | | 11/1996 | Lu et al. ....................... | 435/6 |
| 5,571,676 A | | 11/1996 | Shuber ......................... | 435/6 |
| 5,580,434 A | | 12/1996 | Robotti et al. ............... | 422/102 |
| 5,580,732 A | | 12/1996 | Grossman et al. ............ | 435/6 |
| 5,580,733 A | | 12/1996 | Levis et al. ................... | 435/6 |
| 5,589,136 A | | 12/1996 | Northrup et al. ............. | 422/102 |
| 5,593,826 A | | 1/1997 | Fung et al. .................... | 435/6 |
| 5,601,982 A | | 2/1997 | Sargent et al. ................ | 435/6 |
| 5,605,662 A | | 2/1997 | Heller ........................... | 422/68.1 |
| 5,605,798 A | | 2/1997 | Köster .......................... | 435/6 |
| 5,609,907 A | | 3/1997 | Natan .......................... | 427/2.12 |
| 5,622,824 A | * | 4/1997 | Koster .......................... | 435/6 |
| 5,622,829 A | | 4/1997 | King et al. .................... | 435/6 |
| 5,631,134 A | | 5/1997 | Cantor .......................... | 435/6 |
| 5,641,862 A | | 6/1997 | Rutter et al. .................. | 530/334 |
| 5,643,800 A | | 7/1997 | Tarantino et al. ............. | 436/518 |
| 5,650,489 A | | 7/1997 | Lam et al. ..................... | 530/334 |
| 5,654,150 A | | 8/1997 | King et al. .................... | 435/6 |
| 5,663,242 A | | 9/1997 | Ghosh et al. .................. | 525/329.4 |
| 5,670,322 A | | 9/1997 | Eggers et al. .................. | 435/6 |
| 5,670,381 A | | 9/1997 | Jou et al. ....................... | 436/518 |
| 5,677,195 A | | 10/1997 | Winkler et al. ................ | 436/518 |
| 5,688,642 A | | 11/1997 | Chrisey et al. ................ | 435/6 |
| 5,691,141 A | | 11/1997 | Köster et al. .................. | 435/6 |
| 5,695,940 A | | 12/1997 | Drmanac et al. .............. | 435/6 |
| 5,700,642 A | | 12/1997 | Monforte et al. .............. | 435/6 |
| 5,710,028 A | | 1/1998 | Eyal et al. ..................... | 435/91.1 |
| 5,716,825 A | | 2/1998 | Hancock et al. .............. | 435/286.5 |
| 5,760,393 A | | 6/1998 | Vestal et al. ................... | 250/282 |
| 5,762,876 A | | 6/1998 | Lincoln et al. ................ | 422/67 |
| 5,763,594 A | * | 6/1998 | Hiatt et al. .................... | 536/25.3 |
| 5,770,367 A | | 6/1998 | Southern et al. .............. | 435/6 |
| 5,770,860 A | | 6/1998 | Franzen ........................ | 250/288 |
| 5,777,324 A | | 7/1998 | Hillenkamp .................. | 250/288 |
| 5,795,714 A | | 8/1998 | Cantor et al. .................. | 435/6 |
| 5,807,522 A | | 9/1998 | Brown et al. .................. | 422/50 |
| 5,821,063 A | | 10/1998 | Patterson et al. .............. | 435/6 |
| 5,828,063 A | | 10/1998 | Köster et al. .................. | 250/288 |
| 5,830,655 A | | 11/1998 | Monforte et al. .............. | 435/6 |
| 5,834,189 A | | 11/1998 | Stevens et al. ................ | 435/6 |
| 5,846,710 A | | 12/1998 | Bajaj ............................. | 435/6 |
| 5,846,717 A | | 12/1998 | Brow et al. .................... | 435/6 |
| 5,851,765 A | | 12/1998 | Köster .......................... | 435/6 |
| 5,853,989 A | | 12/1998 | Jeffreys et al. ................. | 435/6 |
| 5,854,486 A | | 12/1998 | Dreyfus ........................ | 250/288 |
| 5,856,092 A | | 1/1999 | Dale et al. ..................... | 435/6 |
| 5,864,137 A | | 1/1999 | Becker et al. ................. | 250/287 |
| 5,869,240 A | | 2/1999 | Patterson ...................... | 435/6 |
| 5,869,242 A | | 2/1999 | Kamb ........................... | 435/6 |
| 5,872,003 A | | 2/1999 | Köster .......................... | 435/283.1 |
| 5,876,934 A | | 3/1999 | Duthie et al. .................. | 435/6 |
| 5,885,775 A | | 3/1999 | Haff et al. ..................... | 435/6 |
| 5,888,819 A | | 3/1999 | Goelet et al. .................. | 435/5 |
| 5,894,063 A | | 4/1999 | Hutchens et al. .............. | 436/155 |
| 5,900,481 A | | 5/1999 | Lough et al. .................. | 536/55.3 |
| 5,908,755 A | | 6/1999 | Kumar et al. .................. | 435/6 |
| 5,912,118 A | | 6/1999 | Ansorge et al. ............... | 435/6 |
| 5,925,520 A | | 7/1999 | Tully et al. .................... | 435/6 |
| 5,928,906 A | | 7/1999 | Köster et al. .................. | 435/91.2 |
| 5,948,653 A | | 9/1999 | Pati et al. ...................... | 435/6 |
| 5,952,174 A | | 9/1999 | Nikiforov et al. ............. | 435/6 |
| 5,965,363 A | | 10/1999 | Monforte et al. .............. | 435/6 |
| 5,969,350 A | | 10/1999 | Kerley et al. .................. | 250/287 |
| 5,976,798 A | | 11/1999 | Parker et al. .................. | 435/6 |
| 5,976,802 A | | 11/1999 | Ansorge et al. ............... | 435/6 |
| 5,981,186 A | | 11/1999 | Gabe et al. .................... | 435/6 |
| 5,985,356 A | | 11/1999 | Schultz et al. ................. | 427/8 |
| 5,998,143 A | | 12/1999 | Ellis et al. ..................... | 435/6 |
| 6,001,567 A | | 12/1999 | Brow et al. .................... | 435/6 |
| 6,004,744 A | | 12/1999 | Goelet et al. .................. | 435/5 |
| 6,013,431 A | | 1/2000 | Söderlund et al. ............. | 435/5 |
| 6,017,702 A | | 1/2000 | Lee et al. ....................... | 435/6 |
| 6,018,041 A | | 1/2000 | Drmanac et al. .............. | 536/24.3 |
| 6,022,688 A | | 2/2000 | Jurinke et al. ................. | 435/6 |
| 6,024,925 A | | 2/2000 | Little et al. .................... | 422/100 |
| 6,025,136 A | | 2/2000 | Drmanac ....................... | 435/6 |
| 6,027,890 A | | 2/2000 | Ness et al. ..................... | 435/6 |
| 6,030,778 A | | 2/2000 | Acton et al. ................... | 435/6 |
| 6,040,193 A | | 3/2000 | Winkler et al. ................ | 436/180 |
| 6,043,031 A | | 3/2000 | Köster et al. .................. | 435/6 |
| 6,046,005 A | | 4/2000 | Ju et al. ......................... | 435/6 |
| 6,051,378 A | | 4/2000 | Monforte et al. .............. | 435/6 |
| 6,054,276 A | | 4/2000 | Macevicz ...................... | 435/6 |
| 6,074,823 A | | 6/2000 | Köster .......................... | 435/6 |
| 6,074,853 A | | 6/2000 | Pati et al. ...................... | 435/91.1 |
| 6,087,095 A | | 7/2000 | Rosenthal et al. ............. | 435/6 |
| 6,090,558 A | | 7/2000 | Butler et al. ................... | 435/6 |
| 6,104,028 A | | 8/2000 | Hunter et al. .................. | 250/288 |
| 6,110,426 A | | 8/2000 | Shalon et al. .................. | 422/68.1 |
| 6,111,251 A | | 8/2000 | Hillenkamp ................... | 250/288 |
| 6,117,634 A | | 9/2000 | Langmore et al. ............. | 435/6 |
| 6,121,048 A | | 9/2000 | Zaffaroni et al. .............. | 436/45 |
| 6,132,724 A | | 10/2000 | Blum ............................ | 424/725 |
| 6,133,436 A | | 10/2000 | Köster et al. .................. | 536/24.3 |
| 6,136,269 A | | 10/2000 | Winkler et al. ................ | 422/61 |
| 6,140,045 A | | 10/2000 | Wohlstadter et al. .......... | 435/6 |
| 6,140,053 A | | 10/2000 | Köster .......................... | 435/6 |
| 6,146,854 A | | 11/2000 | Köster et al. .................. | 435/91.1 |
| 6,156,501 A | | 12/2000 | McGall et al. ................. | 435/6 |
| 6,194,144 B1 | | 2/2001 | Köster .......................... | 435/6 |
| 6,197,498 B1 | | 3/2001 | Köster .......................... | 435/5 |
| 6,200,812 B1 | | 3/2001 | Pati et al. ...................... | 435/463 |
| 6,207,370 B1 | | 3/2001 | Little et al. .................... | 435/6 |
| 6,221,601 B1 | | 4/2001 | Köster et al. .................. | 435/6 |
| 6,221,605 B1 | | 4/2001 | Köster .......................... | 435/6 |
| 6,225,061 B1 | | 5/2001 | Becker et al. ................. | 435/6 |
| 6,225,450 B1 | | 5/2001 | Köster .......................... | 536/22.1 |
| 6,235,478 B1 | | 5/2001 | Köster .......................... | 435/6 |
| 6,238,871 B1 | | 5/2001 | Köster .......................... | 435/6 |
| 6,258,538 B1 | | 7/2001 | Köster et al. .................. | 435/6 |
| 6,265,716 B1 | | 7/2001 | Hunter et al. .................. | 250/288 |
| 6,268,131 B1 | | 7/2001 | Kang et al. .................... | 435/6 |
| 6,277,573 B1 | | 8/2001 | Köster .......................... | 435/6 |
| 6,300,076 B1 | | 10/2001 | Köster .......................... | 435/6 |
| 6,303,309 B1 | | 10/2001 | Jurinke et al. ................. | 435/6 |
| 6,322,970 B1 | | 11/2001 | Little et al. .................... | 435/6 |

FOREIGN PATENT DOCUMENTS

| | | | |
|---|---|---|---|
| DE | 4438630 A1 | 5/1996 | |
| DE | 19628178 | 7/1996 | |
| DE | 19618032 | 11/1997 | |
| DE | 19754978 | 12/1997 | |
| DE | 4431174 A1 | 3/1998 | |
| DE | 19731479 | 8/1998 | |
| EP | 0227772 | 6/1986 | ............ C12Q/1/68 |
| EP | 0269520 A2 | 7/1988 | |
| EP | 0360676 | 9/1989 | ............ C12Q/1/68 |
| EP | 0360676 A1 | 3/1990 | |
| EP | 0360677 B1 | 3/1990 | |
| EP | 0412883 A1 | 2/1991 | |
| EP | 0593789 A1 | 4/1994 | |
| EP | 0655501 A1 | 5/1995 | |
| EP | 0683234 | 11/1995 | |
| EP | 0701001 A2 | 3/1996 | |
| EP | 0771019 | 5/1997 | |
| EP | 0785278 | 7/1997 | |
| EP | 0648280 B1 | 5/1999 | |
| EP | 0828855 | 12/1999 | |
| GB | 2017105 | 3/1979 | |

| | | | | | | | | |
|---|---|---|---|---|---|---|---|---|
| GB | 2233654 | 1/1991 | | | WO | 9803257 | 1/1998 | |
| GB | 2260811 | 4/1993 | | | WO | 9811249 | 3/1998 | |
| GB | 2312782 | 11/1997 | | | WO | 9812355 | 3/1998 | |
| GB | 2332273 | 6/1999 | | | WO | 9812734 | 3/1998 | |
| JP | 63230086 A | 9/1988 | | | WO | 9814982 | 4/1998 | |
| JP | 2215399 | 8/1990 | | | WO | 9820019 | 5/1998 | |
| JP | 4178359 | 6/1992 | | | WO | 9820020 | 5/1998 | |
| JP | 6294796 A | 10/1994 | | | WO | 9820166 | 5/1998 | |
| WO | 8502907 | 7/1985 | | | WO | 9823284 | 6/1998 | |
| WO | 8504674 | 10/1985 | | | WO | 9824935 | 6/1998 | |
| WO | 8800201 | 1/1988 | | | WO | 9826095 | 6/1998 | |
| WO | 8810315 | 12/1988 | | | WO | 9830883 | 7/1998 | |
| WO | 8903432 A1 | 4/1989 | ............ | C12Q/1/68 | WO | 9833052 | 7/1998 | |
| WO | 8906700 A1 | 7/1989 | | | WO | 9833808 | 8/1998 | |
| WO | 8907149 | 8/1989 | | | WO | 9835609 | 8/1998 | |
| WO | 8909282 | 10/1989 | | | WO | 9819578 | 9/1998 | |
| WO | 8912624 | 12/1989 | | | WO | 9854571 | 12/1998 | |
| WO | 8912694 | 12/1989 | | | WO | 9854751 | 12/1998 | |
| WO | WO 89/12694 | 12/1989 | ............ | C12Q/1/68 | WO | 9856954 | 12/1998 | |
| WO | 9001564 | 2/1990 | | | WO | 9905323 | 2/1999 | |
| WO | 9003382 | 4/1990 | | | WO | 9909218 | 2/1999 | |
| WO | 9007582 | 7/1990 | | | WO | 9912040 | 3/1999 | .......... G01N/33/68 |
| WO | 9014148 | 11/1990 | | | WO | 9914375 | 3/1999 | |
| WO | 9015883 | 12/1990 | | | WO | 9931278 | 6/1999 | |
| WO | 9111533 | 1/1991 | | | WO | 9957318 | 11/1999 | |
| WO | 9102087 | 2/1991 | | | WO | 0051053 | 8/2000 | |
| WO | 9106678 | 5/1991 | | | WO | 0056446 | 9/2000 | |
| WO | 9113075 | 9/1991 | | | WO | 0058519 | 10/2000 | |
| WO | 9115600 | 10/1991 | | | WO | 0060361 | 10/2000 | |
| WO | 9203575 | 3/1992 | | | | | | |
| WO | WO 92/05287 | 4/1992 | ............ | C12Q/1/68 | | | | |
| WO | 9213629 | 8/1992 | | | | | | |
| WO | 9215712 | 9/1992 | | | | | | |
| WO | 9306925 | 4/1993 | | | | | | |
| WO | 9309668 | 5/1993 | | | | | | |
| WO | 9320236 | 10/1993 | | | | | | |
| WO | 9323563 A1 | 10/1993 | | | | | | |
| WO | 9324834 | 12/1993 | | | | | | |
| WO | 9400562 | 1/1994 | | | | | | |
| WO | 9411530 | 5/1994 | | | | | | |
| WO | 9416101 | 7/1994 | | | | | | |
| WO | 9421822 | 9/1994 | | | | | | |
| WO | 9428418 | 12/1994 | | | | | | |
| WO | 9507361 | 3/1995 | | | | | | |
| WO | 9513381 | 5/1995 | | | | | | |
| WO | 9513538 | 5/1995 | | | | | | |
| WO | 9515400 | 6/1995 | | | | | | |
| WO | 9525737 | 9/1995 | | | | | | |
| WO | 9531429 | 11/1995 | | | | | | |
| WO | 9605323 | 2/1996 | | | | | | |
| WO | 9610648 | 4/1996 | | | | | | |
| WO | 9614406 | 5/1996 | | | | | | |
| WO | 9615262 A2 | 5/1996 | | | | | | |
| WO | 9617080 A1 | 6/1996 | | | | | | |
| WO | 9627681 | 9/1996 | | | | | | |
| WO | 9629431 | 9/1996 | | | | | | |
| WO | 9630545 | 10/1996 | | | | | | |
| WO | 9632504 | 10/1996 | | | | | | |
| WO | 9636731 | 11/1996 | | | | | | |
| WO | 9636732 | 11/1996 | | | | | | |
| WO | 9636986 A1 | 11/1996 | | | | | | |
| WO | 9636987 | 11/1996 | | | | | | |
| WO | 9637630 | 11/1996 | | | | | | |
| WO | 9639437 | 12/1996 | | | | | | |
| WO | 9708306 | 3/1997 | | | | | | |
| WO | 3719110 | 5/1997 | | | | | | |
| WO | 9733000 | 9/1997 | | | | | | |
| WO | 9737041 | 10/1997 | | | | | | |
| WO | 9740462 | 10/1997 | | | | | | |
| WO | 9742348 | 11/1997 | | | | | | |
| WO | 9743617 | 11/1997 | | | | | | |

OTHER PUBLICATIONS

Andersen, et al., "Electrospray ionization and matrix assisted laser desorption/ionization mass spectromrtry: Powerful analytical tools in recombinant protein chemistry", *Nature Biotech.*, 14:449–457 (1996).

Ardrey, "Electrospray mass spectrometry", *Spectroscopy Europe*, 4: pp. 10, 12, 14, 16, 18, 20 (1992).

Arlinghaus et al., "Applications of resonance ionization spectroscopy for semiconductor, environmental and biomedical analysis, and for DNA sequencing", *SPIE, Opt. Methods Ultrasensitive Detect Anal. Tech. Appl.*, 1435:26–35 (1991).

Bains, "DNA Sequencing By Mass Spectrometry: Outline of a Potential Future Application", *Chimicaoggi*, 9:13–16 (1991).

Bains, "Setting a Sequence to Sequence a Sequence", *Biotechnol.*, 10:757–758 (1992).

Barany F., "Genetic disease detection and DNA amplification using cloned thermostable ligase", *Proc. Natl. Acad. Sci.*, 88:189–193 (1991).

Barrell B., "DNA sequencing: present limitations and prospects for the future", *FASEB Journal*, 5:40–45 (1991).

Batista–Viera et al., "A new method for reversible immobilization of thiol biomolecules based on solid–phase bound thiolsulfonante groups," *App. Biochem and Biotech*, 31:175–195 (1991).

Beck et al., "Chemiluminescent detection of DNA: application for DNA sequencing and hybridization", *Nucl. Acids Res.*, 17(13):5115–5123 (1989).

Benner et al., "Identification of Denatured Double–stranded DNA by Matrix–assisted Laser Desorption/Ionization Time–of–Flight Mass Spectrometry", *Rapid Commun. Mass Spectrom.*, 9:537–540 (1995).

Braun, A. et al., "Molecular analysis of the gene for the human vitamin–D–binding protein (group–specific component): allelic differences of the common genetic GC types", *Hum. Genet.*, 89:401–406 (1992).

Braun et al., "Improved Analysis of Microsatellites Using Mass Spectrometry", *Genomics, 46*:18–23 (1997).

Braun et al., "Detecting CFTR gene mutations by using primer oligo base extension and mass spectrometry", *Clinical Chemistry, 43*(7):1151–1158 (1997).

Brennan et al., "New Methods to Sequence DNA By Mass Spectrometry", *SPIE New Technol. Cytom. Mol. Biol., 1206*:60–67 (1990).

Broude et al., "Enhanced DNA sequencing by hybridization (streptavidin/biotin/stacking interaction/T4 DNA ligase/DNA polymerase)", *Proc. Natl. Acad. Sci. USA, 91*:3072–3076 (1994).

Bugawan et al., "A method for typing polymorphism at the HLA–A locus using PCR amplification and immobilized oligonucleotide probes," *Tissue Antigens 44*:137–147 (1994).

Busch et al. "Mass spectrometry of large, fragile, and involatile molecules," *Science, 218*:247–254 (1982).

Cantor et al., "Instrumentation in molecular biomedical diagnostics: an overview", *Genet Anal., 14*:31–36 (1997).

Cantor, C.R. and Little, D.P., "Massive attack on high–throughput biology", *Nat. Genet., 20*:5–6 (1998).

Cantor C.R., "How will the Human Genome Project improve our quality of life?" *Nature Biotechnol., 16*:212–213 (1998).

Carrero–Valenzuela et al., "Human cytochrome c oxidase subunit Vlb: characterization and mapping of a multigene family", *Gene, 102*:229–236 (1991).

Certified English translation of: Elov et al. "Synthesis of RNA using T7 RNA polymerase and immobilized DNA in a stream type reactor", *Bioorganicheskaia Khimia, 17*(6):789–94.

Certified English translation of Japanses patent 6–294796, "Nucleic acid analysis method.", 1994.

Certified English translation of European patent 0412883A1, "Fast screening and/or identification of a single base on a nucleic acid sequence, including applications.", Feb. 13, 1991.

Certified English translation of PCT Patent Application WO 98/03257, "Solid supports for analytical measurement methods, their production and their use.", 1998.

Chait et al., "Weighing naked proteins: practical, high–accuracy mass measurement of peptides and proteins," *Science, 257*:1885–1894 (1992).

Chee, "Enzymatic multiplex DNA sequencing," *Nucleic Acids Res. 19*(12):3301–3305 (1991).

Chen et al., "Laser mass spectrometry for DNA fingerprinting for forensic applications", *Annual Meeting of the Society of Photo Optical Instrumentation Engineers*, Jul. 24–29, 1994.

Church et al., "Multiplex DNA Sequencing", *Science, 240*:185–188 (1988).

Cohen et al., "Emerging Technologies for Sequencing Antisense Oligonucleotides: Capillary Electrophoresis and Mass Spectrometry," *Advanced Chromatography, 36*:127–162 (1996).

Collins et al., "A DNA Polymorphism Discovery Resource for Research on Human Genetic Variation", *Genome Res., 8*:1229–1231 (1998).

Cosstick et al., "Synthesis and Properties of dithymidine phosphate analogues containing 3'–thiothimidine," *Nucleic Acid Research, 18*:829–835 (1990).

Cotton, R.G.H., "Current methods of mutation detection", *Mutation Res., 285*:125–144 (1993).

Cotton et al., "Reactivity of cytosine and thymine in single–base–pair mismatches with hydroxylamine and osmium tetroxide and its application to the study of mutations", *Proc. Natl. Acad. Sci. USA, 85*:4397–4401 (1988).

Covey et al., "The Determination of Protein, Oligonucleotide and Peptide Molecular Weights by Ion–spray Mass Spectrometry", *Rapid Communications in Mass Spectrometry, 2*(11):249–256 (11):249–256 (1988).

Crain, P.F., "Mass spectrometric techniques in nucleic acid research", *Mass Spectr. Rev., 9*:505–544 (1990).

Cronin et al., "Cystic Fibrosis Mutation Detection by Hybridization to Light–Generated DNA Probe Arrays", *Hum. Mutat., 7*:244–255 (1996).

*Culture of Animal Cells*, A Manual of Basic Technique, Book: 2nd Edition, Frehney, R.I., Alan R. Liss, Inc., New York. (1987).

Derwent# 007515331, WPI Acc. No. 88–149264/198822, citing European Patent No. EP 269520 A, "New HIV–2 retrovirus causing AIDS—and new antigenic proteins, antibodies and complementary nucleic acid sequences", published Jun. 1,1988.

Derwent# 007678032, WPI Acc No. 88–311964/198844, citing Japanses Patent Application JP 63230086 A, "Carrier immoblilising physiological active substance —comprises binding chain–form disulphide cpd. via epoxy gp. with latex contg. polymer particles.", 1988.

Derwent# 008221915, WPI Acc. No. 90–108916/199015, citing European Patent Application EP 0360676 A, "Size analysis of biological mol. fragments –by mass spectrometry, esp. in nucleic acid sequencing.", 1990.

Derwent# 008221916, WPI Acc. No. 1990–108917/199015, citing European Patent EP 0360677 B, "Identification of sub–units in complex mols. —by mass spectrometry, esp. in nucleic acid sequencing.", 1990.

Derwent# 008246197, WPI Acc. No. 1990–133198/199018, citing German Patent DE 3930312 A), "Nucleic acid sequencing–involving amplification–denaturation cycles in presence of deoxy–nucleoside alpha–thio–triphosphate.", 1990.

Derwent# 008415766, WPI Acc. No. 90–302767/199040, citing Japanese Patent No. JP 2215399 A, "Method for detecting DNA—includes denaturing to single strand, combining wih DNA primer having corresp. base sequence forming replicator etc.", 1990.

Derwent# 008434790, WPI Acc. No. 1990–321790/199043, citing German Patent DE 4011991 A, "Simultaneous sequencing if several DNA samples—by cloning into separate vectors, complementary strand synthesis from specific fluorescent labelled primers, electrophoresis sepn. etc.", 1990.

Derwent# 008541935, WPI Acc. No. 1991–045998/199107, citing PCT Patent Application WO 9102087 A, "Detecting single base in nucleic acid sequence –by hybridisation with primer adjacent to the specific base, then incorporation of detectable modified nucleotide.", 1991.

Derwent# 009135586, WPI Acc. No. 1992–263024, citing Japanese Patent JP 4178359 A, "New anti–inflammatory tetracycline derivs. —for treating articular rheumatism, osteoarthritis, Reiter's syndrome, Lyme disease, etc.", 1992.

Derwent# 010222178, WPI Acc. No. 95–123433/199516, citing PCT Patent Application WO 9507361 A, "Detecting presence and position of mutation(s) in double stranded DNA –by amplification, labelling strands with different markers, hybridisation and detecting heteroduplex by cleavage of unpaired strands.", 1995.

Derwent# 010643408, WPI Acc. No. 1996–140362/199615, citing German Patent DE 4431174 A, "Detecting tumour specific mRNA by conversion to cDNA and amplification –provides early, sensitive and specific diagnosis and monitoring, partic. by analysis of blood or sputum.", 1996.

Derwent# 010634381, WPI Acc. No. 1996–131334/199614, citing PCT Patent Application WO 9605323 A, "Nucleic acid amplification and opt. detection –using construcr comprising complementary strand linked to RNA polymerase promoter.", 1996.

Derwent# 010725941, WPI Acc. No. 1996–222896/199623, citing German Patent No. DE. 4438630 A, "Amplification of non–characterized DNA fragment–using only a single primer, with formation of hairpin loops during a second strand synthesis.", 1996.

Derwent# 011458787, WPI Acc. No. 1997–436694/199741, citing German Patent No. DE 19628178 C, "Loading matrix–assisted laser desorption–ionisation sample plate for mass spectrometric analysis—using simple multi–pipette to prepare tens of thousands of samples rapiadly and reliably for e.g. biochemical and genetic investigations optionally using electrophoretic concentration and delivery technique.", 1997.

Derwent# 012012061, WPI Acc. No. 1998–428971/199837, citing German Patent No. DE19731479 A, "Device for analysis of target chemcicals has light emitting array –with chemical binder elements attached to capture target chemicals which change emitted light pattern accordingly.", 1998.

Doktycz et al., "Analysis pf Polymerase Chain Reaction–Amplified DNA Products by Mass Spectrometry Using Matrix–Assisted Laser Desorption and Electrospray: Current Status", *Anal. Biochem., 230*:205–214 (1995).

Donis–Keller et al., "Mapping adenines, guanines, and pyrimidines in RNA", *Nucl. Acids Res., 4(8)*:2547–2537 (1997).

Donis–Keller et al., "Phy M: an RNase activity specific for U and A residues useful in RNA sequence analysis", *Nucl. Acids Res., 8(14)*:3133–3142 (1977).

Drmanac et al., "Sequencing of Megabase Plus DNA by Hybridization: Theory of the Method", *Genomics, 4*:114–128 (1989).

Dubiley et al., "Polymorphism analysis and gene detection by minisequencing on an array of gel–immobilized primers", *Nucl. Acids Res., 27(18)*:e 19 (i–vi) (1999).

Duchateau et al., "Selection of buffers and of an ion–pairing agent for thermospray liquid chromatography–mass spectrometric analysis of ionic compounds," *J Chromatogr 552*:605–612 (1991).

Eckstein, F., ed. *Oligonucleotides and Analogues: A Practical Approach* Oxford:Oxford University Press, pp. 56–57, 137–139, 256–259 (1991).

Edmonds et al., "Thermospray liquid chromatography–mass spectrometry of nucleosides and of enzymatic hydroysates of nucleic acids", *Nucl. Acids Res., 13(22)*:8197–8206 (1985).

Y Elov et al. "Synthesis of RNA using T7 RNA polymerase and immobilized DNA in a stream type reactor", *Bioorganicheskaia Khimia, 17(6)*:789–94, 1991.

Erdogan et al., "Detection of mitochondrial single nucleotide polymorphisms using a primer elongation reaction on oligonucleotide microarrays", *Nucl. Acids Res., 29(7)*e36:2–7 (2001).

Ferrie et al., "Development, Multiplexing, and Application of ARMS Tests for Common Mutations in the CFTR Gene", *Am. J. Hum. Genet., 51*:251–262 (1992).

Foster, M.W. and Freeman, W.L., "Naming Names in Human Genetic Variation Research", *Genome Res., 8*:755–757 (1998).

Frank and Köster, "DNA chain length and the influence of base composition on electrophoretic mobility of oligodeoxyribonucleotides in polyacrylamide–gels", *Nucl. Acids Res., 6(6)*:2069–2087 (1979).

Frohman, "Cloning PCR Products," Chapter 12 in *The Polymerase Chain Reaction*, Mullis et al. Eds., Birkhauser, Boston, pp. 14–37 (1994).

Fu et al., "A DNA Sequencing Strategy Which Requires Only Five Bases of Known Terminal Sequence For Priming", abstract: *Group Mapping and Sequencing*, Cold Spring harbor Laboratory, pp. 1 (1995).

Fu et al., "A DNA sequencing strategy that requires only five bases of known terminal sequence for priming", *Proc. Natl. Acad. Sci. USA, 92*:10162–10166 (1995).

Fu et al., "Efficient preparation of short DNA sequence ladders potentially suitable for MALDI–TOF DNA sequencing", *Genetic Analysis: Biomolecular Engineering, 12*:137–142 (1996).

Fu et al., "Sequencing double–stranded DNA by strand displacement", *Nucl. Acids Res., 25(3)*:677–679 (1997).

Fu et al., "Sequencing exons 5 to 8 of the p53 gene by MALDI–TOF mass spectrometry", *Nature Biotechnol., 16*:381–384 (1998).

Ganem et al., "Detection of Oligonucleotide Duplex Forms by Ion–Spray Mass Spectrometry", *Tetrahedron Letters, 34(9)*:1445–1448 (1993).

Gasparini et al., "Detection of a neurofibromatosis type I (NF1) homologous sequence by PCR: implications for the diagnosis and screening of genetic diseases", *Mol. Cell Probes, 7*:415–418 (1993).

Gasparini et al., "Restriction site generating–polymerase chain reaction (RG–PCR) for the probeless detection of hidden genetic variation: application to the study of some common cystic fibrosis mutations", *Mol. Cell. Probes, 6*:1–7 (1992).

*Gene Transfer Vectors for Mammalian Cells*, Book: *Current Communications In Molecular Biology*, Miller, J.H. and Calos, M.P. (Eds.), Cold Spring Harbor Laboratory, (1987).

George et al, "Current Methods in Sequence Comparison and Analysis," Chapter 12 of: Macromolecule Sequencing and Synthesis, Selected Methods and Applications Schlesinger (Ed.) 127–149 (1988).

Giannattasio et al., "Molecular screening of genetic defects with RNA–SSCP analysis: the PKU and cystinuria model", *Mol. Cell Probes, 9*:201–205 (1995).

Gibbs et al., "Detection of single DNA base difference by competitive oligonucleotide priming", *Nucl. Acids Res., 17(7)*:2437–2448 (1989).

Graber et al., "Differential sequencing with mass spectrometry", *Genet. Anal., 14*:215–219 (1999).

Graber et al., "Advances in DNA diagnostics", *Curr. Opin. Biotechnol., 9*:14–18 (1998).

Griffin, H.G. and Griffin, A.M., "DNA Sequencing. Recent Innovations and Future Trends", *Appl. Biochem. Biotechnol.,* 38:147–159 (1993).

Gross et al., "Investigations of the Metastable Decay of DNA Under Ultraviolet Matrix–Assisted Laser Desorption/Ionization Conditions with Post–Source–Decay Analysis and Hydrogen/Deuterium Exchange", *J. Amer. Soc. for Mass Spectrom.,* 9:866–878 (1998).

Gruić–Sovulj et al., "Matrix–assisted laser desorption/ionization mass spectrometry of transfer ribonucleic acids isolated from yeast", *Nucl. Acids Res.,* 25(9):1859–1861 (1997).

Guatelli et al., "Isothermal, in vitro amplification of nucleic acids by a multienzyme reaction modeled after retroviral replication", *Proc. Natl. Acad. Sci. USA,* 87:1874–1878 (1990).

Haag et al., Rapid identification and speciation of Haemophilus bacteria by matrix–assisted laser desorption/ionization time–of–flight mass spectrometry, *J. of Mass Spectrometry* 33(8):750–756 (1998).

Haglund et al., "Matrix–Assisted Laser–Desorption Mass Spectrometry Of DNA Using An Infrared Free–Electon Laser", *SPIE,* 1854:117–128 (1993).

Hahner et al., "Sequencing of nucleic acids by MALDI–MS", *Proceedings ASMS Conference on Mass Spectrometry and Allied Topics,* Portland, Oregon, (44th), pp. 983 (1996).

Hainaut et al., "Database of p53 gene somatic mutations in human tumors and cell lines: updated compilation and future prospects", *Nucl. Acids Res.,* 25(1):151–157 (1997).

*Handbook Of Experimental Immunology In Four Volumes,* Book: vol. 1, "Immunochemistry", Weir, D.M., (and co–Eds.), Fourth Edition, Blackwell Scientific Publications, Osney Mead, Oxford, (1986).

Hasan et al., "Base–boronated dinucleotides: synthesis and effect of N7–cyanoborane substitution on the base protons", *Nucl. Acids Res.,* 24(11):2150–2157 (1996).

Hayashi, K., "PCR–SSCP: A Method for Detection of Mutations", *Genet. Anal. Tech. Appl. (GATA),* 9(3):73–79 (1992).

Hensley, S., "Gemini Genomics and Sequenom Unveil Previously Unknown Genes", *Wall Street Journal,* Health Section, pp. 40 (2000).

Higgins et al., "Competitive Oligonucleotide Single–Base Extension Combined with Mass Spectrometric Detection for Mutation Screening", *BioTechniques,* 23(4):710–714 (1997).

Higuchi et al., "Kinetic PCR Analysis: Real–time Monitoring of DNA Amplification Reactions", *BioTech.,* 11:1026–1030 (1993).

Higuchi et al., "A general method of in vitro preparation and mutagenesis of DNA fragments: Study of protein and DNA interactions", *Nucl. Acids Res.,* 16:7351–7367 (1988).

HillenKamp, F. and Ehring, H., "Laser Desorption Mass Spectrometry Part 1: Basic Mechanisms And Techniques", *Mass Spectrometry in the Biological Sciences: A tutorial,* pp. 165–179 (1992).

Hu et al., "DNA Polymerase–Catalyzed Addition of Nontemplated Extra Nucleotides to the 3' End of a DNA Fragment", *DNA and Cell Biol.,* 12(8):763–770 (1993).

Hu et al., "Primer specific and mispair extension analysis (PSMEA) as a simple approach to fast genotyping", *Nucl. Acids Res.,* 26(21):5013–5015 (1998).

Hyman, E.D., "A New Method of Sequencing DNA", *Anal. Biochem.,* 174:423–436 (1988).

*Immobilised cells and enzymes,* a practical approach, Woodward, J. (Ed.), IRL Press Limited, Oxford, Washington, DC, 1985.

*Immunochemical Methods in Cell and Molecular Biology,* Mayer, R.J. and Walker, J.H. (Eds.), Academic Press, London, 1987).

Innis et al., "DNA Sequencing with *Thermus aquaticus* DNA polymerase and direct sequencing of polymerase chain reaction–amplified DNA", *Proc. Natl. Acad. Sci. USA,* 85:9436–9440 (1988).

Jacobson et al., "Applications of mass spectrometry to DNA fingerprinting and DNA sequencing", *International Symposium on the Forensic Aspects of DNA Analysis,* pp. 1–18, Mar. 29–Apr. 2, 1993.

Jacobson et al., "Applications of Mass Spectrometry to DNA Sequencing", *Genet. Anal. Tech. Appl. (GATA),* 8(8):223–229 (1991).

Jain, "Delivery of Molecular Medicine to Solid Tumors", *Science,* 271:1079–1080 (1996).

Jett et al., "High–Speed DNA Sequencing: An Approach Based Upon fluorescence Detection of Single Molecules", *J. Bio. Strut. & Dynam.,* 7(2):301–309 (1989).

Ji et al., "Two–dimensional electrophoretic analysis of proteins expressed by normal and cancerous human crypts: Application of mass spectrometry to peptide–mass fingerprinting", *Electrophoresis,* 15:391–405 (1994).

Juhasz et al., "Applications of Delayed Extraction Matrix–Assisted Laser Desorption Ionization Time–of–Flight Mass Spectrometry to Oligonucleotide Analysis", *Anal. Chem.,* 68(6):941–946 (1996).

Jurinke et al., "Analysis of Ligase Chain Reaction products via Matrix–Assisted Laser Desorption/Ionization Time–of–Flight–Mass Spectrometry", *Anal. Biochem.,* 237:174–181 (1996).

Jurinke et al., "Application of nested PCR and mass spectrometry for DNA–based virus detection: HBV–DNA detected in the majority of isolated anti–HBc positive sera", *Genetic Analysis: Biomolecular Engineering,* 14:97–102 (1998).

Jurinke et al., "Detection of hepatitis B virus DNA in serum samples via nested PCR and MALDI–TOF mass spectrometry," *Genetic Analysis: Biomolecular Engineering,* 13:67–71 (1996).

Jurinke et al., "Recovery of Nucleic Acids from Immobilized Biotin–Streptavidin Complexes Using Ammonium Hydroxide and Applications in MALDI–TOF Mass Spectrometry", *Anal. Chem.,* 69:904–910 (1997).

Karas, et al., "UV Laser Matrix Desorption/Ionization Mass Spectrometry Of Proteins In The 100,000 Dalton Range", *J. Mass Spectrom. Ion Processes,* 92:231–242 (1989).

Keen et al., "Rapid detection of single base mismatches as heteroduplexes on Hydrolink gels", *Trends Genet.,* 7:5 (1991).

Khrapko et al., "An oligonucleotide hybridization approach to DNA sequencing", *FEB,* 256(1,2):118–122 (1989).

khrapko et al., "A method for DNA sequencing by hybridization with oligonucleotide matrix", *J. DNA Sequencing and Mapping,* 1:375–388 (1991).

Kirpekar et al., "DNA sequence analysis by MALDI mass spectrometry", *Nucl. Acids Res.,* 26(11):2554–2559 (1998).

Kirpekar et al., "Matrix assisted laser desorption/ionization mass spectrometry of enzymatically synthesized RNA up to 150 kDa", *Nucl. Acids Res.,* 22(19):3866–3870 (1994).

Kirpekar et al., "7–Deaza Purine Bases Offer a Higher Ion Stability in the Analysis of DNA by Matrix–Assisted Laser Desorption/Ionization Mass Spectrometry", *Rapid Commun. Mass Spectrom.,* 9:525–531 (1995).

Kornher, J.S. and Livak, K.J., "Mutation detection using nucleotide analogs that alter electrophoretic mobility", *Nucl. Acids Res.,* 17(19):7779–7784 (1989).

Köster et al., "A strategy for rapid and efficient DNA sequencing by mass spectrometry", *Nature Biotechnology,* 14:1123–1128 (1996).

Köster et al., "N–Acyl Protecting Groups For Deoxynucleotides: A Quantitative And Comparative Study", *Tetrahedron,* 37:363–369 (1981).

Köster et al. "Oligonucleotide synthesis and multiplex DNA sequencing using chemiluminescent detection", *Nucl. Acids Res.*, Symposium Series No. 24, pp. 318–321 (1991).

Köster et al., "Some improvements in the synthesis of DNA of biological interest", *Nucl. Acids Res.,* 7:39–59 (1980).

Köster et al., "Well–Defined Insoluble Primers for the Enzymatic Synthesis of Oligo–and Polynucleotides", *Hoppe–Seyler's Z. Physiol. Chem.,* 359:1579–1589 (1978).

Kozal et al., "Extensive polymorphisms observed in HIV–1 clade B protease gene using high–density oligonucleotide arrays", *Nature,* 2(7):753–759 (1996).

Krishnamurthy and Ross, Rapid identification of bacteria by direct matrix assisted laser desorption/ionization mass spectrometric analysis of whole cells, *Rapid Comm in Mass Spectrometry* 10(15):1992–1996 (1996).

Krishnamurthy et al., Biomolecules and mass spectroscopy, *J. of Natural Toxins* 6(2):121–162 (1997).

Kuppuswamy et al., "Single nucleotide primer extension to detect genetic diseases: Experimental applicatiion to hemophilia B (factor IX) and cystic fibosis genes", *Proc. Natl. Acad. Sci. USA,* 88:1143–1147 (1991).

Kussmann, et al., "Matrix–Assisted Laser Desorption/Ionization Mass Spectrometry Sample Preparation Techniques Designed for Various Peptide and Protein Analytes",*J. Mass Spec.,* 32:593–601 (1997).

Kwoh et al., "Transcription–based amplification system and detection of amplified human immunodeficiency virus type 1 with a bead–based sandwich hybridization format", *Proc. Natl. Acad. Sci. USA,* 86:1173–1177 (1989).

Labeit et al., "Laboratory Methods: A New Method of DNA Sequencing Using Deoxynucleoside α–Thiotriphosphates", *DNA,* 5:173–177 (1986).

Lagerström et al., "Capture PCR: Efficient amplification of DNA fragments adjacent to a known seqence in human YAC DNA," *PCR Methods and Applications* 1:111–119 (1991).

Landegren et al., "A Ligase–Mediated Gene Detection Technique", *Science,* 241:1077–1080 (1988).

Landegren et al., "DNA Diagnostics—Molecular techniques and automation", *Science,* 242:229–237 (1988).

Lecchi, P. and Pannell, L.K., "The Detection of Intact Double–Stranded DNA by MALDI", *J. Am. Soc. Mass Spectrom.,* 6:972 (1995).

Leonard et al., "High–resolution structure of mutagenic lesion in DNA", *Proc. Nat. Acad. Sci. Biochem.,* 87:9573–9576 (1990).

Li et al., "Analysis of Single Mammalian Cell Lysates by Mass Spectrometry", *J. Am. Chem. Soc.,* 118:11662–11663 (1996).

Li et al., "Boron–containing oligodeoxyribonucleotide 14mer duplexes: enzymatic synthesis and melting studies", *Nucl. Acids Res.,* 23(21):4495–4501 (1995).

Li et al., "High–Resolution MALDI Fourier Transform Mass Spectrometry of Oligonucleotides", *Anal. Chem.,* 68(13):2090–2096 (1996).

Limbach et al., "Molecular mass measurement of intact ribonucleic acids via electrospray ionization quadrupole mass spectrometry", *J. Am. Soc. Mass Spectrom.,* 6:27–39 (1995).

Little et al., "Identification of Apolipoprotein E Polymorphisms Using Temperature Cycled Primer Oligo Base Extension and Mass Spectrometry", *Short Communication, Eur. J. Clin. Chem. Clin. Biochem.* 35(7):545–548 (1997).

Little et al., "Detection of RET proto–oncogene codon 634 mutations using mass spectrometry," *J. Mol. Med.,* 75:745–750 (1997).

Little et al., "Direct detection of synthetic and biologically generated double–stranded DNA by MALDI–TOF MS," *International Journal of Mass Spectrometry and Ion Processes,* 169–170:323–330 (1997).

Little et al., "MALDI on a Chip: Analysis of Arrays of Low–Femtomole to Subfemtomole Quantities of Synthetic Oligonucleotides and DNA Diagnostic Products Dispensed by a Piezoelectric Pipet", *Anal. Chem.,* 69:4540–4546 (1997).

Little et al., "Mass spectrometry from miniaturized arrays for full comparative DNA analysis," *Nature Medicine,* 3(12):1413–1416 (1997).

Little et al., "Rapid Sequencing of Oligonucleotides by High–Resolution Mass Spectrometry", *J. Am. Chem. Soc.,* 116:4893–4897 (1994).

Little et al., "Verification of 50– to 100–mer DNA and RNA sequences with high–resolution mass spectrometry", *Proc. Natl. Acad. Sci. USA,* 92:2318–2322 (1995).

Liu, et al., "Use of a Nitrocellulose Film Substrate in Matrix–Assisted Laser Desorption/Ionization Mass Spectrometry for DNA Mapping and Screening", *Anal. Chem.,* 67:3482 (1995).

Lizardi et al., "Exponential Amplification of Recombinant–RNA Hybridization Probes", *Bio/Technol.,* 6:1197–1202 (1988).

Marshall, A. and Hodgson, J., "DNA chips: An array of possibilities", *Nat. Biotechnol.,* 16:27–31 (1998).

Martin, W.J., "New technologies for large–genome sequencing", *Genome,* 31:1073–1080 (1989).

Matthews et al., "Analytical Strategies for the Use of DNA Probes", *Anal. Biochem.,* 169:1–25 (1988).

Matteucci, M.D. and Caruthers, M.H., "Synthesis of Deoxyoligonucleotides on a Polymer Support", *J. Amer. Chem. Soc.,* 103:3185–3191 (1981).

Maxam, A.M. and Gilbert, W., "A new method for sequencing DNA", *Proc. Natl. Acad. Sci. USA,* 74(2):560–564 (1977).

Maxam, A.M. and Gilbert, W., "Sequencing End–Labeled DNA with Base–Specific Chemical Cleavages", *Methods in Enzymol.,* 65:499–560 (1980).

McLafferty, et al., "Double stranded DNA sequencing by tandem mass spectrometry", *Intl. J. Mass Spectrom. Ion Processes, 165/166*:457–466 (1997).

*Methods of Enzymol.*, vol. 193 Mass Spectrometry (McCloskey, editor), p. 425, Academic Press, New York, (1990).

Miyazaki et al., "The First Japanese Case of Hb Santa Ana, an Unstable Abnormal Hemoglobin, Identified Rapidly by Electrospray Ionization Mass Spectrometry",*Internal Medicine, 36(3)*:365–370 (1997).

Mizusawa et al., "Improvement of the dideoxy chain termination method of DNA sequencing by use of deoxy–7–deazaguanosine triphosphate in place of dGTP", *Nucl. Acids Res., 14*:1319–1325 (1986).

*Molecular Cloning*, a Laboratory Manual, Book: Second Edition, Sambrook, J. and Russell, D.W. (Eds.), Cold Spring Harbor Laboratory Press, (1989).

Monforte, J.A. and Becker, C.H., "High–throughput DNA analysis by time–of–flight mass spectrometry," *Nature Medicine, 3(3)*:36–42 (1997).

Mosca et al., "Mass spectrometry and DNA analysis", *Hemoglobin, 17*:261–268 (1993).

Mullis, K.B. and Faloona, F.A., "Specific Synthesis of DNA in Vitro via a Polymerase–Catalyzed Chain Reaction", *Meth. Enzymol., 155*:335:350 (1987).

Murdock et al., "The age–related accumulation of a mitochondrial DNA control region mutation in muscle, but not brain, detected by a sensitive PNA–directed PCR clamping based method", *Nucl. Acids Res., 28(21)*:4350–4355 (2000).

Murray, K.K., "DNA Sequencing by Mass Spectrometry", *J. Mass. Spect., 31*:1203–1215 (1996).

Myers et al., "Detection of Single Base Substitutions by Ribonuclease Cleavage at Mismatches in RNA:DNA Duplexes", *Science, 230*:1242–1246 (1985).

Myers et al., "Detection of single base substitutions on total genomic DNA", *Nature, 313*:495–498 (1985).

Naeve et al., "Accuracy of Automated DNA Sequencing: A Multi–Laboratory Comparsion of Sequencing Results", *Biotechiques, 19*:448–453 (1995).

Naito et al., "Detection of Tyrosine Hydroxylase mRNA and Minimal Neuroblastoma Cells by Reverse Transcription–Polymerase Chain Reaction", *Eur. J. Cancer, 27*:762–765 (1991).

Nakajima et al., "An Alternate Nonisotopic Technique Of PCR–Mediated Allele–Specific Oligonucleotide Analysis For The Detection of a Point Mutation", *Res. Commun. Chem. Pathol. Pharmacol., 79(1)*:3–10 (1993).

Nakamaye et al. "Direct Sequencing of polymerase chain reaction amplified DNA fragments through the incorporation of deoxynucleoside a–thiotriphosphates," *Nucl. Acids. Research. 16*:9947–9959 (1988).

Nakayabu et al., "Mismatched nucleotides may facilitate expansion of trinucleotide repeats in genetic diseases," *Nucl. Acids Res., 26(8)*:1980–1984 (1998).

Nelson et al., "Time–of–Flight Mass Spectrometry of Nucleic Acids by Laser Ablation and Ionization from a Frozen Aqueous Matrix", *Rapid Communications in Mass Spectrometry, 4*:348–351 (1990).

Nepom et al., "HLA–DQα Polymorphisms: Oligonucleotide Probes Characterize the Contribution of First and Second Domains to Electrophoretic Variants", *Hum. Immunol., 25*:257–267 (1989).

Newton et al., "Analysis of any point mutation in DNA. The amplification refractory mutation system (ARMS)", *Nucl. Acids Res., 17(7)*:2503–2516 (1989).

Newton et al., "The production of PCR products with 5' single–stranded tails using primers that incorporate novel phosphoramidite intermediates," *Nucl. Acids. Res., 21(5)*:1155–1162 (1993).

Nickerson et al., "Automated DNA diagnostics using an ELISA–based oligonucleotide ligation assay", *Proc. Natl. Acad. Sci. USA, 87*:8923–8927.

Nielsen, et al., "Sequence–Selective Recognition of DNA by Strand Displacement with a Thymine–Substituted Polyamide", *Science, 254*:1497 (1991).

Nikiforov, T.T. and Rogers, Y., "The Use of 96–Well Polystryrene Plates for DNA Hybridization–Based Assays: An Evaluation of Different Approaches to Oligonucleotide Immobilization", *Anal. Biochem., 227*:201–209 (1995).

Nikiforov et al., "Genetic Bit Analysis: a Solid Phase Method for Typing Single Nucleotide Polymorphisms", *Nucl. Acids Res., 22(20)*:4167–4175 (1994).

Nordhoff et al., "Ion stability of nucleic acids in infrared matrix–assisted laser desorption/ionization mass spectrometry", *Nucl. Acids Res., 21(15)*:3347–3357 (1993).

Norton et al., "Targeting Peptide Nucleic Acid–Protein Conjugates to Structural Features within Duplex DNA", *Bioorg. Med. Chem., 3(4)*:437–445 (1995).

Nyrén et al., "Solid Phase DNA Minisequencing by an Enzymatic Luminometric Inorganic Pyrophosphate Detection Assay", *Anal. Biochem., 208*:171–175 (1993).

O'Connor et al., "Isotopic Assignment in Large–Molecule Mass Spectra by Fragmentation of a Selected Isotopic Peak", *Anal. Chem., 68*:542–545 (1996).

O'Donnell et al., "High–Density, Covalent Attachment of DNA to Silicon Wafers for Analysis by MALDI–TOF Mass Spectrometry", *Anal. Chem., 69(13)*:2438–2443 (1997).

O'Donnell et al., "MassArray as an Enabling Technology for the Industrial–Scale Analysis of DNA", *Genetic Engineering News, 17(21)*:39–41 (1997).

O'Donnell–Maloney et al., "Microfabrication and array technologies for DNA sequencing and diagnostics", *Genetic Analysis: Biomolecular Engineering, 13*:151–157 (1996).

O'Donnell–Maloney et al., "The development of microfabricated arrays for DNA sequencing and analysis", *TIBTECH, 14*:401–407 (1996).

Olsson, "Isolation and Characterization of a tumor necrosis factor binding protein from urine," *Eur. J. Haematol., 42*:270–275 (1989) (XP000937599).

Ordoukhanian et al., "Design and Synthesis of a Versatile Photocleavable DNA Building Block: Application to Phototriggered Hybridation", *J. Am. Chem. Soc., 117*:9570–9571 (1995).

Orita et al., "Detection of polymorphisms of human DNA by gel electrophoresis as single–strand conformation polymorphisms", *Proc. Natl. Acad Sci. USA, 86*:2766–2770 (1989).

Overberg et al., "Laser Desorption Mass Spectrometry. Part II Performance and Applications of Matrix–Assisted Laser Desorption/Ionization of Large Biomolecules", *Mass Spect. Biol. Sci.: A Tutorial*, pp. 181–197, (1992).

Palejwala et al., "Quantitative multiplex sequence analysis of mutational hot spots. Frequency and specificity of mutations induced by site–specific ethenocytosine in m13 viral DNA," *Biochemistry 32*:4105–4111 (1993).

Pasini et al., "RET mutations in human disease", *Trends in Genetics; 12*:138–144.

Pieles et al., "Matrix–assisted laser desorption ionization time–of–flight mass spectrometry: a powerful tool for the mass and sequence analysis of natural and modified oligonucleotides", *Nucl. Acids Res., 21(14)*:3191–3196 (1993).

Pomerantz et al., "Determination of Oligonucleotide Composition for Mass Spectrometrically Measured Molecular Weight", *Am. Soc. Mass Spectrom., 4*:204–209 (1993).

Porter et al., "N7–Cyanoborane–2"–Deoxyguanosine–5'–Triphosphate Is a Good Substrate for DNA Polymerase, *Biochem.*, 34:11963–11969 (1995).

Prezant, T. R. and Fischel–Ghodsian, N., "Trapped–Oligonucleotide Nucleotide Incorporation (TONI) Assay, a Simple Method for Screening Point Mutations", *Hum. Mutat.*, 1:159–164 (1992).

Prome et al., "Use of Combined Mass Spectrometry Methods for the Characterization of a New Variant of Human Hemoglobin: The Double Mutant Hemoglobin Villeparisis Beta 77(EF1)", *J. Am. Soc. for Mass Spectr.*, 7:163–167 (1996).

Prosser, J., "Detecting single–base mutations", *TIBTECH*, 11:238–246 (1993).

Rosenbaum, V. and Riesner, D., "Temperature–gradient gel electrophoresis. Thermodynamic analysis of nucleic acids and proteins in purified form and in cellular extracts", *Biophy. Chem.*, 26:235–246 (1987).

Saiki et al., "Analysis of enzymatically amplified β–globin and HLA–DQα DNA with allele–specific oligonucleotide probes", *Nature*, 324:163–166 (1986).

Saiki et al., "Genetic analysis of amplified DNA with immobilized sequence–specific oligonucleotide probes", *Proc. Natl. Acad. Sci. USA*, 86:6230–6234 (1989).

Saleeba, J.A. and Cotton, R.G.H., "Chemical Cleavage of Mismatch to Detect Mutations", *Meth. Enzymol.*, 217:286–295 (1993).

Sanger et al., "DNA sequencing with chain–terminating inhibitors", *Proc. Natl. Acad. Sci. USA*, 74(12):5463–5467 (1977).

Sarin et al., "Inhibition of acquired immunodeficiency syndrome virus by oligodeoxy–nucleoside methylphosphonates", *Proc. Natl. Acad. Sci. USA*, 85:7448–7451 (1988).

Sarkar et al., "Human Genetic Bi–allelic Sequences (HGBASE), a Database of Intra–genic Polymorphisms", 93(5):693–694 (1998).

Sauer et al., "A novel procedure for efficient genotyping of single nucleotide polymorphisms", *Nucl. Acids Res.*, 28(5):e13 (i–viii) (2000).

Schneider, K. and Chait, B.T., "Increased stability of nucleic acids containing 7–deaza–guanosine and 7–deaza–adenosine may enable rapid DNA sequencing by matrix–assisted laser desorption mass spectrometry", *Nucl. Acids Res.*, 23:1570–1575 (1995).

Schram, K.H., "Mass Spectrometry of Nucleic Acid Components", *Biol. Appl. of Mass Spect.*, 34:203–287 (1990).

Seela et al., "7–Deazapurine containg DNA: efficiency of $c^7G_dTP$, $c^7A_dTP$ and $C^7I_dTP$ incorporation during PCR–amplification and protection from endodeoxyribonuclease hydrolysis", *Nucl. Acids Res.*, 20(1):55–61 (1992).

Sequenom Reports On Use of Its DNA MassArray™Technology to Analyze Genes Associated with Alzheimer's Disease and Arteriosclerosis: Technology Has Applications in Drug Development, Press Release: Sep. 22, 1997, http://www.sequenom.com/pressrelease.htm.

Sequenom Reports DNA MassArray™Technology More Sensitive Than Electrophoretic Methods in Detecting Gene Mutations: Automated DNA Analysis System Can Speed Up Microsatellite Analyses, Press Release: Dec. 15, 1997, http://www.sequenom.com/pressrelease.htm.

Sequenom Signs Agreement with Bruker–Franzen Analytik to develop Mass Spectrometer For DNA Massarray Analysis, Press Release: Jan. 12, 1998, http://www.sequenom.com/pressrelease.htm.

Sequenom Uses DNA MassArray™ to Sequence Section Of Human Cancer–Related p53 Gene, Press Release: Mar. 27, 1998, http://www.sequenom.com/pressrelease.htm.

Sequenom Obtains Important New Patent For DNA MassArray Technology, , Press Release: May 24, 1999, http://www.sequenom.com/pr/pressrelease/52499.html.

Sequenom Advances the Idustrial Genomics Revolution With The Launch Of Its DNA MassArray™ Automated Process Line, Press Release: Sep. 28, 1998, http://www.sequenom.com/pressrelease.htm.

Sequenom Obtains Patents for DNA MassArray($^{SM}$) Technology, Press Release: Apr. 27, 1999, http://www.sequenom.com/pressrelease/42799.htm.

Shaler et al., "Effect of Impurities on the Matrix–Assisted Laser Desorption Mass Spectra of Single–Stranded Oligodeoxynucleotides", *Anal. Chem.*, 68:576–579 (1996).

Siegert et al., "Matrix–Assisted Laser Desorption/Ionization Time–of–Flight Mass Spectrometry for the Detection of Polymerase Chain Reaction Containing 7–Deazapurine Moieties", *Anal. Biochem.*, 243:55–65 (1996).

Siuzdak, G., "The emergence of mass spectrometry in biochemical research", *Proc. Natl. Acad. Sci. USA*, 91:11290–11297 (1994).

Smith et al., "Capillary Zone Electrophoresis–Mass Spectrometry Using an Electrospray Ionization Interface", *Anal. Chem.*, 60:436–441 (1988).

Smith R.D., "New Developments in Biochemical Mass Spectrometry: Electrospray Ionization", *Anal. Chem.*, 62:882–899 (1990).

Smith et al., "Fluorescence detection in automated DNA sequence analysis", *Nature*, 321:674–679 (1986).

Sokolov, B.P. and Prockop, J.J., "A rapid and simple PCR–based method for isolation of cDNAs from differently expressed genes", *Nucl. Acids Res.*, 22(19):4009–4015 (1994).

Sokolov, B.P., "Primer extension technique for the detection of single nucleotide in genomic DNA", *Nucl. Acids Res.*, 18(12):3671 (1989).

Stahl et al., "Solid phase DNA sequencing using the biotin–avidin system," *Nucl. Acids Res.*, 16(17):302–5–3039 (1988).

Stein et al., "Physicochemical properties of phosphorothioate oligodeoxynucleotides", *Nucl. Acids Res.*, 16(8):3209–3221 (1988).

Sun et al., "A new MALDI–TOF based mini–sequencing assay for genotyping of SNPS", *Nucl. Acids Res.*, 28(12):e68 (i–viii) (2000).

Syvänen et al., "A Primer–Guided Nucleotide Incorporation Assay in the Genotyping of Apolipoprotein E", *Genomics*, 8:684–692 (1990).

Syvänen et al., "Detection of Point Mutations by Solid–Phase Methods," *Human Mutation* 3(3):172–179 (1994).

Syvänen et al., "Identification of Individuals by analysis of Biallelic DNA markers, using PCR and Solid–Phase Minisequencing", *Am. J. Hum. Genet.*, 52:46–59.

Szybalski, "Universal restriction endonucleases: designing novel cleavage specificities by combining adapter olideoxynucleotide and enzyme moieties," *Gene* 40:169–173 (1985).

Tang et al., "Detection of 500–Nucleotide DNA by Laser Desorption Mass Spectrometry", *Rapid Commun. Mass Spectrom.*, 8:727–730 (1994).

Tang et al., "Matrix–Assisted Laser Desorption/Ionization of Restriction Enzyme–Digested DNA", *Rapid Commun. Mass Spectrom.*, 8:183–186 (1994).

Tang et al., "Matrix–assisted laser desorption/ionization mass spectrometry of immobilized duplex DNA probes", *Nucl. Acids Res.*, 23(16):3126–3131 (1995).

Tang, et al., "Improving mass resolution in MALDI/TOF analysis of DNA", *American Society of Mass Spectrometrists Conference* May 21–26, 1995.

Tobe et al., "Single–well genotyping of diallelic sequence variations by a two–color ELISA–based oligonucleotide ligation assay", *Nucl. Acids Res.*, 24(19):3728–3732 (1996).

Tomer et al., "Coaxial Continvous Flow Fast Atom Bombardment for Higher–Molecular–Weight Peptides: Comparison with Static Fast Atom Bombardment and electrospray Ionization", *Biol. Mass Spect.*, 20:783–788 (1991).

Trainor, "DNA Sequencing, Automation, and the Human Genome", *Anal. Chem.*, 62:418–426 (1990).

Ugozzoli et al., "Detection of Specific Alleles by Using Allele–Specific Primer Extension Followed by Capture on Solid Support", *Genet. Anal. Tech. Appl.(GATA)*, 9(4):107–112 (1992).

Uhlmann et al., "Antisense Oligonucleotides: A New Therapeutic Principle", *Chemical Reviews*, 90(4):544–583 (1990).

Valaskovic et al., "Attomole–Sensitivity Electropray Source for Large–Molecule Mass Spectrometry", *Anal. Chem.*, 67:3802–3805 (1995).

Valaskovic et al., "Attomole Protein Characterization by Capillary Electrophoresis–Mass Spectrometry", *Science*, 273: 1199–1202 (1996).

Van Brunt, J., "Amplifying Genes: PCR And Its Alternatives", *Bio/Technol.*, 8:291–294 (1990).

van den Boom et al., "Forward and Reverse DNA Sequencing in a Single Reaction", *Anal. Biochem.*, 256:127–129 (1998).

van den Boom et al., "Combined amplification and sequencing in a single reaction using two DNA polymerase with differential incorporation rates for dideoxynucleotides", *J. Biochem. Biophys. Methods*, 35:69–79 (1997).

Vorm et al., "Improved Resolution and Very High Sensitivity in MALDI TOF of Matrix Surfaces Made by Fast Evaporation," *Anal. Chem.*, 66:3281–3287 (1994).

Walker et al., "Multiplex strand displacement amplification (SDA) and detection of DNA sequences for *Mycobacterium tuberculosis* and other mycobacteria", *Nucl. Acids Res.*, 22(13):2670–2677 (1994).

Wallace et al., "Hybridization of synthetic oligodeoxyribonucleotides to phi chi 174 DNA: the effect of single base pair mismatch", *Nucl. Acids Res.*, 6(11):3543–3557 (1979).

Wallace et al., "Oligonucleotide directed mutagenesis of the human beta–globin gene: a general method for producing specific point mutations in cloned DNA", *Nucl. Acids Res.*, 9(15):3647–3656 (1981).

Wallace et al., "The use of synthetic oligonucleotides as hybridization probes. II. Hybridization of oligonucleotides of mixed sequence to rabbit beta–globin DNA", *Nucl. Acids Res.*, 9(4):879–894 (1981).

Welham et al., The rapid identification of intact microorganisms by matrix–assisted laser desorption/ionization time–of–flight mass spectrometry, *Pharmacy and Pharmacology Comm.* 4(2):81–87 (1998).

Williams, "Time of flight mass spectrometry of DNA laser–ablated from frozen aqueous solutions: applications to the Human Genome Project", *Intl. J. Mass Spectrom. and Ion Processes*, 131:335–344 (1994).

Wolter et al., "Negative ion FAB mass spectrometric analysis of non–charged key intermediated in oligonucleotide synthesis: rapid identification of partially protected dinucleoside monophosphates", *Biomed. Environ. Mass Spect.*, 14:111–116 (1987).

Wong et al., "Characterization of β–thalassaemia mutations using direct genomic sequencing of amplified single copy DNA", *Nature*, 330:384–386 (1987).

Wood et al., "Direct sequence data from heterogeneous creatine kinase (43 kDa) by high–resolution tandem mass spectrometry", *Biochem.*, 34:16251–16254 (1995).

Wu et al., Time–of–Flight Mass Spectrometry of Underivatized Single–Stranded DNA Oligomers by Matrix–Assisted Laser Desorption, *Anal. Chem.*, 66(10):1637–1645 (1994).

Wu et al., "The ligation amplification reaction (LAR)—amplification of specific DNA sequences using sequential rounds of template–dependent ligation," *Genomics*, 4:560–569 (1989).

Wu et al., "Allele–specific enzymatic amplification of β–globin genomic DNA for diagnosis of sickle cell anemia", *Proc. Natl. Acad. Sci. USA*, 86:2757–2760 (1989).

Yang, et al., "Detection of Hepatitis B Virus in Plasma Using Flow Cytometric Analyses of Polymerase Chain Reaction–Amplified DNA Incorporating Digoxigenin–11–dUTP", *Blood*, 81(4):1083–1088 (1993).

Yates, III, "Mass spectrometry and the age of the proteome", *J. Mass Spec.*, 33:1–19 (1998).

Zhang et al., "Single–base mutational analysis of cancer and genetic diseases using membrane bound modified oligonucleotides", *Nucl. Acids Res.*, 19:3929–3933 (1991).

Zimmermann et al., Automated Preparation and Purification of M13 Templates for DNA Sequencing, *Meth. Mol. Cell. Biol.*, 1:29–34 (1989).

Zuckermann et al., "Effcient methods for attachment of thiol specific probes to the 3'–ends of synthetic oligodeoxyribonucleotides," *Nucleic Acids Research*, 15:13 5305–5320 (1987).

Agrawal and Goodchild, "Oligoeoxynucleoside Methylphosphonates: Synthesis and Enzymic Degradation", *Tetrahedron Lett.*, 28:3539–3542 (1987).

Ausubel et al., "Synthesis and Purification of Oligonucleotides: Synthesis of Oligonucleotides", *Current Protocols Molecular Biology*, John Wiley and Sons, Inc., Media, PA, Section 2.11.1–2.11.8, Supplements 9 and 8, (1989).

Bannwarth et al., "Laboratory Methods: A System for the Simultaneous Chemical Synthesis of Different DNA Fragments on Solid Support", *DNA*, 5(5):413–419 (1986).

Bannwarth, "Gene Technology: a Challenge for a Chemist", *Chimia*, 41(9):302–313 (1987).

Bannwarth, "Solid–Phase Synthesis of Oligodeoxynucleotides Containing Phosphoramidate Internucleotide Linkages and their Specific Chemical Cleavage", *Helvetica Chimica Acta*, 71:1517–1527 (1988).

Bischoff et al., "Introduction of 5'–Terminal Functional Groups into Synthetic Oligonucleotides for Selective Immobilization", *Analytical Biochemistry*, 164:336–344 (1987).

Collins et al., "Altered Transcription of the c–abl Oncogene in K–562 and Other Chronic Myelogenous Leukemia Cells", *Science*, 225:72–74 (1984).

Cormier et al., "Synthesis of hexanucleotide analogues containing diisopropylsilyl internucleotide linkages", Nucl. Acids Res., 16:4583–4594 (1988).

Corey and Snider, "A Total Synthesis of (±)–Fumagillin", J. Am. Chem. Soc., 94:2549–2550 (1972).

Cosstick et al., "Synthesis and Phosphorus–Sulphur Bond Cleavage of 3'–Thiothymidylyl(3'–5')thymidine", J. Chem. Soc., Chem. Comm., 992–993 (1988).

Cosstick et al., "Solid Phase Synthesis of Oligonucleotides Containing 3'–Thiothymidine", Tetrahedron Lett., 30(35):4693–4696 (1989).

Daley et al., "Transformation of an interleukin 3–dependent hematopoietic cell line by the chronic myelogenous leukemia–specific P210$^{ber/abl}$ protein", Proc. Natl. Acad. Sci USA, 85:9312–9316 (1988).

Fodor et al., "Light–Directed, Spatially Addressable Parallel Chemical Synthesis", Science, 251:767–773 (1991).

Gale et al., "An 8–kilobase abl RNA transcript in Chronic myelogenous leukemia", Proc. Natl. Acad. Sci. USA, 81:5648–5652 (1984).

Ghosh et al., "Covalent attachment of oligonucleotides to solid supports", Nucl. Acids Res., 15(13):5353–5372 (1987).

Gingeras et al., "Hybridization properties of immobilized nucleic acids", Nucl. Acids Res., 15(13):5373–5390 (1987).

Glazer et al., "Stable dye–DNA intercalation complexes as reagents for high–sensitivity fluorescence detection", Nature, 359:859–861 (1992).

Goldkorn et al., "A simple and efficient enzymatic method for covalent attachment of DNA to cellulose. Application for hybridization–restriction analysis and for in vitro synthesis of DNA probes", Nucl. Acids Res., 14(22): 9171–9191 (1986).

Green, M., "AVIDIN", Advances in Protein Chemistry, (Avidin, Ed.) Academic Press, New York, NY, pp. 85–133 (1975).

Gromova et al., "DNA Duplexes wit Phosphoamide Bonds: The Interaction with Eco RII and Sso Restriction Endonucleases," Bioorg. Khim., 13(2):269–272 (1987) [Article in Russian, English abstract on last page of article].

Gyllensten, "PCR and DNA Sequencing", BioTechniques, 7(7):700–708 (1989).

Hata et al., "A New Method for the Synthesis of 5'–Amino–Nucleosides and Their Phosphoramidate Derivatives", Chem. Lett., 601–604 (1976).

Hegner et al., "Immobilizing DNA on gold via thiol modification for atomic force microspcopy imaging in buffer solutions", FEBS Letters, 336(3):452–456 (1993).

Hegner et al., "Ultralarge atomically flat template–stripped Au surfaces for scanning probe microscopy", Surface Sci., 291:39–46 (1993).

Hillenkamp, "Laser Desorption Mass Spectrometry: Mechanisms, Techniques and Applications", Adv. Mass Spectrometry, 11A:354–362 (1988).

Hobbs, "Nucleotides and Nucleic Acids", Organophosphorous Chem., 21:201–321 (1990).

Khrapko et al., "A method for DNA sequencing by hybridization with oligonucleotide matrix", DNA Sequence, 1:375–388 (1991).

Koole et al., "A novel synthetic approach to phosphate–methylated DNA oligomers using 9–fluorenylmethoxycarbonyl (Fmoc) as temporary base amino protecting group", Proc. K. Ned. Akad. Wet., B91(2):205–209 (1988).

Kremsky et al., "Immobilization of DNA via oligonucleotides containing an aldehyde or carboxylic acid group at the 5' terminus", Nucl. Acids Res., 15(7):2891–2909 (1987).

Kusukawa et al., "Rapid and Reliable Protocol for Direct Sequencing of Material Amplified by the Polymerase Chain Reaction", BioTechniques, 9(1):66–72 (1990).

Longo et al., "Use of uracil DNA glycosylase to control carry–over contamination in polymerase chain reactions", Gene, 93:125–128 (1990).

Mag et al., "Synthesis and selective cleavage of an oligodeoxynucleotide containing a bridged internucleotide 5'–phosphorothioate linkage", Nucl. Acids Res., 19(7):1437–1441 (1991).

Maskos et al., "Oligonucleotide hybridisations on glass supports: a novel linker for oligonucleotide synthesis and hybridisation properties of oligonucleotides synthesised in situ", Nucl. Acids Res., 20(7):1679–1684 (1992).

McBride et al., "An Investigation of Several Deoxynucleoside Phosphoramidites Useful for Synthesizing Deoxyoligonucleotides", Tetrahedron Lett., 24(3):245–248 (1983).

Miller et al., "Synthesis and Properties of Adenine and Thymine Nucleoside Alkyl Phosphotriesters, the Neutral Analogs of Dinucleoside Monophosphates", J. Am. Chem. Soc., 93:6657–6665 (1971).

Moody et al., "Regiospecific inhibition of DNA duplication by antisense phosphate methylated oligodeoxynucleotides", Nucl. Acids Res., 17(12):4769–4782 (1989).

Nadjii et al., "Photochemically and Photoenzymatically Cleavable DNA", J. Am. Chem. Soc., 114:9266–9269 (1992).

Nakamaye et al., "Direct sequencing of polymerase chain reaction amplified DNA fragments through the incorporation of deoxynucleoside α–thiotriphosphates", Nucl. Acids Res., 16(21):9947–9959 (1988).

Nelson et al., "Volatilization of High Molecular Weight DNA by Pulsed Laser Ablation of Frozen Aqueous Solutions", Science, 246:1585–1587 (1989).

Ogilvie et al., "Synthesis of the Thymidine Dinucleotide Analogue Containing an Internucleotide Silyl Linkage", Tetrahedron Lett., 26(35):4159–4162 (1985).

Olsen et al., "Direct Sequencing of Polymerase Chain Reaction Products", Methods Enzymol., 218:79–92 (1993).

Saha et al., "Disopropylsilyl–Linked Oligonucleotide Analogs: Solid–Phase Synthesis and Physicochemical Properties", J. Org. Chem., 58:7827–7831 (1975).

Saiki et al., "Genetic analysis of amplified DNA wih immobilized sequence–specific oligonucleotide probes", Proc. Natl. Acad. Sci. USA, 86:6230–6234 (1989).

Sanger et al., "A Rapid Method for Determining Sequences in DNA by Primed Synthesis with DNA Polymerase", J. Mol. Biol., 94:441–448 (1975).

Schmidt et al., "Phylogenetic Identification of Uncultured Pathogens Using Ribosomal RNA Sequences", Methods Enzymol., 235:205–222 (1994).

Seliger et al., "Oligonucleotide Analogues with Dialkyl Silyl Internucleoside Linkages", Nucleosides Nucleotides, 6(1&2):483–484 (1987).

Smith, A., "DNA Sequence Analysis by Primed Synthesis", Methods Enzymol., 65:560–580 (1980).

Southern et al., "Analyzing and Comparing Nucleic Acid Sequences by Hybridization to Arrays of Oligonucleotides: Evaluation Using Experimental Models", Genomics, 13:1008–1017 (1992).

Sproat et al., "The synthesis of protected 5'mercapto–2', 5'–dideoxyribonucleoside–3'–O–phosphoramidites; uses of 5'–mercapto–oligodeoxyribonnucleotides", *Nucl. Acids Res.*, 15:4837–4848 (1987).

Szczylik et al., "Selective Inhibition of Leukemia Cell Proliferation by BCR–ABL Antisense Oligodeoxynucleotides", *Science*, 253:562–565 (1991).

Szbalski, W. "Universal restriction endonucleases: designing novel cleavage specificities by combining adapter oligodeoxynucleotide and enzyme moieties", *Gene*, 40:169–173 (1985).

Tomasz et al., "On the Stability of Phospodiester–Amide Internucleotide Bond", *Tetrhyedron Lett.*, 22(39):3905–3908 (1981).

Townsend et al., (Eds.), *Nucleic Acid Chemistry: Improved and New Synthetic Procedures, Methods and Techniques*, John Wiley and Sons, New York, NY, p. 337 (1986).

Van Ness et al., "A versatile solid support system for oligodeoxynucleotide probe–based hybridization assays", *Nucl. Acids Res.*, 19(12):3345–3350 (1991).

Watson et al., "Chapter 27: DNA–Based Diagnosis of Genetic Diseases", *Recombinant DNA*, Second Edition, Scientific American, Inc. (1992).

Wu et al., "Matrix–assisted Laser Desorption Time–of–flight Mass Spectrometry of Oligonucleotides Using 3–Hydroxypicolinic Acid as an Ultraviolet–sensitive Matrix", *Rapid Comm. Mass Spectrometry*, 7:142–146 (1993).

Yamamoto et al., "One–step Synthesis of 5'–Azido–nucleosides", *J. Chem. Soc., Perkin trans.*, 11:306–310 (1980).

Youngquist et al., "Matrix–assisted Laser Desorption Ionization for Rapid Determination of the Sequences of Biologically Active Peptides Isolated from Support–bound Combinatorial Peptide Libraries", *Rapid Comm. Mass Spectrometry*, 8:77–81 (1994).

Zhang et al., "Single–base mutational analysis of cancer and genetic diseases using membrane bound modified oligonucleotides", *Nucl. Acids Res.*, 19(14):3929–3933 (1991).

Matthews, et al., "Analytical Strategies for the Use of DNA Probes" *Analytical Biochemistry* 169, 1–25 (1988).

Tong and Smith, "Solid phase purification in automated DNA sequencing," J.DNA Seq. and Mapping, 4:151–162, 1993.

Bahr et al., "Analysis of biopolymers by matrix–assisted laser desorption/ionization (MALDI) mass spectrometry," *Fresenius J. Anal. Chem.*, 348:783–791, 1994.

Barinaga, "Protein chemists gain a new analytical tool," *Science*, 246:32–33, 1989.

Brummel et al., "A mass spectrometric solution to the address problem of combinatorial libraries," *Science*, 264:399, 1994.

Fitzgerald et al., "The analysis of mock DNA sequencing reactions using matrix–assisted laster despoption/ionization mass spectrometry," *Rapid Comm. in Mass Spectrom.*, 7:895–897, 1993.

Goldkorn and Procktop, "A simple and efficient enzymatic method for covalent attachment of DNA to cellulose: Application for hybridization–restriction analysis and for in vivo synthesis of DNA probes," *Nuc. Acids. Res.*, 14:9171, 1986.

Hettich and Buchanan, "Determination of oligonucleotide sequences and modifications by laser desorption fourier transform mass spectrometry," *Abst. Pap. Am. Chem. Soc.*, 200:1–2, Abstract #105, 1990.

Hillenkamp and Karas, "Matrix assisted UV–laser desorption/ionization: a new approach to mass spectrometry of large biomolecules" In: *Biological Mass Spectrometry*, Burlingame and McCloskey (eds.), Elsevier Science Publishers B.V. Amsterdam, Holland, 1988.

Hillenkamp and Karas, "Laser desorption ionization of proteins with molecular masses exceeding 10,000 daltons," *Anal. Chem.*, 60:2299–2301, 1988.

Hillenkamp and Karas, "Matrix laser desorption of very large organic molecules," In: *Mass Spectrometry of Large Non–Volatile Molecules for Marine Organic Chemistry*, Hilf and Tuszynski (Eds.), World Scientific Publishers, Singapore, 1990.

Lay, Jr. et al., "Detection and characterization of DNA adducts at the femtomole levl by desorption ionization mass spectrometry," *Environ. Health Perspect.*, 99:191–193, 1993.

Mag et al., "Synthesis and selective cleavage of an oligodeoxynucleotide containing a bridged internucleotide 5'–phosphorothiate linkage," *Nuc. Acids Res.*, 19(7):1437–1441, 1991.

Maskos and Southern, "Oligonucleotide hybridisations on glass supports: A novel linker for oligonucleotide synthesis and hybridisation properties of oligonucleotides synthesis in situ," *Nc. Acids Res.*, 20(7):1679–1684, 1992.

Nadji et al., "Photochemically and photoenzymatically cleavable DNA," *J. Am. Chem.*, 114:9266–9269, 1992.

Nordhoff et al., "Matrix–assisted laser desorption/ionization mass spectrometry of nucleic acids with weavelengths in the ultraviolet and infrared," *Rapid Comm. in Mass Spectrom.*, 6:771–776, 1992.

Parr et al., "Matrix–assisted laser desorption/ionization mass spectrometry of synthetic ologideoxyribonucleotides," *Rapid Comm. in Mass Spectrom.*, 6:369–372, 1992.

Podhajska and Szybalski, "Conversion of the Fok I endonuclease to a universal restriction enzyme: cleavage of phage M13mp7 DNA at predetermined sites," *Gene*, 40:175–182, 1985.

Silveira and Orgel, "PCR with detachable primers," *Nuc. Acids Res.*, 23(6):1083–1084, 1995.

Stemmler et al., "Matrix–assisted laser desorption/ionization fourier–transform mass spectrometry of oligodeoxyribonucleotides," *Rapid Comm. in Mass Spectrom.*, 7:828–836, 1993.

Szybalski, "Universal restriction endonuclease: designing novel cleavage specificities by combining adapter oligodeoxynucleotide and enzyme moieties," *Gene*, 40:169–173, 1985.

Tang et al., "Mass spectrometry of laser–desorbed oligonucleotides," *Rapid Comm. in Mass Spectrom.*, 6:365–368, 1992.

Tang et al., "Laser mass spectrometry of oligonucleotides with isomer matrices," *Rapid Comm. in Mass Spectrom.*, 7:435–439, 1993.

Wu et al., "Matrix–assisted laser desorption time–of–flight mass spectrometry of oligonucleotides using 3–hydroxypicolinic acid as an ultraviolet–sensitive matrix," *Rapid Comm. in Mass Spectrom.*, 7:142–146, 1993.

Wu et al., "Time–of–flight mass spectrometry of underivatized single–stranded DNA oligomers by matrix–assisted laser desportion," *Anal. Chem.*, 66:1637–1645, 1994.

Youngquist et al., "Matrix–assisted laser desorption ionization for rapid determination of the sequences of biologically active peptides isolated from support–bound combinatorial peptide libraries," *Rapid Comm. in Mass Spectrom.*, 8:77–81, 1994.

Frohman, "Cloning PCR products," Chapter 2 in *The Polymerase Chain Reaction* (Mullis et al., (ed), Birkhauser, Boston, pp. 14–37, 1994.

Wu et al., "The ligation amplification reaction (LAR)— amplification of specific DNA sequences using sequential rounds of template–dependent ligation," *Genomics*, 4(4):560–569, 1989.

Nakamaye et al., "Direct sequencing of polymerase chain reaction amplified DNA fragments through the incorporation of deoxynucleoside a–thiothiphosphates," *Nuc. Acids Res.*, 16(21):9947–9959, 1988.

* cited by examiner

Biotin ∼∼∼ Streptavidin    Fig. 2L

| TYPE OF HEMOGLOBIN | AMINO ACID SEQUENCE AND DNA NUCLEOTIDE SEQUENCE |
|---|---|
| A | -Pro-Glu-Glu<br>-CCT-G<u>A</u>G-GAG- |
| B | -Pro-Val-Glu<br>-CCT-G<u>T</u>G-GAG- |

Fig. 7A

| CONDITION | AMINO ACID SEQUENCE AND DNA NUCLEOTIDE SEQUENCE |
|---|---|
| NORMAL | 342<br>-Thr-Ile-Asp-Glu-Lys-Gly-Thr-<br>-ACC-ATC-GAC-<u>G</u>AG-AAA-GGG-A... |
| $\alpha_1$-ANTITRYPSIN DEFICIENT | -Thr-Ile-Asp-Lys-Lys-Gly-Thr-<br>-ACC-ATC-GAC-<u>A</u>AG-AAA-GGG-A... |

Fig. 7B

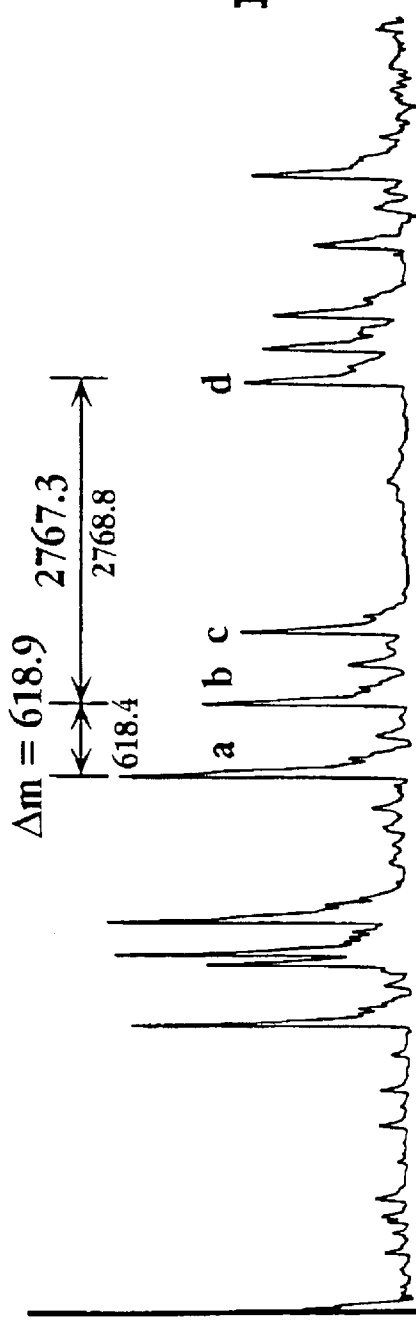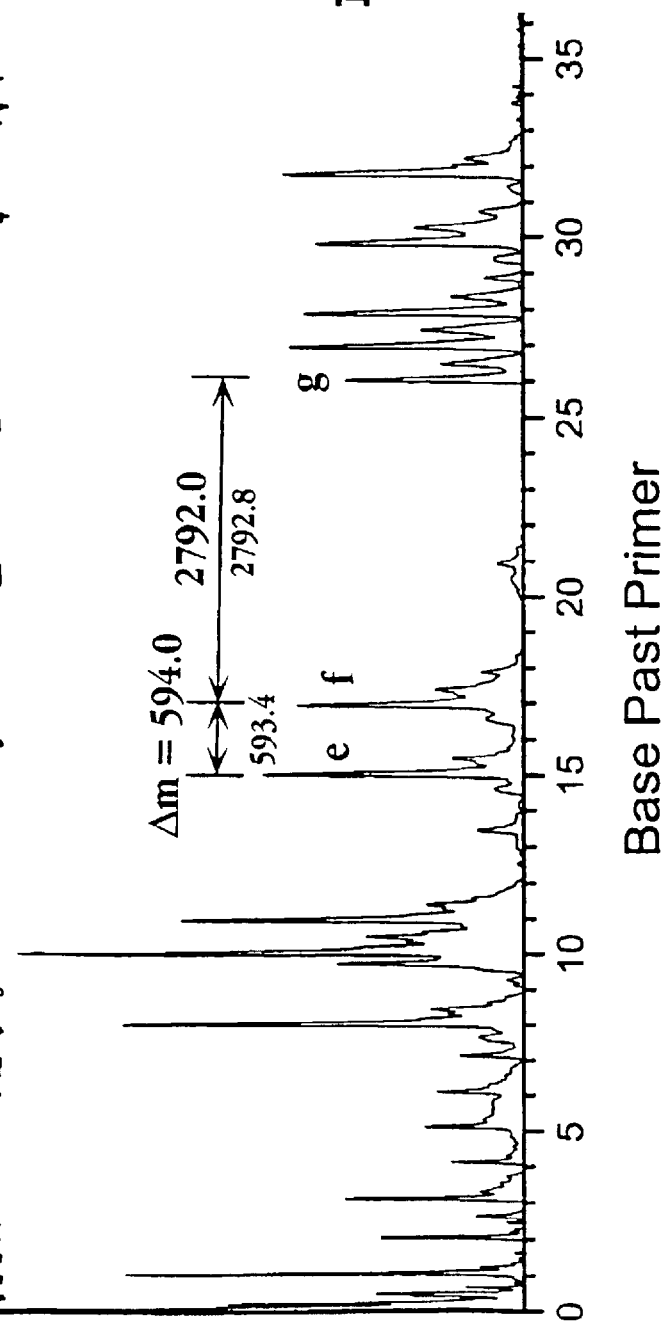
Fig. 14A
Fig. 14B

PRIMER 1

PRIMER 2

(a)

(b)

PRIMER 1 PRODUCT

PRIMER 2 PRODUCT

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 9..10
        (D) OTHER INFORMATION: /note= "sequence contains
            phosphoramidate bond between nucleotides 9 and 10"

(xi) SEQUENCE DESCRIPTION: SEQ ID NO:1:

TTCATGCAAT CCGATG                                                    16

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 16..17
        (D) OTHER INFORMATION: /note= "primer containing a first
            region with an immobilization attachment site, a
            cleavable site "x" between nucleotides 16 and 17"

(xi) SEQUENCE DESCRIPTION: SEQ ID NO:2:

ACTCCTGTGG AGAACTCTGC                                                20

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GCAGAGTTCT CCACAGGAGT                                              20

(2) INFORMATION FOR SEQ ID NO:4:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

ACTCCTGTGG AGAACT                                                  16

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

ACCATCGACG AGAAAGGGA                                               19

(2) INFORMATION FOR SEQ ID NO:6:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

Thr Ile Asp Glu Lys Gly Thr
1               5

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

ACCATCGACA AGAAAGGGA                                               19

(2) INFORMATION FOR SEQ ID NO:8:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:8:

```
Thr Ile Asp Lys Lys Gly Thr
1               5
```

(2) INFORMATION FOR SEQ ID NO:9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 7..15
        (D) OTHER INFORMATION: /note= "N = G, A, C or T"

(xi) SEQUENCE DESCRIPTION: SEQ ID NO:9:

ACGACANCCA TGCANCACC                                19

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 9..10
        (D) OTHER INFORMATION: /note= "probe contains a cleavable
            ribose at position 10 from 5' end (position 7 from 3'
            end)"

(xi) SEQUENCE DESCRIPTION: SEQ ID NO:10:

AAATACATCG CTTGAAC                                  17

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 9..10
        (D) OTHER INFORMATION: /note= "18-mer is biotinylated at
            5' end and contains a ribose at position 10 from 5' end"

(xi) SEQUENCE DESCRIPTION: SEQ ID NO:11:

ATCTTCCTGG CAAACTCA                                18

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 17..18
        (D) OTHER INFORMATION: /note= "reverse primer contains a

```
            5'-(S)thymidine at position 18"

(xi) SEQUENCE DESCRIPTION: SEQ ID NO:12:

CACACAGGAA ACAGCTATGA CC                                          22

(2) INFORMATION FOR SEQ ID NO:13:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: misc_feature
         (B) LOCATION: 16..17
         (D) OTHER INFORMATION: /note= "intermediary
             oligonucleotide is biotinylated at 3' end"

(xi) SEQUENCE DESCRIPTION: SEQ ID NO:13:

TAGCTGTTTC CTGTGTG                                                17

(2) INFORMATION FOR SEQ ID NO:14:

(i) SEQUENCE CHARACTERISTICS:
         (A) LENGTH: 73 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: misc_feature
         (B) LOCATION: 51..68
         (D) OTHER INFORMATION: /note= "priming region corresponds
             to nucleotides 51-68; C and G of interest at positions 35
             and 32, respectively"

(xi) SEQUENCE DESCRIPTION: SEQ ID NO:14:

CAGCTTTTGT TCCCTTTAGT GAGGGTTAAT TGCGCGCTTG GCGTAATCAT GGTCATAGCT    60

GTTTCCTGTG TGA                                                      73

(2) INFORMATION FOR SEQ ID NO:15:

(i) SEQUENCE CHARACTERISTICS:
         (A) LENGTH: 73 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: misc_feature
         (B) LOCATION: 51..68
         (D) OTHER INFORMATION: /note= "priming region corresponds
             to nucleotides 51-68; mutations at positions 35 (A) and
             32 (T)"

(xi) SEQUENCE DESCRIPTION: SEQ ID NO:15:

CAGCTTTTGT TCCCTTTAGT GAGGGTTAAT TTCGAGCTTG GCGTAATCAT GGTCATAGCT    60

GTTTCCTGTG TGA                                                      73

(2) INFORMATION FOR SEQ ID NO:16:

(i) SEQUENCE CHARACTERISTICS:
```

(A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 13..14
        (D) OTHER INFORMATION: /note= "primer is biotinylated at
            5' end and contains a 5' (S)- thymidine at position 14"

(xi) SEQUENCE DESCRIPTION: SEQ ID NO:16:

CAGGAAACAG CTATGACC                                                     18

(2) INFORMATION FOR SEQ ID NO:17:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

ATGATTACGC CAAGCGCGCA ATTAACCCTC ACTAAAGGGA ACAAA                        45

(2) INFORMATION FOR SEQ ID NO:18:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

ATGATTACGC CAAGCTCGAA ATTAACCCTC ACTAAAGGGA ACAAA                        45

(2) INFORMATION FOR SEQ ID NO:19:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 7..8
        (D) OTHER INFORMATION: /note= "the primer contains a 1:1
            mixture of dT and dG incorp. at positions 7 and 15"

(xi) SEQUENCE DESCRIPTION: SEQ ID NO:19:

ACGACATCCA TGCATCACC                                                    19

PRIMERS USEFUL FOR SIZING NUCLEIC ACIDS

The present application is a continuation-in-part of U.S. patent application Ser. No. 08/639,363 filed Apr. 26, 1996, allowed, now U.S. Pat. No. 5,830,655 which is a continuation-in-part of U.S. patent application Ser. No. 08/445,751 filed May 22, 1995 which has since issued as U.S. Pat. No. 5,700,642. The entire text of each of the above-referenced disclosures is specifically incorporated by reference herein without disclaimer.

1.0 BACKGROUND OF THE INVENTION

1. Field of the Invention

The present invention relates to oligonucleotide compositions containing cleavable primers and diagnostic and analytical methods employing such primers.

2. Description of Related Art

DNA, the primary genetic material, is a complex molecule consisting of two intertwined polynucleotide chains, each nucleotide containing a deoxyribose unit, a phosphate group and a nitrogenous heterocyclic base. The two polynucleotide strands are held together via hydrogen bonding interactions between complementary base pairs. A normal human being possesses 23 pairs of chromosomes containing a total of about 100,000 genes. The length of DNA contained within the human chromosomes totals about 3.3 billion base pairs, with a typical gene containing about 30,000 base pairs.

Approximately 4,000 human disorders are attributed to genetic causes. Hundreds of genes responsible for various disorders have been mapped, and sequence information is being accumulated rapidly. A principal goal of the Human Genome Project is to find all genes associated with each disorder. The definitive diagnostic test for any specific genetic disease (or predisposition to disease) will be the identification of polymorphic variations in the DNA sequence of affected cells that result in alterations of gene function. Furthermore, response to specific medications may depend on the presence of polymorphisms. Developing DNA (or RNA) screening as a practical tool for medical diagnostics requires a method that is inexpensive, accurate, expeditious, and robust.

Due to the vast amount of genetic information yet to be gathered in both human and non-human genomes, intense efforts are underway to develop new and faster methods of DNA analysis, including DNA detection, sizing, quantification, sequencing, gene identification, and the mapping of human disease genes. Efforts to analyze DNA have been greatly aided by the development of a process for in vitro amplification of DNA, namely, the polymerase chain reaction (PCR™). PCR™ provides the ability to amplify and obtain direct sequence information from as little as one copy of a target DNA sequence.

Typically, PCR™ amplification is carried out by placing a mixture of target double-stranded DNA, a mixture of deoxynucleotide triphosphates, buffer, two primers (one phosphate-labeled) and DNA polymerase (e.g., heat stable Taq polymerase) in a thermocycler which cycles between temperatures for denaturation, annealing, and synthesis. The selection of primers defines the region to be amplified. In the first stage of the cycle, the temperature is raised to separate the double stranded DNA strands to form the single-stranded templates for amplification. The temperature is then lowered to generate the primed templates for DNA polymerase. In a third stage, the temperature is raised to promote Taq-promoted DNA synthesis, and the cycle of strand separation, annealing of primers, and synthesis is repeated for about as many as 30–60 cycles. Standard detection, sizing, and sequencing methods as described above, while providing useful information,. are often tedious and costly. Many of the commonly employed techniques involve multiple handling steps. Further, the most common method of fragment analysis—gel electrophoresis—is a relatively time-consuming process.

Oligonucleotide sizing and sequence analysis is typically carried out by first utilizing either the enzymatic method developed by Sanger and Coulson, or by chemical degradation, developed by Maxam and Gilbert. The Sanger method uses enzymatic chain extension coupled with chain-terminating dideoxy- precursors to produce randomly terminated DNA fragments. The Maxam and Gilbert technique involves four different base-specific reactions carried out on portions of the DNA target to produce four sets of radiolabeled fragments. Both techniques utilize gel electrophoresis to separate resultant DNA fragments of differing lengths.

In conventional DNA analysis, the DNA fragments are labeled with radioisotopes. After separation on sequencing gels, the fragments are visualized by the image they generate upon a piece of film applied to the gel.

Other methods of DNA analysis have been described which eliminate the use of radioisotopes. One example of such a method uses fluorophores or fluorescent tags. In general, four different fluorophores, each having a different absorption and emission spectrum, are attached to the DNA primers using chemical DNA synthesis techniques. Primers with different fluorescent labels are used in each of the four enzymatic sequencing reactions. In an alternate approach to the four dye fluorescence-based detection, a dye is chemically attached to a chain-terminating base analog after enzymatic extension. In this approach, synthesis of the different dye-primers is avoided. Mono- and poly- functional intercalator compounds have also been developed as reagents for high-sensitivity fluorescence detection (Glazer et al., 1992). These planar aromatic fluorophores (e.g., ethidium homodimer, thiazole orange homodimer, oxazole yellow homodimer) insert between adjacent base pairs of double stranded DNA.

Although the efficiency of these processes has been improved by automation, faster and cheaper methods must still be developed to efficiently carry out large-scale DNA analyses. The advantages of using mass spectrometry for analyzing DNA include a dramatic increase in both the speed of analysis (a few seconds per sample) and the accuracy of direct mass measurements. In contrast, electrophoretic methods require significantly longer lengths of time (minutes to hours) and can only measure the size of DNA fragments as a function of relative mobility to comigrating standards. Gel-based separation systems also suffer from a number of artifacts that reduce the accuracy of size measurements. These mobility artifacts are related to the specific sequences of DNA fragments and the persistence of secondary and tertiary structural elements even under highly denaturing conditions.

The inventors have performed significant work in developing time-of-flight mass spectrometry ("TOF-MS") as a means for separating and sizing DNA molecules, although other forms of mass spectrometry can be used and are within the scope of this invention. Balancing the throughput and high mass accuracy advantages of TOF-MS is the limited size range for which the accuracy and resolution necessary for characterizing DNA by mass spectrometry is available. Current state of the art for TOF-MS offers single nucleotide resolution up to ~100 nucleotides in size and four nucleotide resolution up to ~160 nucleotides in size. These numbers are expected to grow as new improvements are developed in the mass spectrometric field.

Existing gel-based protocols for the analysis of DNA often do not work with TOF-MS because the PCR™ product size range, typically between 100 and 800 nucleotides, is outside the current resolution capabilities of TOF-MS. Application of DNA analysis to TOF-MS requires the development of new primer sets that produce small PCR™ products 50 to 160 nucleotides in size, preferably 50 to 100 nucleotides in size.

Gel-based systems are capable of multiplexing the analysis of 2 or more DNA sequences contained at multiple loci using two approaches. The first approach is to size partition the different PCR™ product loci. Size partitioning involves designing the PCR™ primers used to amplify different loci so that that the allele PCR™ product size range for each locus covers a different and separable part of the gel size spectrum. As an example, the PCR™ primers for Locus A might be designed so that the allele size range is from 250 to 300 nucleotides, while the primers for Locus B are designed to produce an allele size range from 340 to 410 nucleotides.

The second approach to multiplexing 2 or more DNA sequences contained at different loci on gel-based systems is the use of spectroscopic partitioning. Current state of the art for gel-based systems involves the use of fluorescent dyes as specific spectroscopic markers for different PCR™ amplified loci. Different chromophores that emit light at different color wavelengths provide the means for differential detection of two different PCR™ products even if they are exactly the same size, thus 2 or more loci can produce PCR™ products with allele size ranges that overlap. For example, Locus A with a green fluorescent tag produces an allele size range from 250 to 300 nucleotides, while Locus B with a red fluorescent tag produces an allele size range of 270 to 330 nucleotides. A scanning, laser-excited fluorescence detection device monitors the wavelength of emissions and assigns different PCR™ product sizes, and their corresponding allele values, to their specific loci based on their fluorescent color.

In contrast, mass spectrometry directly detects the molecule eliminating the need for optical spectroscopic partitioning as a means for multiplexing. Because of this direct detection, MS also allows for improved accuracy in DNA analysis. MS also lends itself to high-throughput, highly-automated processes for analyzing DNA. Therefore, new methods and primers are needed in order to employ mass spectrometry for the analysis of DNA and for multiplexed analysis.

2.0 SUMMARY OF THE INVENTION

The present invention provides an oligonucleotide composition containing a modified primer having a 5' end and a 3' end and containing at least one selectively cleavable site. Preferably, the cleavable site is located at or within about five nucleotides from the 3' end of the primer.

The modified oligonucleotide primer which has a 5' end and a 3' end, is composed of two separate nucleotide regions. The first region contains the 5' end, while the second region contains the 3' end of the primer, where the 3' end is capable of serving as a priming site for enzymatic extension, typically by a polymerase or ligase. The second region also contains a cleavable site which connects the first and second primer regions. In a preferred embodiment, the first region of the primer contains at least three nucleotides. The first primer region may optionally contain one or more secondary cleavable sites, located between the 5' end of the primer and the second region cleavable site (e.g., to breakdown the first region into smaller fragments). For a modified primer containing a secondary cleavable site, the furthest downstream cleavable site should ideally be cleaved with near 100% efficiency, to avoid the formation of secondary or shadow products with additional bases.

In one embodiment of the invention, the cleavable site is located at or within about five nucleotides from the 3' end of the primer. In an alternate embodiment, the second primer region consists of a single nucleotide that also contains the cleavable site, such as a ribonucleotide. The second region may alternatively be composed of only the cleavable site.

The chemically cleavable site may be a modified base, a modified sugar, or a chemically cleavable group incorporated into the phosphate backbone of the primer, such as phosphorothioate or other chemically cleavable linkages. Cleavable sites contained within the modified primer composition include chemically cleavable groups such as dialkoxysilane, 3'-(S)-phosphorothioate, 5'-(S)-phosphorothioate, 3'-(N)-phosphoramidate, 5'-(N)-phosphoramidate, and ribose.

Additional cleavable sites include nucleotides cleavable by an enzyme such as a nuclease. In one embodiment, the cleavable site within the modified primer composition is a single uracil incorporated to replace a thymine, where the uracil is cut site-specifically by treatment with uracil DNA-glycosylase, followed by alkali treatment. In another embodiment, the cleavable site is a restriction endonuclease cleavable site, where the recognition sequence is located in the first primer region (i.e., upstream of the cleavage site). In a preferred embodiment, the restriction endonuclease cleavable site is located at or within about five nucleotides from the 3' end of the primer. It is also possible, such as with class IIs restriction enzymes, to position the cleavable site or cut site within the extension product. Restriction endonucleases for use in cleaving the modified primers of the invention include class IIs restriction endonucleases such as BpmI, BsgI, BseRI, BsmFI, and FokI. A modified primer including a BpmI or BsgI recognition site contains (i) a first region containing the recognition site, 5'-CTGGAG-3'or 5'-GTGCAG-3', respectively, and (ii) located 16 bases downstream from the last nucleotide of the recognition sequence, in the second primer. region, is the cleavable site. A modified primer containing a BseRI or BsmFI recognition site, e.g., 5'-GAGGAG-3', or 5'-GGGAC-3, respectively, contains a cleavable site located 10 bases downstream from the last nucleotide of the recognition sequence, while a primer containing a FokI recognition sequence (e.g., 5'-GGATG-3') possesses a cleavable site 9 bases downstream from the last nucleotide of the recognition sequence.

In a yet another embodiment, the cleavable site is a restriction endonuclease cleavable site, where the recognition sequence is located in the first primer region (i.e., upstream of the cleavage site), and the first primer region contains a 5' hairpin-type (self-complementary double stranded) domain. The 5' hairpin domain includes the double stranded recognition site for the restriction enzyme. The second (single stranded) primer region contains (i) the cleavable site (i.e. restriction endonuclease cut site), and (ii) is composed of nucleotides complementary to a single stranded target, thus serving as a priming site for enzymatic extension. Following enzymatic extension of the primer, the product is cleaved by treatment with a suitable class IIS restriction endonuclease, followed by denaturation to release the single stranded extension segment.

In another embodiment, the cleavable site is a nucleotide or series of nucleotides capable of blocking or terminating 5' to 3' enzyme-promoted digestion by an enzyme having 5' to 3' exonuclease activity, such as T7 Gene 6 Exonuclease or a phosphodiesterase such as that derived from calf spleen. Blocking nucleotides include peptide nucleic acids and nucleotides containing a phosphorothioate, methyl phosphonate or borano-phosphate group. Modifications at the 3' position of the sugar also may block the digestion by an exonuclease. In a primer extension reaction utilizing a modified primer containing a blocking nucleotide as the cleavable site, following a primer extension reaction, the resulting product, composed of (i) a modified primer containing a blocking nucleotide, and (ii) an extension segment, is treated with a nuclease such as an exonuclease having a 5' to 3' exonuclease activity. Nuclease treatment typically results in digestion of the first region of the primer to generate an extension segment composed of nucleotides downstream (i.e. 3') of the cleavable site. Preferably, the blocking group does not inhibit enzymatic extension of the primer.

The modified primer may further include an immobilization attachment site for binding to a solid support. The immobilization attachment site may be located either upstream (i.e. 5' to) or downstream (i.e. 3' to) of the cleavable site. In one embodiment, the immobilization attachment site is located at the 5' end or 5' relative to the cleavable site (i.e. upstream of the cleavable site) of the modified primer. In another embodiment, the immobilization attachment site is located at the 3' end or 3' relative to the cleavable site (i.e. downstream of the cleavable site). Alternatively, the immobilization attachment site may be contained within the extension segment resulting from an enzymatic extension reaction, or, may be contained within a target nucleic acid.

For modified primers including an immobilization attachment site, the primer is attachable to a solid support by either a covalent or non-covalent linkage between the solid support and the primer immobilization attachment site to provide an immobilized modified oligonucleotide composition. Solid supports for use in the present invention include glass, silicon, polystyrene, cellulose, teflon, polystyrene divinyl benzene, aluminum, steel, iron, copper, nickel, silver and gold.

In one embodiment, the primer is attachable to a solid support via an intervening spacer arm, with a typical spacer being six or more atoms in length.

In another embodiment, the modified primer contains an immobilization attachment site in the first primer region composed of a series of bases complementary to an intermediary oligonucleotide. The modified primer is immobilized by specific hybridization of the immobilization attachment site to the intermediary oligonucleotide, which is bound to a solid support. The intermediary oligonucleotide can be complementary to all or a portion of the sequence of the modified primer. The intermediary nucleotide is typically composed of 6 or more bases, and preferably more than 8 bases. Additionally, the intermediary oligonucleotide may also be homologous to a region within target nucleic acid (template) molecule.

In one embodiment, the modified primers of the present invention are oligonucleotides, such as DNA or RNA, having phosphodiester internucleotide linkages. In another embodiment, the modified primers are oligonucleotide analogues composed of alternative backbone structures containing internucleotide linkages such as methylphosphonate, phosphotriester, phosphorothioate, peptide, and the like. Primers for use in the invention should be capable of hydrogen bonding in a sequence-specific manner to a target sequence.

The invention also provides a method for determining the size of a primer extension product using the modified primers of the present invention. In employing the method, oligonucleotide size analysis is carried out by first contacting a modified primer of the present invention with a target nucleic acid molecule (e.g. DNA or RNA) to effect hybridization of the primer with the single stranded target. The modified primer is complementary to the target and contains a first region containing the 5' end of the primer, and a second region containing the 3' end of the primer, where the 3' end is capable of serving as a priming site for enzymatic extension. The second region of the primer also contains a cleavable site.

In determining the size of a primer extension product, the primer is extended by enzymatic means, typically by action of a polymerase or ligase, to generate a mixture containing a product composed of the primer and one more extension segments. The resulting product is cleaved at the cleavable site and the resulting extension segment is then sized by any of a number of suitable analytical techniques, preferably mass spectrometry. In accordance with the invention, the mass of the extension segment is decreased and the read length of the extension segment is increased relative to the read length of the product composed of the modified primer and the extension segment.

In a preferred embodiment for determining the size of an extension product, the modified primer (first or second region) or template is immobilized by attachment to a solid support. Immobilization may be via a covalent or non-covalent linkage. Exemplary non-covalent linkages include ligand-protein interactions and base-specific hydrogen bonding. The extension segment from an enzymatic extension reaction can also be immobilized by attachment to a solid support, and is released from the solid support prior to sizing or sequence determination. In the latter embodiment, enzymatic extension is typically carried out in the presence of a nucleotide containing (i) an immobilization attachment site and (ii) a releasable site, such as the exemplary nucleotide, biotinylated-disulfide-dideoxynucleotide. Following enzymatic extension, for example, with a ligase or polymerase, the extension product is immobilized, denatured, and cleaved at the cleavable site, leaving the extension segment affixed to the solid support. Released primer (the portion upstream of the cleavable site), template and additional mixture components are typically removed by washing, and the immobilized extension segment is then cleaved at the releasable site, to release the extension segment for sizing.

In one embodiment of the method, the modified primer is immobilized via specific hybridization of the immobilization attachment site to an intermediary oligonucleotide which is bound to a solid support (solid phase bound intermediary oligonucleotide, SPBIO). In one particular embodiment, the immobilization attachment site is located in the first primer region and is composed of a series of bases complementary to the intermediary oligonucleotide. Alternatively, if a portion of the sequence of the extension product is known, the immobilization attachment sight may be contained within a region of the extension segment.

In yet another embodiment, the SPBIO is homologous to a target nucleic acid molecule, resulting in a competition between the SPBIO and the target for hybridizing to the modified primer. Following enzymatic extension, the product (composed of the primer and an extension segment) is attached to a solid support via hybridization to the SPBIO. To promote hybridization of the SPBIO to the product, the amount of target molecule may be reduced either by (i) carrying out a target-selective digestion which leaves the primer and extension product intact, or (ii) reducing the amount of target molecule. Template specific digestion may be chemical or enzymatic.

In a related embodiment of the method, the modified primer is immobilized via hybridization to a SPBIO, where the first primer region contains a first portion which is complementary to the SPBIO, and downstream or 3' of this portion of the first region is a second portion of the first primer region which complementary to the target molecule but is not complementary to the SPBIO. The first portion of the first region of the modified primer will typically be composed of at least six or more nucleotides which are complementary to the SPBIO.

Alternatively, indirect immobilization of the modified primer can be accomplished by carrying out an enzymatic extension reaction with a target nucleic acid which is attached to a solid support. The target molecule can be immobilized either prior to or subsequent to primer extension.

Optionally, the reaction mixture containing immobilized and non-immobilized species is washed prior to cleavage at the cleavable site allowing ready separation of immobilized versus non-immobilized species prior to sizing of the extension segments.

The primer can be immobilized at the immobilization attachment site either prior to or after enzymatic extension, depending upon the nature of immobilization. Generally, when the immobilization attachment site is contained within the first primer region, the immobilization attachment remains intact under the selected cleavage conditions to retain a significant portion of nucleotides from the modified primer (e.g., those comprising the first primer region) in immobilized form. In accordance with the present method, the read length of the extension segment resulting from cleavage at the cleavable site is increased relative to the read length of the product composed of the primer and the extension segment.

In one embodiment of the invention, the extension segments, typically containing no more than about five nucleotides derived from the modified oligonucleotide primer, are sized using mass spectrometry. Such sizing may utilize matrix-assisted laser desorption ionization mass spectrometry, and more particularly, may be accomplished using time-of-flight mass spectrometry.

The sizing method may also be coupled with amplification of a target nucleic acid.

In one embodiment of this aspect of the invention, first and second primers are combined with a target nucleic acid under conditions effective to promote the hybridization of the primers to the nucleic acid to generate primer/nucleic acid complexes. One of the primers (e.g., the first primer) is complementary to the target nucleic acid and has a first region containing the 5' end of the primer and an immobilization attachment site. The first primer further contains a second region containing the 3' end of the primer, where the 3' end is capable of serving as a priming site for enzymatic extension. The second region of the first primer further contains a cleavable site. The second primer is homologous to the target nucleic acid.

The primer/nucleic acid complexes are converted to double strand fragments in the presence of a suitable polymerase and all four deoxynucleotide triphosphates (dNTPs) or modified versions thereof. The number of primer-containing fragments is amplified by successively repeating the steps of: (i) denaturing the double strand fragments to produce single strand fragments, (ii) hybridizing the single strands with the primers to form strand/primer complexes, (iii) generating double strand fragments from the strand/primer complexes in the presence of a polymerase and all four dNTPs, and (iv) repeating steps (i) to (iii) until a desired degree of amplification has been achieved.

The amplified fragments are then denatured to generate a mixture including a product composed of the first primer and an extension segment. In one embodiment of this aspect of the invention, the amplified fragments containing the first primer are immobilized at the immobilization attachment site and the non-immobilized amplified fragments are removed, typically by washing. The first primer is then cleaved from the immobilized product at the cleavable site, causing the release of the extension segment from the support.

In an alternate embodiment, the amplified fragments may be immobilized prior to denaturing. Generally, the amplified fragments are immobilized prior to cleaving at the cleavable site, to enable release and subsequent analysis of the extension segments resulting from such cleavage, in the absence of other species (e.g., primers, reactants, excess dNTPs).

The extension segments are then sized by mass spectrometry. The read length of the extension segment is increased relative to the read length of the product composed of the first primer and the extension segment by cleavage at the cleavable site.

Another embodiment of the sizing method provides first and second primers, where one of the primers, i.e. the first primer, contains a cleavable site, and another primer, i.e. the second primer, contains an immobilization attachment site for binding to a solid support. The second primer:is composed of a 5' end and 3' end, is homologous to the target nucleic acid, and includes a first segment containing the 3' end of the second primer, and a second segment containing the 5' end of the primer and an immobilization attachment site.

These first and second primers are combined with a target nucleic acid to generate primer/nucleic acid complexes and converted to double stranded fragments in the presence of a polymerase and deoxynucleoside-triphosphates. The sizing method can be carried out using a high concentration of target nucleic acid to generate substantial amounts of primer extension product, or alternatively, may be coupled with various rounds of amplification. Upon achieving a desired amount of product, extension products containing the second primer are immobilized by attachment at the immobilization attachment site. The extension product is then cleaved at the cleavable site to generate a mixture which includes a double stranded product. Non-immobilized cleaved fragments are removed, preferably by washing, and the double stranded product is denatured to release the extension segment, which is sized by mass spectrometry, where the mass of the extension segment is decreased and the read length of the extension segment is increased relative to the read length of the primer/nucleic acid double stranded fragments. Immobilization of the extension product may occur either before or after cleavage at the cleavable site.

As will be appreciated, the cleavable site of the first primer and the immobilization attachment site of the second primer include those of the type described above.

In one embodiment, the first primer contains a class IIs restriction enzyme recognition site in the first primer region, and a cleavable site in the second primer region, and the second primer contains an immobilization attachment site for attachment to a solid support. Cleavage at the cleavable site is carried out by addition of a restriction endonuclease selective for the recognition site contained in the first primer region to provide (i) released fragments containing the first region of the first primer and (ii) a double stranded product, which is immobilized prior to denaturing to release the desired extension segment.

Also encompassed is a method for determining the size of more than one primer extension product including the steps of: (a) hybridizing a plurality of primers with more than one target nucleic acid, wherein each of said primers (i) is complementary to at least one target nucleic acid; (ii) has a first region containing the 5' end of the primer, and (iii) has a second region, containing the 3' end of the primer and a cleavable site, wherein the 3' end is capable of being extended by an enzyme; (b) extending the primers with the enzyme to generate a polynucleotide mixture containing more than one extension product; (c) cleaving more than one extension product at its respective cleavable site to release more than one extension segment, wherein the location of the cleavable site of at least two primers is selected to increase the mass difference between their respective extension segments; and (d) sizing the released extension segments by mass spectrometry (such as TOF MS), whereby said cleaving is effective to increase the read length of the extension segments relative to the read length of the products of step (b). This method may also be coupled with amplification of a target nucleic acid.

In some embodiments, the first region of at least one of said primers comprises an immobilization attachment site which may be used to immobilize one or more extension products onto a solid support. In these cases, it may be preferable to wash the extension product after said immobilizing and prior to said cleaving step.

This method may be used to size extension products of DNA or RNA target nucleic acids as well as mixtures thereof. The target nucleic acids may also be immobilized, either prior to or after said extending step.

At least one cleavable site may be a blocking nucleotide capable of blocking a 5' to 3' enzyme-promoted digestion, and wherein said cleaving is carried out by digesting the first region of at least one primer with an enzyme having a 5' to 3' exonuclease activity. At least one cleavable site may also comprise a modified base, a modified sugar, or a chemically cleavable group incorporated into the phosphate backbone. Exemplary cleavable sites include dialkoxysilane, 3'-(S)-phosphorothioate, 5'-(S)-phosphorothioate, 3'-(N) phosphoramidate, 5'-(N)phosphoramidate, uracil, and ribose.

Another aspect of this invention is a kit for analyzing at least one target nucleic acid. This kit typically includes a first primer complementary to a first target nucleic acid and a second primer complementary to an extension product of the first primer. The first primer typically has a first region containing the 5' end of the first primer and a second region containing the 3' end of the first primer and a chemically cleavable site.

These kits may be used to analyze single- and double-stranded target nucleic acids. The use of polymerase or ligase to extend nucleic acids are known in the art and one of skill in the art in light of the present disclosure would be able to select suitable primer pairs (i.e. of first and second primers) to analyze single- and double-stranded targets. For example, where double-stranded target nucleic acids are being analyzed, the first primer may typically be complementary to one strand of the target nucleic acid adjacent and upstream to the sequence one is interested in analyzing while the second primer may be complementary to the other strand adjacent and upstream from the sequence of interest. Where the target nucleic acid is single-stranded, the first and second primers may both be complementary to portions of the strand, for example, the portions flanking the sequence of interest.

Either the first or second primer or both primers may also contain an immobilization attachment site. This site is usually upstream of the chemically cleavable site and may preferably be located in the first region of the first primer. A suitable immobilization attachment site is any site capable of being attached to a group on a solid support. These sites may be a substituent on a base or sugar of the primer. An IAS may be, for example, an antigen, biotin, or digoxigenin.

The kit may also include a solid support. The solid support be is capable of being attached to the immobilization attachment site may be supplied as a separate component or may be supplied already attached to the IAS. Exemplary solid supports include glass, silicon, polystyrene, aluminum, steel, iron, copper, nickel, silver. and gold. These supports may also contain groups capable of being attached to the IAS and the selection of the solid support may be determined by the IAS. For example, where the IAS is biotin, the solid support may contain an avidin or streptavidin functionality or molecule attached thereto. The solid support may also contain an antibody. If a digoxigenin IAS is being employed, the solid support may contain the antibody capable of binding digoxigenin, such as anti-digoxigenin.

In some aspects the immobilization attachment site may also be capable of being attached to an intervening spacer arm bound to the solid support, where the intervening spacer arm may be of any length but is usually six or more atoms in length. The immobilization attachment site may also be a single stranded nucleic acid complementary to an intermediary oligonucleotide bound to the solid support.

Any chemically cleavable site may be employed, such as a modified base, a modified sugar (ribose), or a chemically cleavable group incorporated into the phosphate backbone. Exemplary chemically cleavable sites include dialkoxysilane, 3'-(S)-phosphorothioate, 5'-(S)-phosphorothioate, 3'-(N)-phosphoramidate, 5'-(N) phosphoramidate, and ribose.

This kit may also include an enzyme for extending the first and second primers, such as a DNA polymerase or a ligase. Also included may be a reagent capable of cleaving the chemically cleavable site. Some exemplary chemical reagents include 2-iodoethanol, 2,3-epoxy-1-propanol, silver, and fluoride.

This kit may be further adapted for analyzing more than one target nucleic acid simultaneously or sequentially. These adapted kits may typically further include a third primer complementary to a second target nucleic acid having a first region containing the 5' end of the third primer and an immobilization attachment site and a second region containing the 3' end of the third primer and a chemically cleavable site; and a fourth primer complementary to an extension product of the third primer. In this embodiment, the first and third primers should be selected such that the masses of the extension segments generated by extending the primers in the presence of the target nucleic acids and cleaving at the cleavable sites of the first and third primers are distinguishable by mass spectrometry. One way of accomplishing that, particularly where the masses of the sequences added by extending the first and third primers are similar, is to locate the cleavable sites of the first and third primer at differing locations relative to the 3' ends of the first and primers.

Also encompassed are kits for simultaneously analyzing more than one target nucleic acid. These kits include a plurality of first primers complementary to a plurality of target nucleic acids each having a first region containing the 5' end, and a second region containing the 3' end of the respective first primer and a chemically cleavable site; and a plurality of second primers complementary to a plurality of extension products of the plurality of first primers. In these kits, the various first primers are selected such that the masses of extension segments generated by extending the primers in the presence of the target nucleic acids and cleaving at the cleavable sites of the first primers are distinguishable by mass spectrometry. For example, the cleavable sites of at least two of the first primers may be located at differing locations relative to their respective 3' ends. Thus, the location of the cleavable sites of the first primers relative to their respective 3' ends may be selected to distinguish the masses of extension segments generated by extending the first and second primers in the presence of the plurality of target nucleic acids and cleaving at the cleavable sites of the first primers.

This kit may be used to analyze double-stranded and single-stranded nucleic acids simultaneously or sequentially and may further contain an enzyme for extending the first and second primers or a solid support.

At least one first or second primer may optionally include an immobilization attachment site for binding to a solid support.

In a related aspect, a method of sequencing is provided that utilizes the modified primers of the invention for determining the sequence of a target molecule by mass spectrometry. In one embodiment of this aspect of the invention, the sequence of a target nucleic acid is determined by hybridizing a modified immobilizable primer of the present invention with a target nucleic acid, such as DNA or RNA, followed by enzymatically extending the primer in the presence of a first of four different dideoxy nucleotides (chain terminators) to generate a mixture of primer extension products. The primer extension products each contain a primer and an extension segment. The extension products are denatured, immobilized, and washed to remove non-immobilized species present in the reaction. As in the embodiments described above, immobilization can occur before or after enzymatic extension, and is typically carried out prior to cleavage at the cleavable site. Subsequent to immobilization and removal of non-immobilized species, the primer extension products are cleaved to release the extension segments. The extension segments are sized by mass spectrometry, and the above steps are repeated with each of the three remaining different dideoxy nucleotides. The sequence of the target is then determined by comparing the sizes of the extension segments obtained from each of the four extension reactions. In a variation of the above, a single primer extension reaction is carried out using a mixture composed of more than one chain-terminating nucleotide, up to all four (e.g., subsets of the following containing at least one dideoxynucleotide: dTTP, ddTTP, dATP, ddATP, dCTP, ddCTP, dGTP, and ddGTP). The resulting reaction mixture, containing up to all four-base specifically terminated products, is then analyzed using the mass data and known mass values for the four bases. Optionally, mass modified nucleotides may be utilized to enhance the resolution of the product mixture. Sequencing can also be carried out using the modified primers of the invention coupled with alternate sequencing methodologies which do not employ dideoxynucleosides.

Similarly, methods of analyzing single nucleotide polymorphisms (SNPs) are provided that utilize the modified primers of the invention for determining the presence, nature and location of an SNP by mass spectrometry. In one embodiment, the SNP is analyzed by hybridizing a modified immobilizable primer of the present invention with a target nucleic acid, such as DNA or RNA, followed by enzymatically extending the primer in the presence of only the four dideoxy nucleotides (chain terminators, e.g., ddTTT, ddUTP, ddATP, ddCTP, ddITP and ddGTP) to generate a primer extension product. Thus, the primers are only extended by one base—the base complementary to the site of the suspected polymorphism.

The primer extension product for these SNP analysis methods each contain a primer and a single added dideoxy nucleotide. The extension products are denatured, immobilized, and washed to remove non-immobilized species present in the reaction. As in the embodiments described above, immobilization can occur before or after enzymatic extension, and is typically carried out prior to cleavage at the cleavable site. Subsequent to immobilization and removal of non-immobilized species, the primer extension products are cleaved to release the added dideoxynucleotide attached to a portion of the primer. The released fragment is sized by mass spectrometry and the mass of the added dideoxynucleotide determined by subtracting the known mass of the portion of the primer 3' of the cleavable site. The presence and nature of the SNP is then determined by comparing the identity of the added base to that found in the wild-type (nonpolymorphic) nucleic acid. This method may also be employed with multiple primers ending at different locations to determine the location of possible SNPs. Optionally, mass modified nucleotides may be utilized to enhance the resolution of the product mixture.

Methods for detecting SNPs can be expanded to the analysis of polymorphisms in general. Polymorphisms include both naturally occurring, somatic sequence variations and those arising from mutation. Polymorphisms include but are not limited to: sequence microvariants where one or more nucleotides in a localized region vary from individual to individual, insertions and deletions which can vary in size from one nucleotides to millions of bases, and microsatellite or nucleotide repeats which vary by numbers of repeats. Nucleotide repeats include homogeneous repeats such as dinucleotide, trinucleotide, tetranucleotide or larger repeats, where the same sequence in repeated multiple times, and also heteronucleotide repeats where sequence motifs are found to repeat. For a given locus the number of nucleotide repeats may vary depending on the individual. Through the use of strategic placement of the cleavable primer and a combination of deoxy and dideoxy or other chain-terminating nucleotides one may be able to span the region of a polymorphism, e.g. placement of the cleavable primer adjacent and upstream from a polymorphism, and extension of the primer by polymerase, wherein a dideoxy nucleotide is added downstream from the polymorphism to terminate extension. Variations in the size of the chain terminated extension products can be used to identify the type and variance within a given polymorphism.

An aspect thus includes methods for determining the presence of a polymorphism in a target nucleic acid. These methods typically include the steps of: hybridizing a primer with a target nucleic acid suspected of containing a polymorphism, where the primer has a first region containing the 5' end of the primer and a second region containing the 3' end of the primer and a cleavable site; extending the 3' end of the primer with a polymerase in the presence of a nucleotide to generate an extension product; cleaving the extension product at the cleavable site to release an extension segment; sizing the extension segment by mass spectrometry (such as by TOF MS), whereby said cleaving is effective to increase the read length of the extension segment relative to the read length of the extension product; and identifying any added nucleotides. This method may be employed to analyze many types of nucleic acids, such as RNA and DNA, both single- and double-stranded.

The extension step may be carried out in the presence of one or more nucleotides, including, for example, deoxynucleotides, chain-terminating nucleotides and derivatives thereof, depending on the nature of the suspected polymorphism. For example, if one is interested in identifying an SNP, the extension step may be carried out in the presence of only chain-terminating nucleotides, such as dideoxynucleotides (e.g. ddATP, ddTTP, ddUTP, ddGTP, ddITP and ddCTP) and mass-modified chain-terminating nucleotides, and then identification of the added dideoxynucleotide determines the presence and identity of the single nucleotide polymorphism. Mass-modified are well known in the art and may be used to, for example, increase the mass difference of certain nucleotides (such as deoxy- and dideoxy-adenine and thymine).

The first region of the primer may contain an immobilization attachment site and the extension product may be immobilized onto a solid support at the immobilization attachment site prior to the cleaving step. In this embodiment, it may also be desirable to wash the extension product after said immobilizing and prior to said cleaving.

In some embodiments, it may be desirable to immobilize the target nucleic acid. Under these circumstances, the target nucleic acid may be immobilized prior to or after said extending.

Cleavable sites for these methods include blocking nucleotides capable of blocking 5' to 3' enzyme-promoted digestion. In these instances, the cleaving may be carried out by digesting the first region of the primer with an enzyme having a 5' to 3' exonuclease activity, such as T7 gene 6 exonuclease and phosphodiesterase. Such blocking nucleotides include phosphorothioates, methyl phosphonates, phosphotriesters, and peptide nucleic acids.

Cleavable sites may also be chemically cleavable sites, such as modified sugar, modified bases, and groups incorporating a chemically cleavable group into the phosphate backbone of the primer. Some exemplary cleavable sites include dialkoxysilane, 3'-(S)-phosphorothioate, 5'-(S)-phosphorothioate, 3'-(N)-phosphoramidate, 5'-(N)phosphoramidate, uracil, and ribose.

This method may also be coupled with amplification of the target nucleic acid.

A This method may also be adapted for analyzing a plurality of target nucleic acids. In these embodiments, typically a plurality of primers are hybridized to more than one target nucleic acid and the location of the cleavable site contained within the primers is varied to increase the mass difference between the respective extension segments.

In another embodiment, the sequence of a target nucleic acid, such as DNA or RNA, is determined by first hybridizing a primer with a target DNA, where the primer (i) is complementary to the target DNA; (ii) has a first region containing the 5' end of the primer and an immobilization attachment site; and (iii) has a second region containing the 3' end of the primer and a cleavable site. The 3' end of the primer is also capable of serving as a priming site for enzymatic extension.

The primer is then extended with an enzyme in the presence of a first of four different deoxynucleotide α-thiotriphosphate analogs (dNTPαS) to generate a mixture of primer extension products containing phosphorothioate linkages. The phosphorothioate-containing extension products are then treated with a reagent that cleaves specifically at the phosphorothioate positions. Suitable reagents for promoting phosphorothioate-specific cleavage include 3' to 5' exonuclease, 2-iodoethanol, and 2,3-epoxy-1-propanol. Treating of the extension products is typically carried out under conditions that produce limited cleavage of the phosphorothioate linkages, resulting in the production of a group of primer extension degradation products. Alternatively, the primer extension reaction can be carried out using a limited amount of the α-thio-deoxynucleoside triphosphate analog along with the corresponding conventional deoxynucleoside triphosphate (dNTP). The resulting extension products are then treated with a phosphorothioate-selective reagent as described above, under conditions effective to cleave all of the phosphorothioate groups incorporated into the extension product (complete cleavage).

The primer extension degradation products are immobilized at the immobilization attachment sites to produce immobilized primer extension degradation products (i.e. a nested set of fragments specific to the 5' end containing the primer), each containing a primer and an extension segment. In alternative embodiments of this aspect of the invention, immobilization may be carried out either (i) prior to enzymatic extension, (ii) after enzymatic extension, (iii) prior to treating the phosphorothioate-containing primer extension products with a phosphorothioate-specific cleaving reagent, or (iv) after such treating.

Subsequent to immobilization, the primer extension degradation products are washed to remove non-immobilized species. Cleavage at the cleavable site results in the release of extension segments, which are then sized by mass spectrometry. Using the sequencing method of this aspect of the invention, the read length of any given extension segment is increased relative to the read length of its corresponding primer extension degradation product.

The steps of hybridization, enzymatic extension, treatment with a phosphorothioate-cleaving reagent, immobilization, washing, cleaving, and sizing are then repeated with a second, third, and fourth of the four different dNTPαS analogs to determine the sequence of the target DNA by comparison of the sizes of the extension segments obtained from each of the four extension reactions. Optionally, the steps of hybridization, enzymatic extension, treatment with a phosphorothioate-cleaving reagent, immobilization, washing, and cleaving can be carried out in the presence of from 2–4 different dNTPαS analogs, followed by sizing of the resulting extension segments by mass spectrometry.

In all aspects of the invention, the extension segments from multiple primers may be analyzed simultaneously. In cases where the different primer extension products are all of similar size and mass, one may opt to vary the position of the cleavage site in the different primers such that the fragments released after cleavage are distinguishable, or more easily distinguishable by MS analysis. Thus, another embodiment encompasses the creation and use of mixtures of cleavable primers for multiplexed analysis where the cleavage site is located at different sites along the backbone for different primers relative to the segment added by extension such that the masses of the cleaved and released fragments are distinguishable by mass. In cases where each of the primers in a multiplex analysis is likely to be extended to create similarly-sized extension products (by mass), for example, single base dideoxynucleotide additions and LCR or PCR amplifications, the placement of the cleavage site at differing locations within the cleavable primers will result in cleaved and released extension products that will vary by one or more nucleotides. By differentiating the masses of the cleaved products, one may observe multiple primer extension products simultaneously. An example for single nucleotide extensions is shown in FIG. 17.

In these aspects, the initial primers may have very different masses but still result in extension products which would have similar masses. In these embodiments, it is the masses of the cleaved fragments that should be distinguished relative to each other by moving the cleavable site within the various primers, as opposed to the masses of the primers or uncleaved extension products.

According to yet another aspect, a method of fingerprinting is provided which utilizes the modified primers of the invention for obtaining a fingerprint of a target oligonucleotide.

These and other objects and features of the invention will become more fully apparent when the following detailed description is read in conjunction with the accompanying figures and examples.

3.0 BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A–1W show a native phosphodiester internucleotide linkage (FIG. 1A) and exemplary internucleoside cleavable sites for use in the oligonucleotide composition of the present invention: dialkoxysilane (FIG. 1B); β-cyano ether (FIG. 1C); 5'-deoxy-5'-aminocarbamate (FIG. 1D); 3'-deoxy-3'-aminocarbamate (FIG. 1E); urea (FIG. 1F); 2'-cyano-3',5'-phosphodiester (FIG. 1G); 3'-(S)-phosphorothioate (FIG. 1H); 5'-(S)-phosphorothioate (FIG. 1I); 3'-(N)-phosphoroamidate (FIG. 1J); 5'-(N)-phosphoroamidate (FIG. 1K); α-amino amide (FIG. 1L); vicinal diol (FIG. 1M); ribonucleoside insertion (FIG. 1N); 2'-amino-3',5'-phosphodiester (FIG. 1O); allylic sulfoxide (FIG. 1P); ester (FIG. 1Q); silyl ether (FIG. 1R); dithioacetal (FIG. 1S); 5'-thio-formal (FIG. 1T); α-hydroxy-methylphosphonic bisamide (FIG. 1U); acetal (FIG. 1V); and 3'-thio-formal (FIG. 1W).

FIGS. 2A–2M include a number of exemplary immobilization attachment linkages for use in immobilizing the first region of a modified oligonucleotide primer: functiionalized maleimide (FIG. 2A, where Y equals sulfur, oxygen, or nitrogen); carbamate (FIG. 2B); ester (FIGS. 2C, 2I and 2K, where Y equals nitrogen); thiolester (FIGS. 2C, 2I and 2K, where Y equals sulfur); (N)-functiionalized thiourea (FIG. 2D); mercuric-sulfide (FIG. 2E); amino (FIG. 2F); disulfide (FIG. 2G); amide (FIG. 2H); hydrazone (FIG. 2J); streptavidin or avidin/biotin (FIG. 2L); and gold-sulfide (FIG. 2M).

Figure 5A:
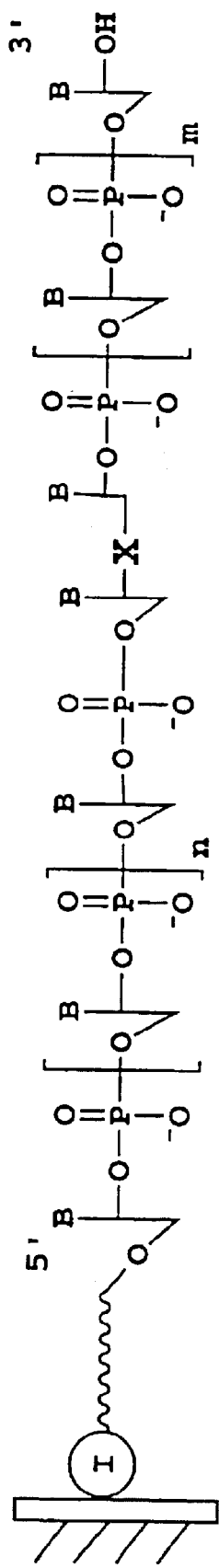
Figures 5B, 5C:
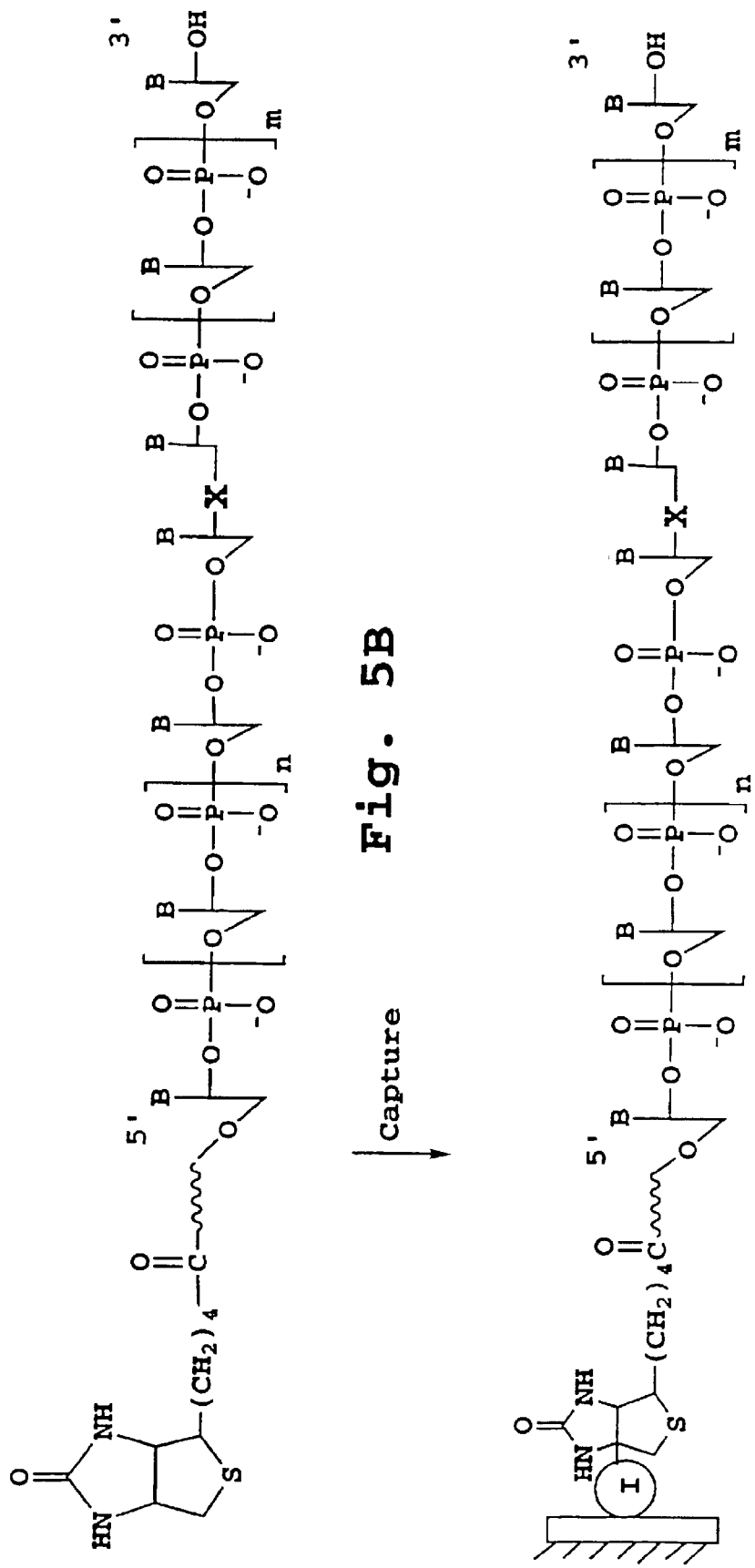
Figures 5D, 5E:
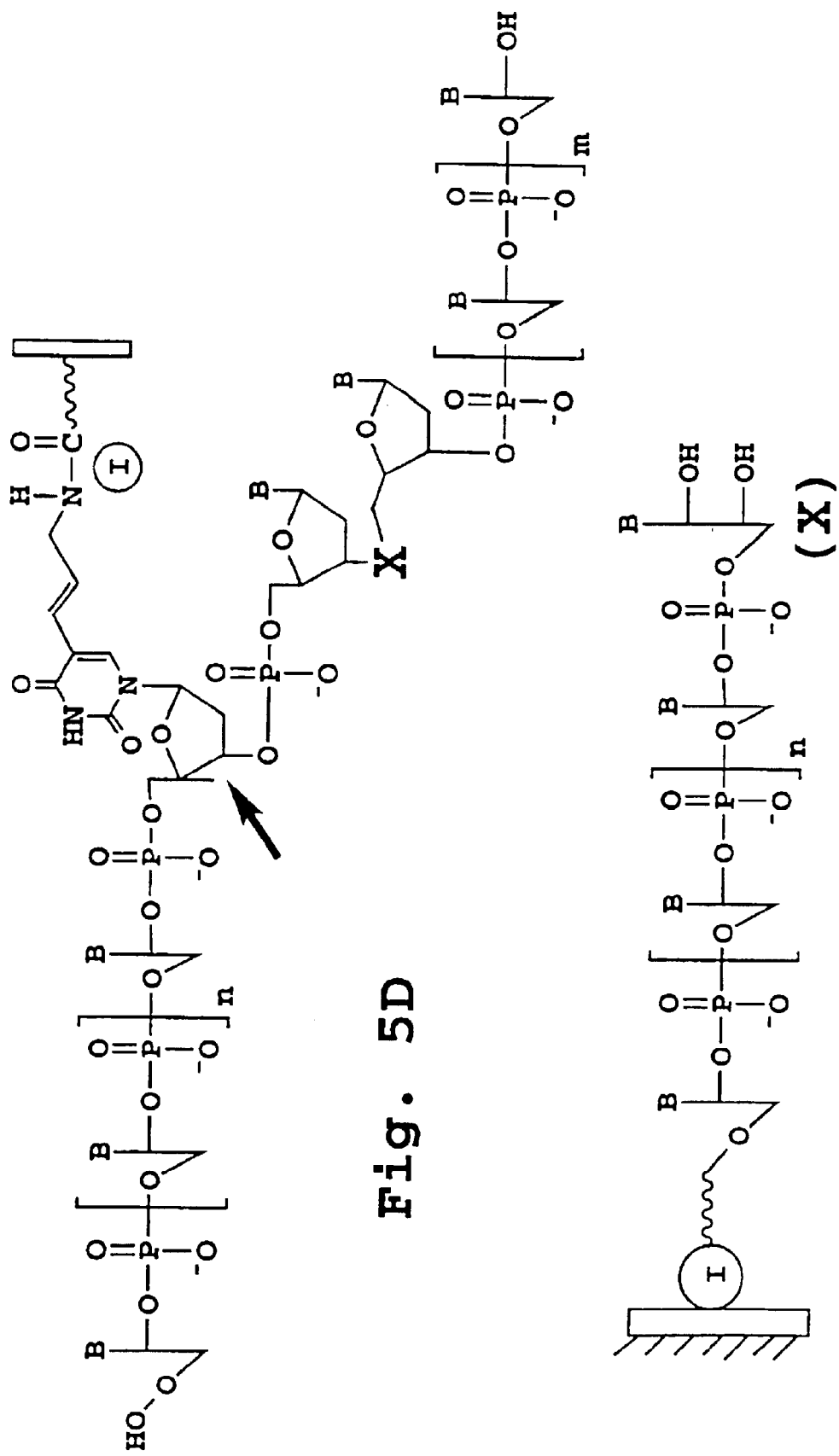

FIGS. 5A–5E illustrate four alternate embodiments of an immobilized cleavable primer in accordance with the invention. FIG. 5A presents an immobilized modified primer having two regions connected by a cleavable site, X. FIG. 5B shows a biotin molecule connected to the 5' end of a modified primer. FIG. 5C depicts the capture of a modified primer prior to enzymatic extension on an avidin-functionalized solid support. FIG. 5D represents a modified primer affixed to a solid support through a 5-allylamino substituent at the 5 position of a uracil. FIG. 5E presents a modified primer containing a terminal ribose cleavage site, X.

Figure 6A:
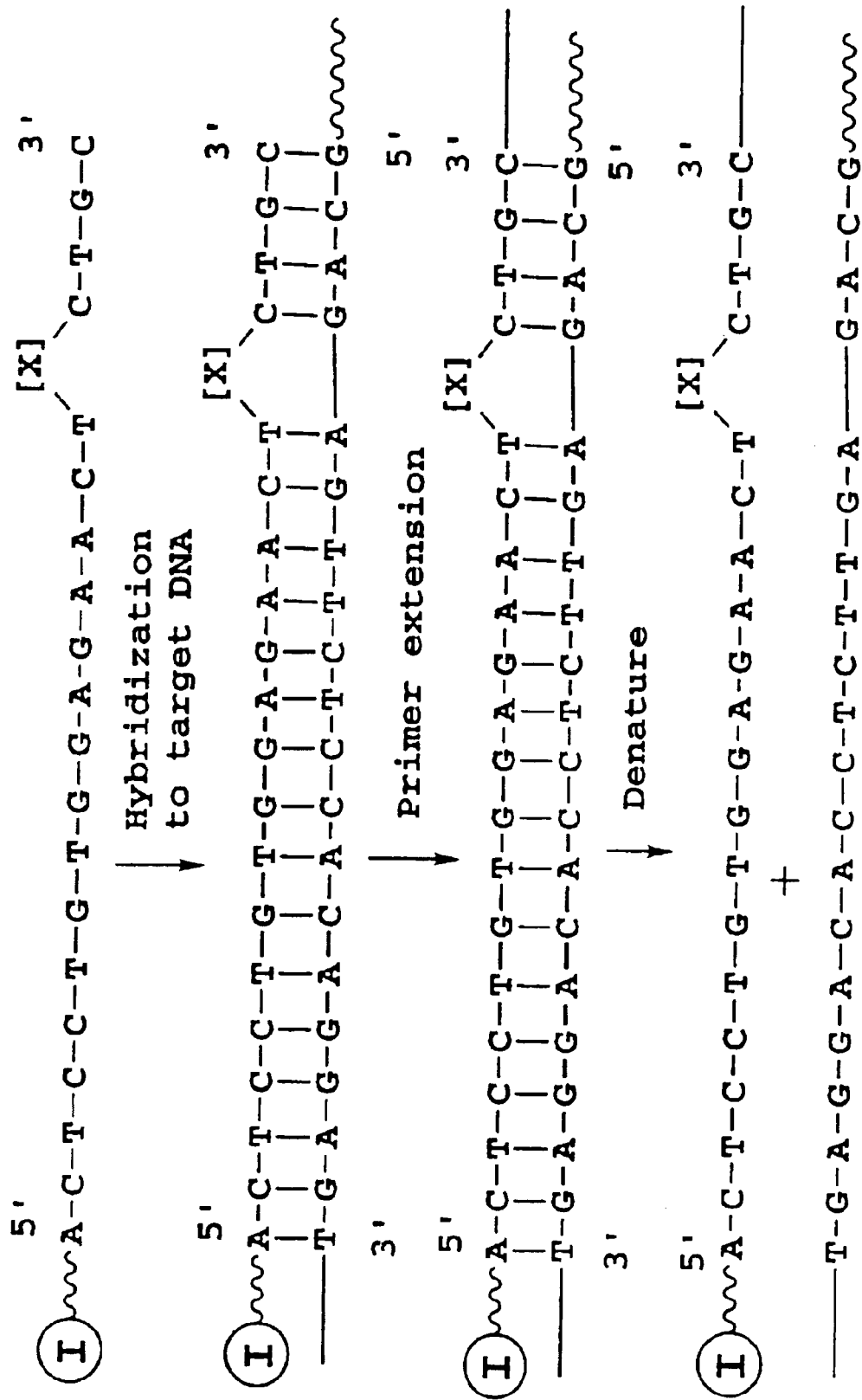
Figure 6B:
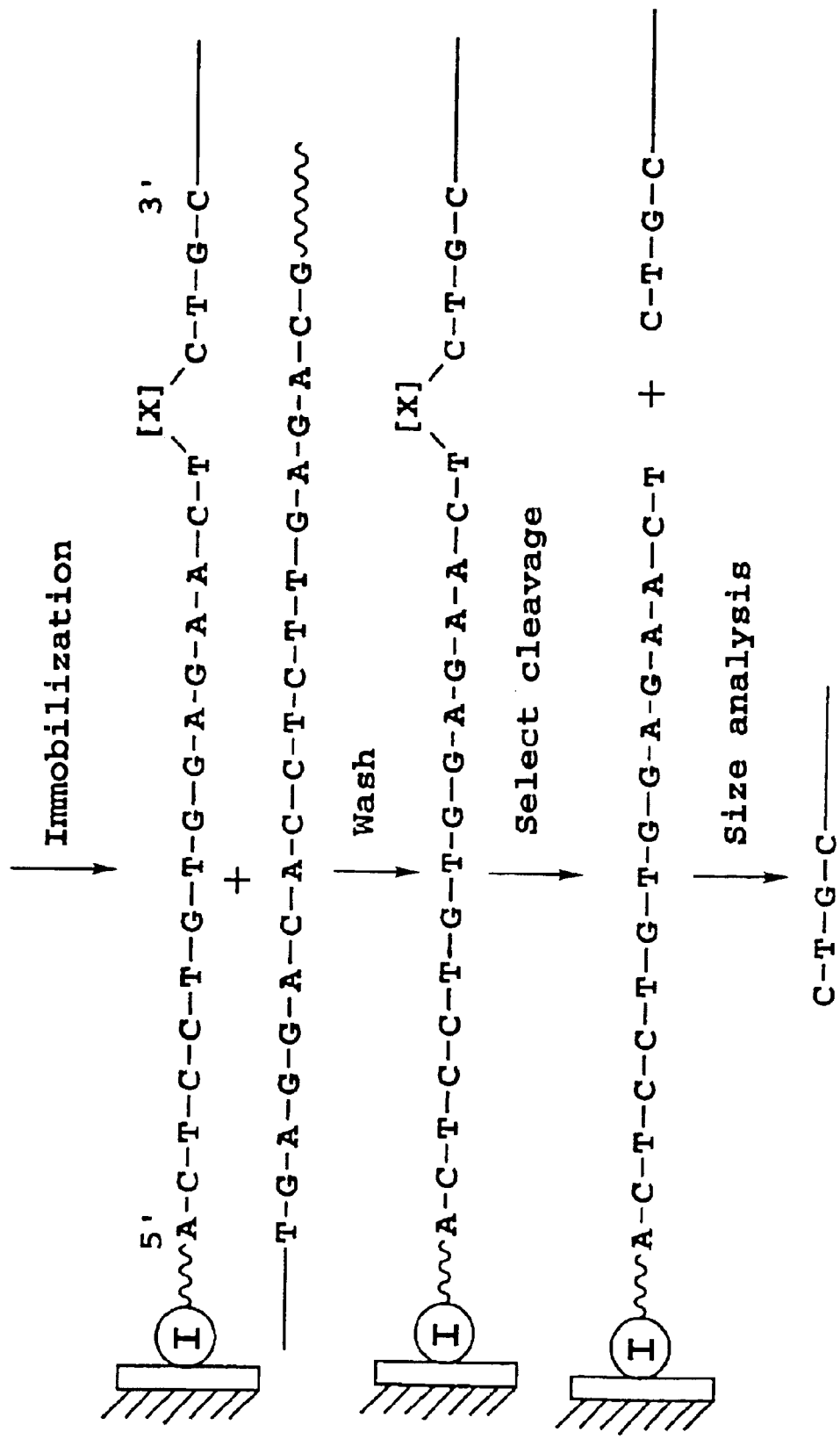

FIGS. 6A and 6B illustrate an exemplary method of determining the sequence of a target DNA molecule using the immobilizable, cleavable primers of the present invention.

FIGS. 7A and 7B illustrate the respective single gene mutation sites identified for two distinct genetic disorders, sickle cell anemia (FIG. 7A) and $\alpha_1$-antitrypsin deficiency (FIG. 7B), suitable for detection using the modified primers of the present invention.

Figure 8:
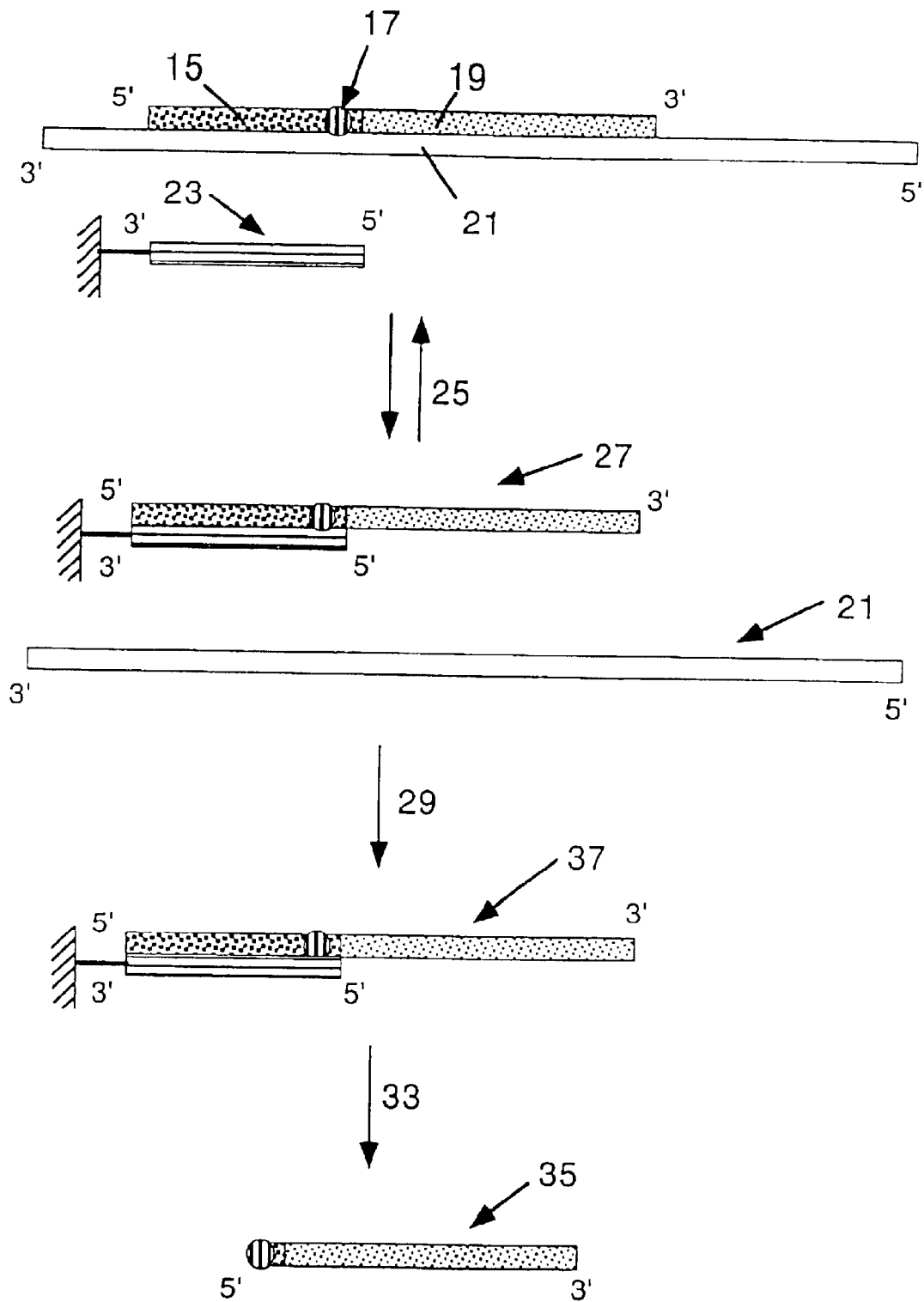

FIG. 8 illustrates the immobilization of a modified primer via competitive hybridization of the first primer region to both a target molecule and a solid phase bound intermediary oligonucleotide, SPBIO.

Figure 9:
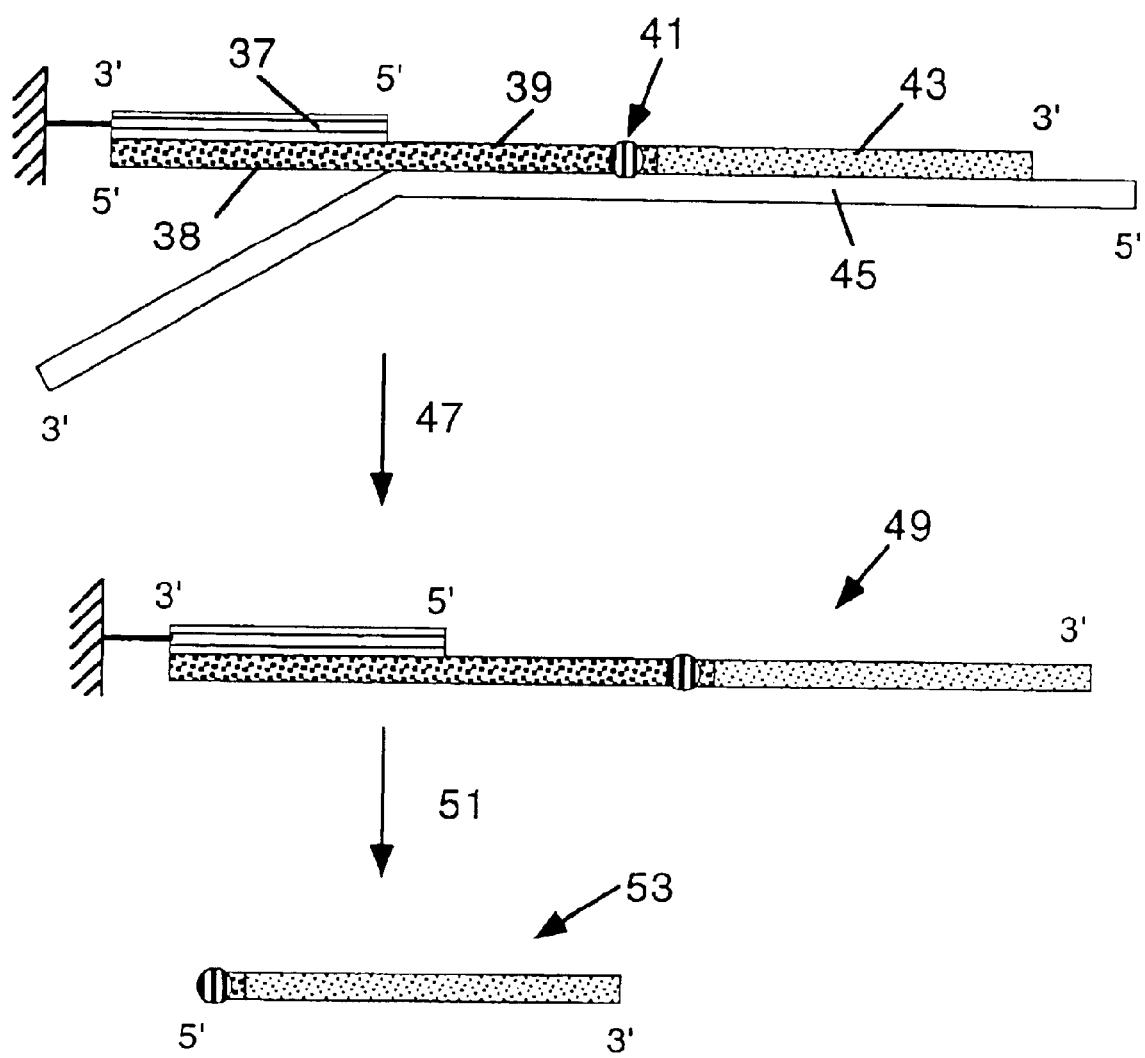

FIG. 9 illustrates the immobilization of a modified primer via hybridization to a SPBIO, where the modified primer contains a first primer region composed of a first portion complementary to the SPBIO and a downstream second portion complementary to a target molecule but not complementary to the SPBIO.

Figure 10:
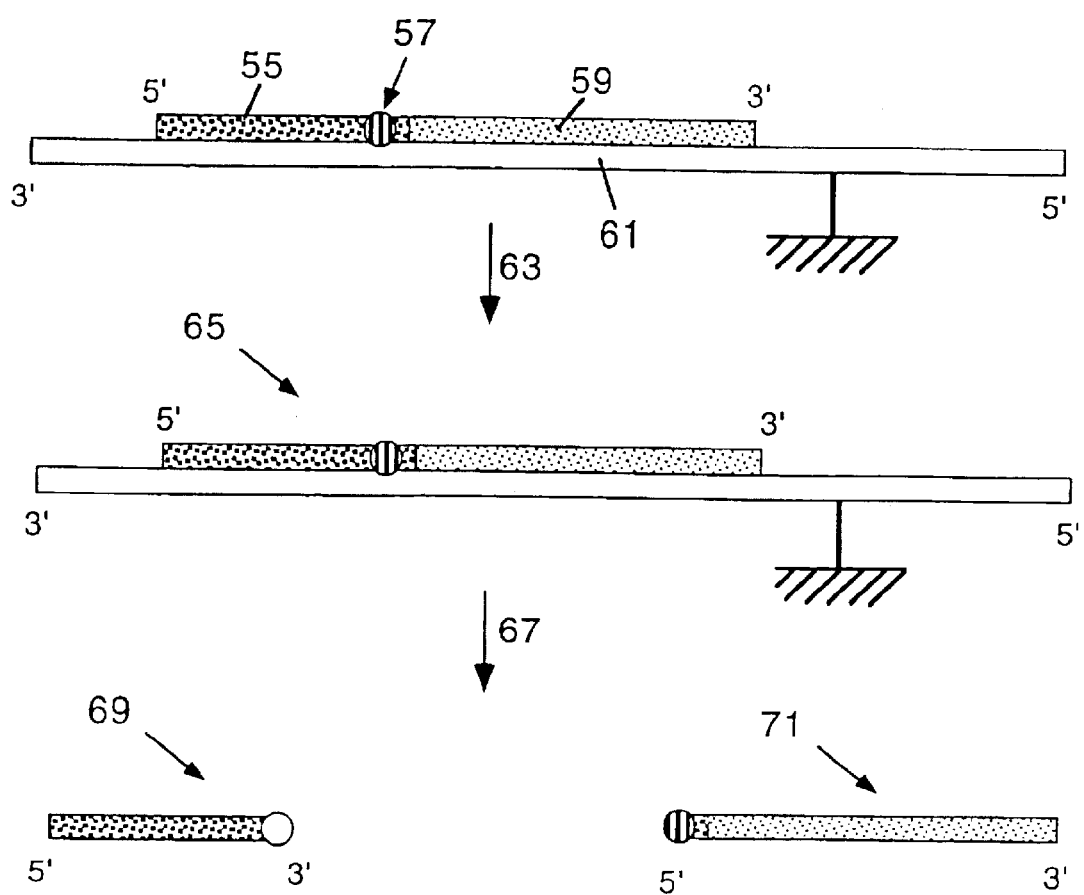

FIG. 10 illustrates immobilization of an enzymatic extension product (composed of a modified primer and an extension segment) via base-pairing interaction to a target molecule bound to a solid support.

Figure 11:
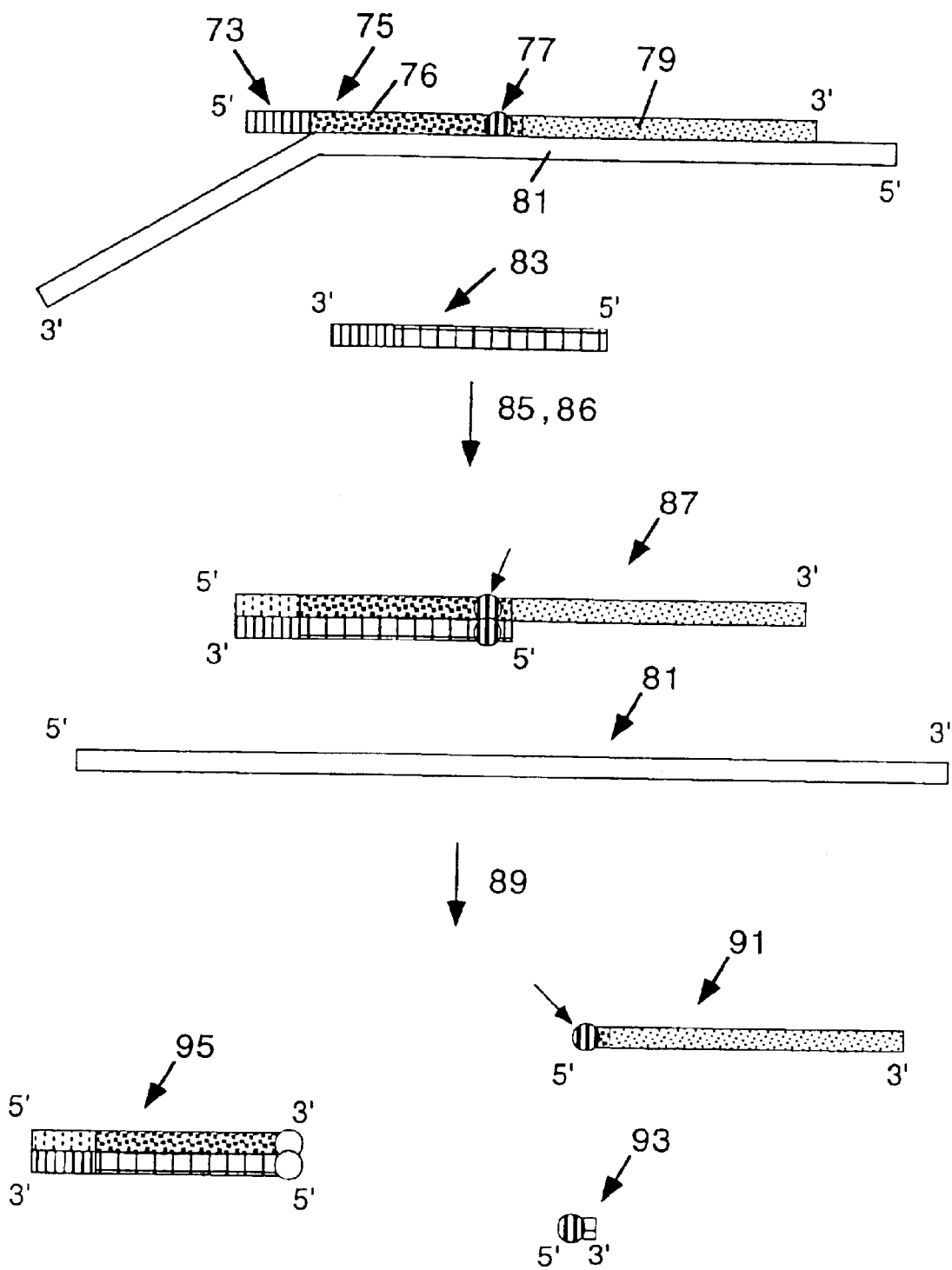

FIG. 11 illustrates sequence-specific cleavage of an enzymatic extension product, where the modified primer contains a restriction recognition site in the first primer region and a cleavable site in the second primer region.

Figure 12:
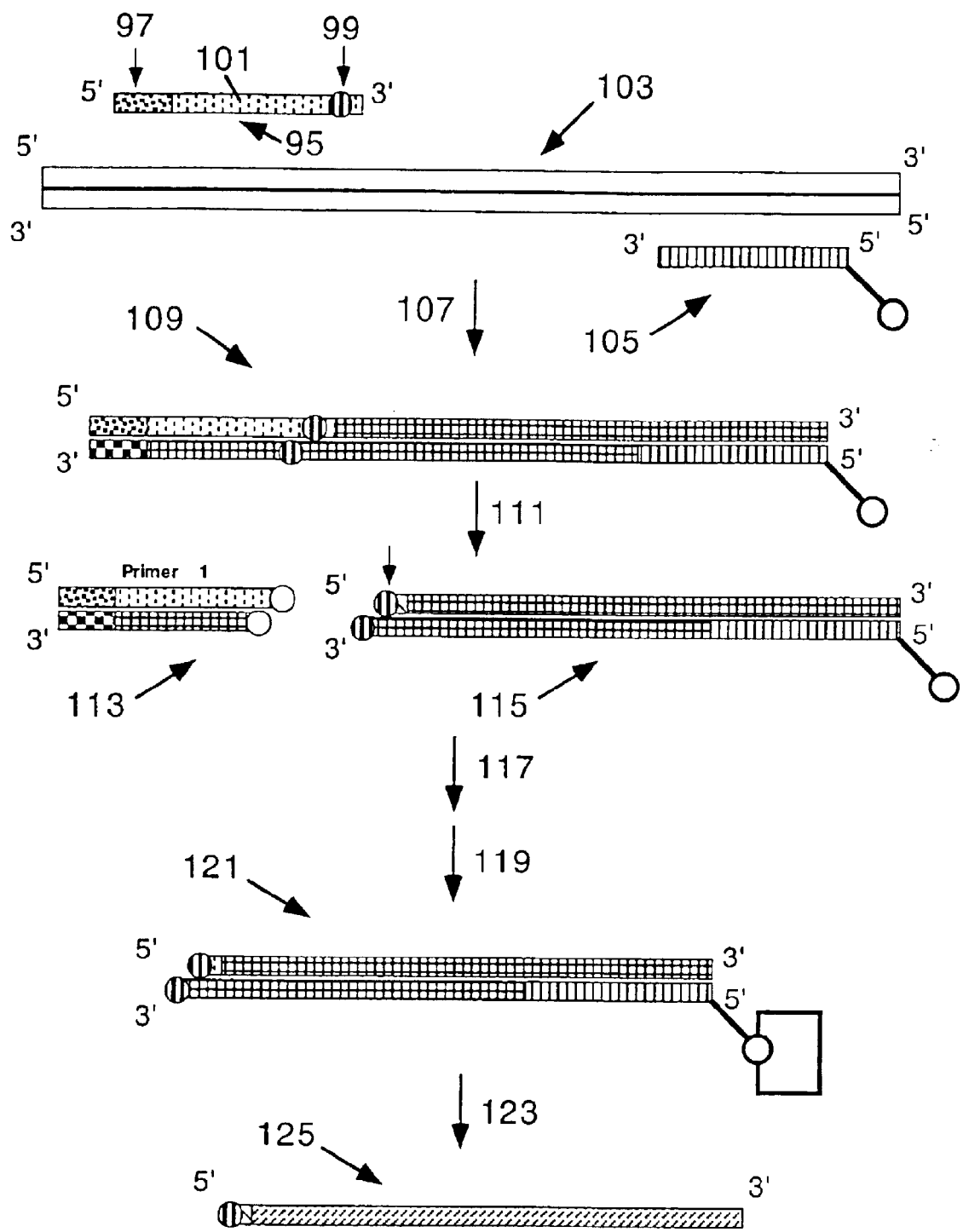

FIG. 12 illustrates an exemplary sizing method of the present invention using first and second modified primers, where the first primer contains an enzyme-cleavable site and the second primer contains an immobilization attachment site.

Figure 13:
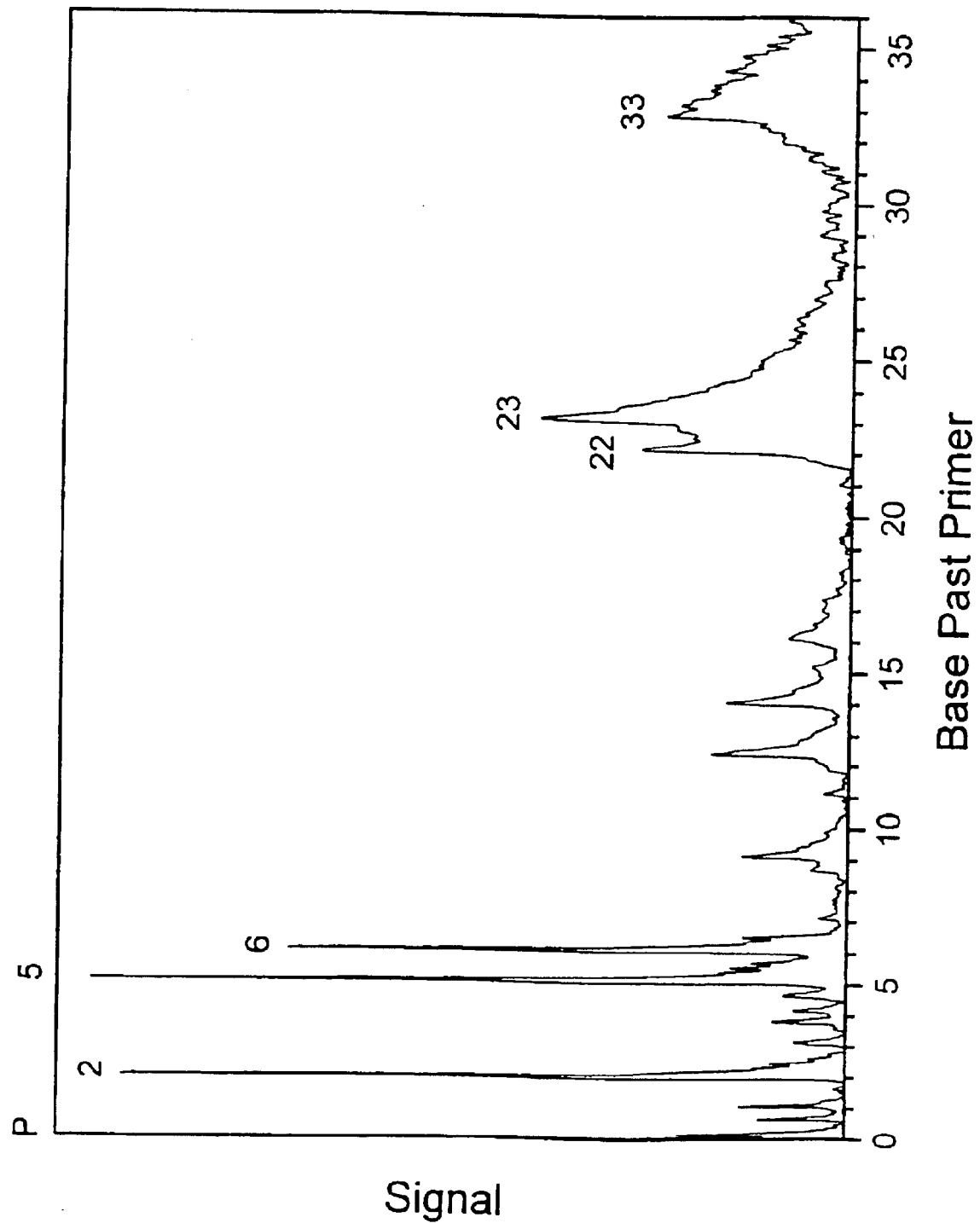

FIG. 13 is a MALDI time-of-flight mass spectrum of primer extension products obtained from an extension reaction using a primer containing a 5-thiol thymidine cleavable site and a 10-fold excess of primer. Primer extension products were immobilized via hybridization to a complementary biotinylated intermediary oligonucleotide bound to streptavidin coated beads and released by chemical cleavage for subsequent size analysis.

FIGS. 14A and 14B are MALDI time-of-flight mass spectra illustrating the utility of the present method in detecting single base substitutions (point mutations) between oligonucleotides, using base-specific digestion. FIG. 14A corresponds to reaction product(s) derived from template 16-C/19-G, SEQ ID NO:17 and FIG. 14B corresponds to reaction product(s) derived from template 16-A/19-T, SEQ ID NO:18.

Figure 15A:
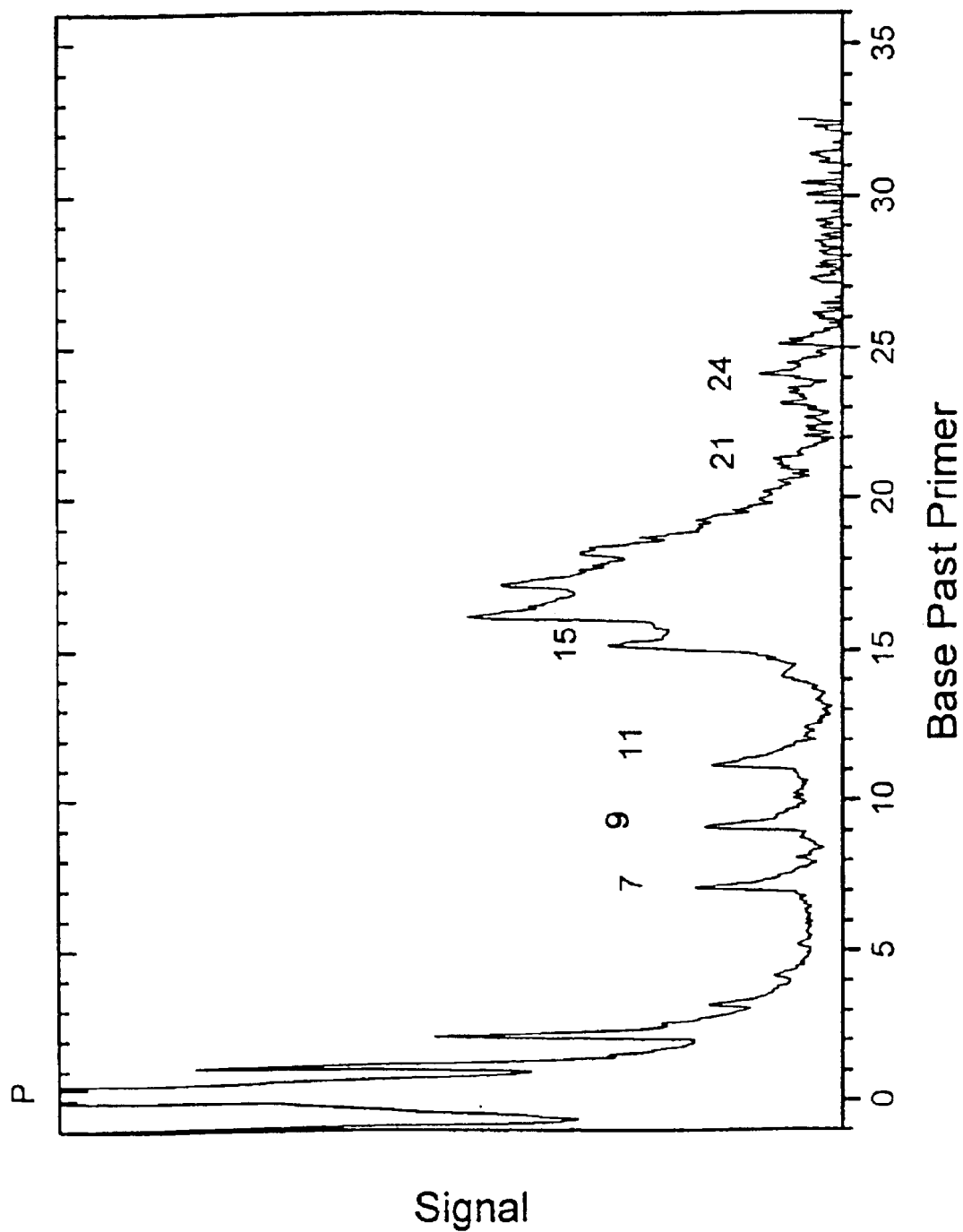
Figure 15B:
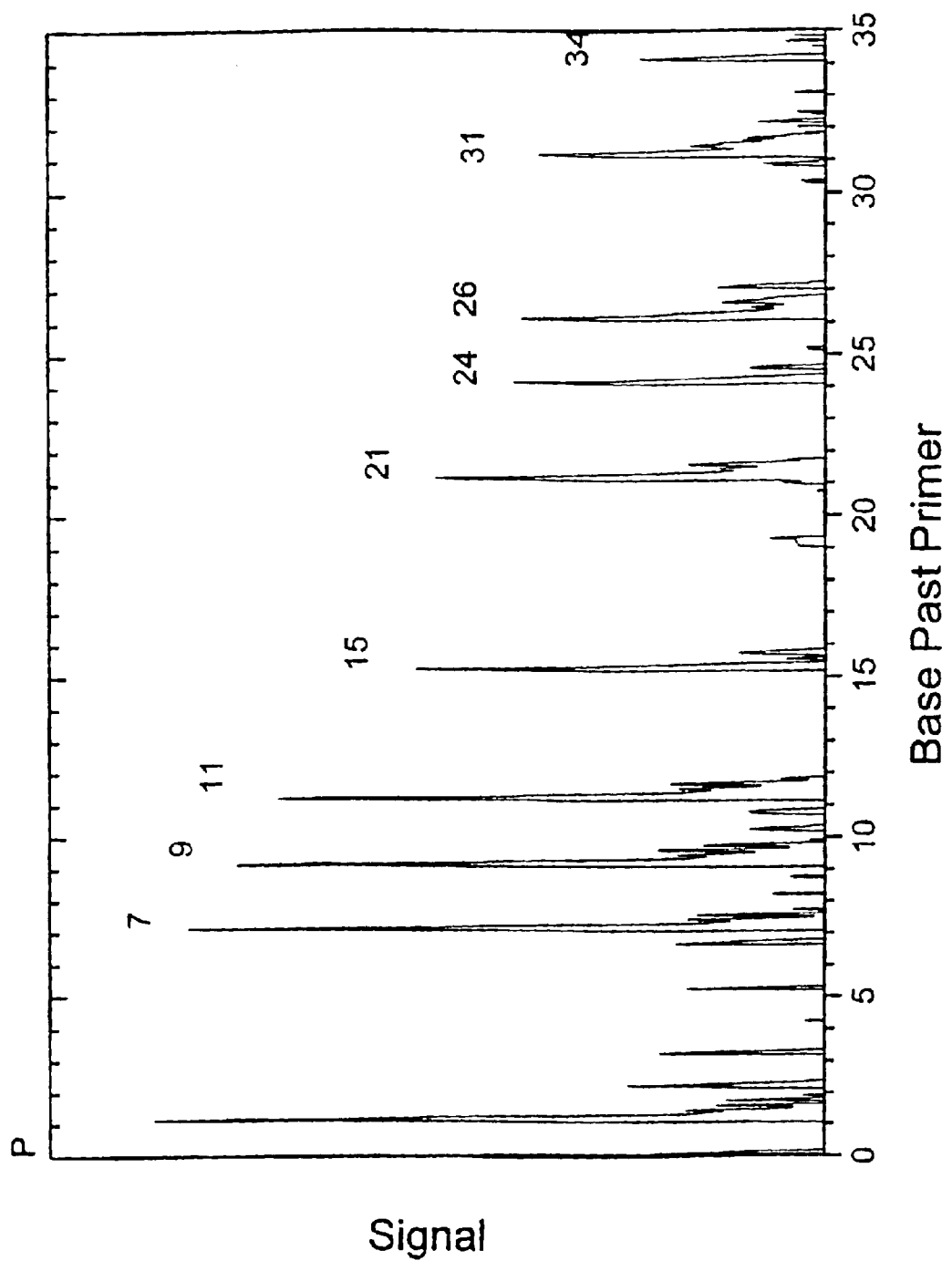

FIGS. 15A and 15B are MALDI time-of-flight mass spectra of primer extension products obtained using (i) a cleavable primer according to the present invention (FIG. 15B) versus (ii) a full length primer (FIG. 15A), illustrating the difference in both resolution and read length of the resulting spectra.

Figure 16:
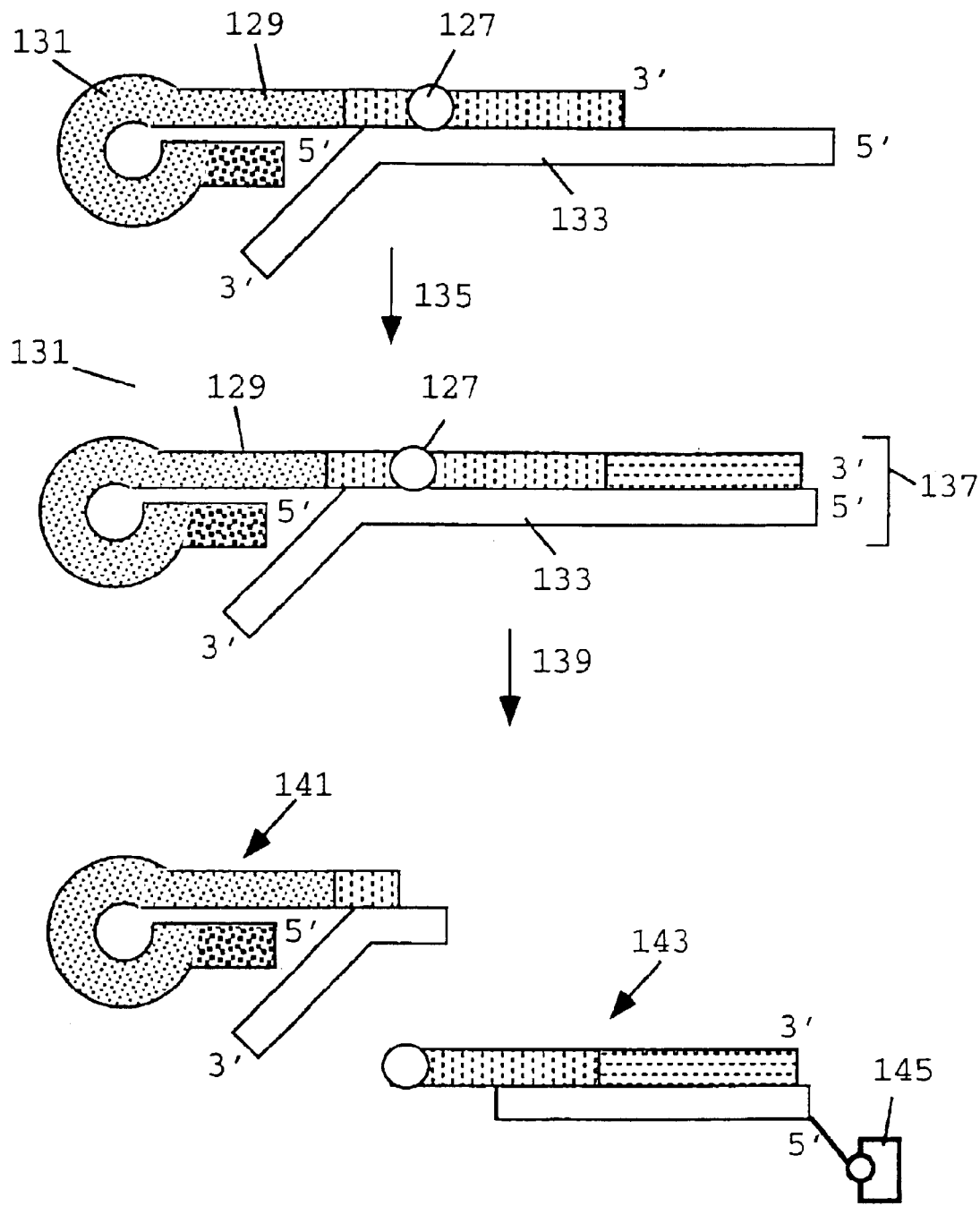

FIG. 16 illustrates sequence-specific cleavage of an enzymatic extension product, where the modified primer contains a class IIs restriction enzyme recognition site in the first primer region, composed of a 5' hairpin-type (self-complementary double stranded) domain, and a cleavable site in the second primer region.

Figure 17:
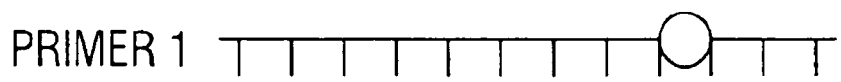
Figure 17:
Figure 17:
Figure 17:
Figure 17:
Figure 17:
Figure 17:
Figure 17:
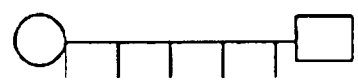

FIG. 17 illustrates multiplexed analysis by moving the cleavable site along the primer. Primer 1 contains a cleavable site (o) between bases 3 and 4 while primer 2 has a cleavable site between bases 5 and 6. Single base extension (step a) by a dideoxy chain terminating nucleotide (□) yields two products having similar masses. However, cleavage (step b) of the two primers (preferably after immobilization and purification) results in two released fragments more easily distinguishable by mass: primer product 1 having 4 bases and primer product 2 having 6 bases.

4.0 DESCRIPTION OF ILLUSTRATIVE EMBODIMENTS

4.1 Definitions

The following terms, as used herein, have the meanings as indicated:

In referring to a position within a single stranded oligonucleotide, a position that is "upstream" from a specified position is located 5' to this position, while a position that is "downstream" is located 3' to the point of reference.

An "immobilization attachment site" or IAS is a site which may be present within an oligonucleotide primer for binding to a solid support material directly, through an intervening spacer arm, or by specific hybridization to an intermediary oligonucleotide which is bound to a solid support. The immobilization attachment site may be located either upstream (i.e. 5' to) or downstream (i.e. 3' to) of the cleavable site and may require chemical modification prior to binding to the solid support The IAS may also be flanked both upstream and downstream by more than one cleavable sites. Alternatively, the immobilization attachment site may be contained within the extension segment resulting from an enzymatic extension reaction, or, may be contained within a target nucleic acid. The immobilization attachment site can be a select functional group for covalent bonding to a solid support, such as those representative functional groups shown in FIGS. 2A–2K, and FIG. 2M. The immobilization attachment site can also be a ligand such as biotin, for attachment via a high-affinity non-covalent interaction with a solid support. Further the immobilization attachment site can also be composed of a series of bases complementary to an intermediary oligonucleotide. Immobilization of the modified primer is effected, for example, by specific hybridization of the immobilization attachment site to an intermediary oligonucleotide, which is bound to a solid support. The intermediary oligonucleotide may also act as the template. The immobilization attachment site may be attached to the solid support by either chemical or enzymatic means. Upon attachment of the immobilization attachment site to a solid support, the resulting immobilization linkage is one which remains stable under the conditions employed for cleaving the cleavable site and does not inhibit base pair hybridization nor block the ability to extend the primer from its 3' end.

Two nucleic acid fragments are considered to be "selectively hybridizable" if they are capable of specifically hybridizing to one another but not to other polynucleotides, under typical hybridization and wash conditions, as described, for example, in Maniatis et al., 1982.

Two nucleic acid fragments are considered to be "complementary" if they are capable of specifically hybridizing to one another (i) under typical hybridization and wash conditions, as described, for example, in Maniatis et al. (1982) or (ii) using reduced stringency wash conditions that allow at most about 25–30% base pair mismatches, for example: 2×SSC, 0.1% SDS, room temperature twice, 30 min each; then 2×SSC, 0.1% SDS, 37° C. once, 30 min; then 2×SSC room temperature twice, 10 min each.

"Cleavable site" as used herein is a reactive moiety typically (i) located at or within about five nucleotides from the 3' end of a primer, and (ii) selectively cleavable by appropriate non-enzymatic or enzymatic means including chemical, thermal, or photolytic, to enable release of primer extension products that typically contain none or a relatively small number of base pairs of the modified primer. Cleavable site refers both to the selectively cleavable functional group as described above and also to protected forms thereof. The cleavable site may, for example, be (i) located along the polymer backbone (i.e. a modified 3'-5' internucleotide linkage in place of one of the phosphodiester groups), (ii) as a substituent on or replacement of one of the bases or sugars of the oligonucleotide primer, or (iii) as the 3' terminal residue (e.g., a ribonucleotide at the 3' end of the oligodeoxyribonucleotide primer). The cleavable site is stable under standard solid phase DNA synthesis conditions, during primer immobilization, hybridization, primer extension, and washing conditions.

As used herein, a cleavable site may also be a nucleotide cleavable by an enzyme such as a nuclease. For example, the cleavable site may be a restriction endonuclease cleavable site, where the recognition sequence is located in the first primer region (i.e. upstream of the cleavage site). Exemplary restriction endonucleases for use in cleaving at the cleavable site include BpmI, BsgI, BseRI, BsmFI, and FokI.

A cleavable site may also be a nucleotide or series of nucleotides capable of blocking or terminating 5' to 3' enzyme-promoted digestion by an enzyme having 5' to 3' exonuclease activity, such as T7 gene 6 exonuclease (Amersham Life Sciences, Arlington Heights, Ill.). Representative blocking nucleotides are those containing a phosphorothioate, borano-phosphate, or peptide group. The blocking nucleotide/cleavable site should be one which does not inhibit enzymatic extension of the primer.

As described herein, "fingerprinting" refers to a method of determining the positions of no more than two different bases in a target oligonucleotide strand, as opposed to "sequencing", which refers to a determination of the complete nucleotide sequence of (and also the corresponding amino acid sequence encoded by) a target oligonucleotide, including the identity and position of each nucleotide present in the target strand or its complement.

"Non-covalent linkage" refers to any type of non-covalent bonding interaction, and is used herein primarily to describe different types of immobilization attachment sites. A non-covalent linkage includes base-specific hydrogen bonding interactions, such as those occurring between complementary nucleotide base pairs, or may refer to a high affinity ligand-protein interaction, such as the biotin/avidin or biotin/streptavidin interaction ($K_a=10^{15}$ $M^{-1}$).

"Extension segment" refers to the product resulting from in vitro enzymatic extension at the 3' end of a primer, excluding the portion of nucleotides originally present in the primer prior to extension.

As used herein "a" will be understood to mean one or more. Thus, "a nucleotide" may refer, for example, to one, two, three, four, five or more nucleotides.

As used herein, "read length" refers to the number of nucleotides of a given target sequence for which new analytical data (e.g., sizing, quantification, sequencing) can be obtained. New data refers to fragment information for primer extension products which excludes data derived from portions of the target DNA complementary to the primer(s) employed (e.g. regions for which sequence information is already known).

Read length is typically method dependent (i.e. a function of the detection method being employed). In some analytical methods size resolution may have an essentially finite upper limit, (e.g., up to 100 nucleotides). One advantage of the present invention is the ability to improve the amount of new or useful information about a target DNA sequence that can be obtained from a primer extension product, when the products are analyzed using such a method.

For example, using the modified primers of the present invention, the read length of an exemplary extension segment would be determined as follows. A modified primer composed of nucleotides complementary to a DNA target and having a cleavable linkage between nucleotides 17 and 18 (e.g., the cleavable site is within one nucleotide from the 3' end of the primer) is first annealed to the target strand, extended enzymatically (e.g., with a polymerase or ligase), and the resulting primer extension product (subsequent to immobilization) is cleaved at the cleavable site to produce an extension segment containing only one nucleotide derived from the primer. In carrying out sizing of the extension products, the read length is equal to the total number of nucleotides detected (X) minus the one nucleotide derived from the second region of the primer, or X−1.

In contrast, prior to cleavage at the cleavable site, the product composed of the primer and the same set of extension segments would have a read length of X−18, where 18 equals the number of bases in the primer. Thus the amount of new or useful sequencing or size information for primer extension products obtained using the modified primers of the present invention is improved.

4.2 Oligonucleotide Compositions: Synthesis of Modified Primers 4.2.1 Feature of the Modified Primer The oligonucleotide primers of the present invention (i) are designed for optional attachment to a solid support in a manner that does not block the ability to extend the primer from its 3' end, and (ii) incorporate a cleavable moiety so that a 3' portion of the primer linked to an extension segment can be released from an upstream portion of the primer, 5' to the cleavable site. The upstream portion of the primer referred to herein as the first primer region, typically contains a significant number of the total number of nucleotides present in the primer, so that upon cleavage at the cleavable site, the amount of new fragment information for primer extension products is maximized.

The modified primers of the invention preferably contain an immobilization attachment site for attaching the primer to a solid support. For modified primers containing an internal immobilization attachment site (i.e. a site contained within the primer itself), the immobilization attachment site or IAS is generally separated from the cleavable site by at least three nucleotides. Upon selective cleavage of the cleavable site, a large portion of the primer fragment remains affixed to the solid support. This enables the release of primer extension products that contain about five or fewer base pairs of the primer sequence, to extend the useful size analysis range (e.g., increased read lengths), as illustrated in FIG. 15A and FIG. 15B.

FIG. 15A and FIG. 15B are mass spectra of products from primer extension reactions, illustrating the difference in fragment information obtained for cleaved primer extension segments according to the invention (FIG. 15B) versus non-cleaved full primer-extension segments (FIG. 15A). The details of the primer extension reactions and primer cleavage are described in Example 8. For sequencing applications, the modified primers can also provide more useful sequence information per fragment than extension products containing the entire primer.

Exemplary oligonucleotide sequences for use as primers or probes in the oligonucleotide compositions of the present invention typically have lengths ranging from about eight to thirty nucleotides, preferably between about ten or fifteen nucleotides to about twenty or twenty five nucleotides. Typically, the oligonucleotide sequences are complementary to a site upstream, relative to the 5' end, of the target sequence of interest, based on known sequence information for the target molecule. The oligonucleotide sequence may additionally contain a label in the releasable primer fragment (e.g., the second region), such as a radioactive or fluorescent tag, depending upon the method of sequence analysis employed.

The modified primers of the present invention, having a 5' end and a 3' end, are generally composed of two separate nucleotide regions. In one embodiment of the invention as illustrated in FIG. 5A, the two regions are connected by a cleavable site, as indicated by "X". The heterocyclic bases, adenine, thymine, guanine, and cytosine are commonly indicated in the figures by the symbol "B". The first region containing the 5' end of the primer, contains an immobilization attachment site, "I", for attachment to a solid support. In the embodiment shown in FIG. 5A, the modified primer is in immobilized form. The immobilization site may optionally be separated from the 5' end of the primer by a spacer arm, as indicated. Spacer arms for use in the present invention are generally six or more atoms in length.

The number of nucleotides in the first region will vary, but typically will be at least about three nucleotides. In a preferred embodiment, the first primer region contains a significant portion of the nucleotides (e.g., typically from about 3–20 nucleotides) composing the modified primer. As shown, the cleavable linkage, "X", is a 3'-5'-internucleotide cleavable site which connects the first region to the second region. The second region, which contains the 3' end of the primer, is composed of as few nucleotides as is feasible, although the number will vary depending on the primer employed. Preferably, the second region contains from zero to five nucleotides and the total number of nucleotides in the modified primer will be between about eight and thirty, and preferably between ten and twenty five. The 3' end of the modified primer serves as a priming site for enzymatic extension.

FIG. 5B illustrates an alternate embodiment of the present invention in which a biotin molecule is connected to the 5' end of a modified primer. The biotin is attached to the 5' end of the primer through an extended spacer arm which serves to reduce steric hindrance. Biotin, a relatively small vitamin molecule that binds with high affinity to both avidin and streptavidin, is one exemplary immobilization attachment site for use in the present invention. Biotinylated primers are available from commercial sources or may be synthesized by methods commonly employed in the art, typically utilizing a functionalized biotin reagent containing a reactive group suitable for coupling. As in FIG. 5A above, an internucleotide cleavable linkage separates the two regions of the modified primer. The second region contains a 3' end suitable for enzymatic extension, which may take place either prior to or after immobilization to a solid support.

FIG. 5C illustrates capture of the modified primer of FIG. 5B prior to enzymatic extension on an avidin-functionalized solid support. In this embodiment of the invention, the modified primer is immobilized via a high affinity interaction between avidin and biotin, as indicated by "I".

FIG. 5D illustrates an alternate embodiment of the invention in which the modified primer is attached to a solid support through an immobilization attachment site present as a substituent on one of the heterocyclic bases. As shown in FIG. 5D, the site for immobilization is an amino residue substituted at the position of a uracil (Dattagupta, 1989), and more specifically, is a 5-allylamino substituent. The amino group may be in protected form (e.g., trifluoroacetamido) prior to attachment to the solid support. As indicated, immobilization to the solid support is through an amide linkage, although any of a number of immobilization attachment linkages may be used, as will be described in more detail below. Coupling of the amino residue to a solid support is generally carried out by using an activated support material, such as an N-hydroxysuccinimide (NHS) ester functiionalized support.

In the embodiment shown in FIG. 5E, the immobilized primer is in a branched or "T"-configuration. As in the above embodiments, the modified primer contains two regions separated by a cleavable linkage indicated by "X". The first region contains the 5' end of the primer and an immobilization attachment site as described above. Referring to the design of a "T"-configured primer as shown in FIG. 5D, generally, a large portion of the nucleotides composing the modified primer and required for sequence specific target binding are located 5' of the "central" deoxyribose, indicated by an arrow. The second region contains the 3' end of the primer which serves as a priming site for enzymatic extension. In the exemplary modified primer shown, following hybridization to a target DNA, and enzymatic extension followed by denaturing and washing, selective cleavage of the cleavable site "X" releases the second region of the modified primer along with the extension product (e.g., the extension segment), while the first region containing a large portion of the nucleotides required for sequence specific target binding remains immobilized.

FIG. 5E illustrates an exemplary modified primer containing a terminal cleavage site, as indicated by an (X). In this embodiment of the invention, the cleavable linkage is represented by a ribose moiety, although any of a number of terminal cleavable sites may be employed. As shown, the modified primer is in immobilized form and contains an immobilization attachment site 5' of the cleavable site. The first region, contains the immobilization attachment site and the portion of the primer up to, but not including, the ribose. The ribose, or, alternatively, the cleavable site, represents the second primer region and also serves as a priming site for enzymatic extension.

Additional cleavable sites according to the invention include nucleotides cleavable by an enzyme such as a nuclease or glycosylase. FIG. 11 illustrates an exemplary cleavable primer containing. a restriction recognition site in the first primer region and a cleavable site in the second primer region. As can be seen in FIG. 11, the primer 75 contains two regions, a first 5' region containing a restriction endonuclease recognition sequence 73 and a second region 76 containing a cleavable site 77, downstream or 3' to the recognition sequence. Preferably, the restriction endonuclease cleavable site is located at or within about five nucleotides from the 3' end of the primer.

Representative restriction endonucleases for use in cleaving the modified primers of the invention include BpmI, BsgI, BseRI, BsmFI, and FokI, all of which make staggered cuts. A modified primer including a BpmI or BsgI recognition site contains (i) a first region which includes the recognition sequence, 5'-CTGGAG-3' or 5'-GTGCAG-3', respectively, and (ii) located 16 bases downstream from the last nucleotide of the recognition sequence, in the second primer region, is the cleavable site. A modified primer containing a BseRI or BsmFI recognition site, 5'GAGGAG-3' or 5'-GGGAC-3', respectively, contains a cleavable site located 10 bases downstream from the last nucleotide of the recognition sequence, while a primer containing a FokI recognition sequence (5'-GGATG-3') possesses a cleavable site 9 bases downstream from the last nucleotide of the recognition sequence.

Returning now to FIG. 11, the first region of the primer contains two separate domains. The first domain, 73, is composed of a series of bases recognizable by a restriction endonuclease as described above. The second domain of the first primer region, 76, is 3' to the restriction endonuclease recognition sequence and contains nucleotides complementary to a target DNA molecule 81 which acts as a template for enzymatic extension of the primer. The first domain of the first primer region 73 may optionally hybridize to the target molecule.

After carrying out a primer extension reaction to form a primer extension product 79, as will be described in more detail below, the double stranded product is denatured 85, and an oligonucleotide 83 complementary to both first 73 and second 76 domains within the first primer region is added to the reaction mixture, preferably in an excess amount. Typically, the complementary oligonucleotide 83 contains about 15–25 nucleotides, sufficient to allow restriction enzyme recognition and cleavage at the cleavable site. Preferably, the restriction endonuclease cleavable site is at or near to the 3' end of the primer.

The reaction mixture is then allowed to cool and reanneal 86. Due to the excess of complementary oligonucleotides 83 present, hybridization of the primer-extension product to the oligonucleotide complement is favored, as indicated at 87. Restriction endonuclease is then added to the mixture, as shown at 89, to promote cleavage at the cleavable site to release an extension segment 91, a small fragment of the complementary oligonucleotide 3' to the cleavable site 93, and a larger primer/complementary oligonucleotide fragment 5' of the cleavable site 95.

A primer of the type described above may also contain an immobilization attachment site (IAS) downstream from the cleavable site, to enable immobilization of the extension segment. Introduction of an IAS should not adversely affect (i) sequence-specific binding of the template to the modified primer, (ii) sequence-specific binding of the primer to the complementary oligonucleotide 83, (iii) enzymatic extension of the primer, or (iv) the cutting ability of the restriction enzyme. Generally, the extension product is immobilized and washed to remove reaction product (salts, enzymes, nucleotide fragments, reagents) prior to release and subsequent size and or sequence analysis. Other approaches include (i) the use of a primer or extension segment containing an immobilization attachment site, where, after enzymatically extending the primer and denaturing the double stranded product, the single stranded primer-extension product is captured via binding at the immobilization attachment site, followed by removal of the template and addition of complementary oligonucleotide 83, as described above, or (ii) the use of a template modified to contain an immobilization attachment site, for capturing the template either prior to or after enzymatic extension, prior to addition of oligonucleotide 83.

A variation of a cleavable primer of the type illustrated in FIG. 11 is shown in FIG. 16, where the first primer region contains a universal restriction recognition site within a hairpin (Szybalski, 1985). Referring now to FIG. 16, the cleavable site 127 is a class IIs restriction endonuclease cleavable site, where the double stranded enzyme recognition sequence 129 is located in the first primer region (i.e. upstream of the cleavage site), and the first primer region contains a 5' hair-type (self-complementary double stranded) domain. The 5' hair domain 131 includes the double stranded recognition site 129 for the restriction enzyme. The second (single stranded) primer region contains (i) the cleavable site (i.e. restriction endonuclease cut site) and (ii) is composed of nucleotides complementary to a single stranded target 133, thus serving as a priming site for enzymatic extension. Following enzymatic extension of the primer (shown at 135), the product 137 is cleaved 139 by treatment with a suitable class IIs restriction endonuclease to release fragments 141 and 143, followed by denaturation to release the single stranded extension segment for subsequent analysis, i.e. by mass spectrometry. As indicated in the figure at 145, the template may optionally be attached to a solid phase support at any stage during the process.

In some instances, the cleavable site is a nucleotide capable of blocking or terminating 5' to 3' enzyme-promoted digestion by an enzyme having 5' to 3' exonuclease activity, such as gene 6 exonuclease, ExoVIII, RecJ, and spleen phosphodiesterase II. Such "blocking" nucleotides include nucleotides containing phosphorothioate, borano-phosphate, or peptide group as will be described below. In a prior extension reaction utilizing a modified primer containing a blocking nucleotide as the cleavable site, following a primer extension reaction, the resulting product, composed of (i) a modified primer containing a blocking nucleotide, and (ii) an extension segment, is treated with a release such as an exonuclease having a 5' to 3' exonuclease activity. Nuclease treatment typically results in digestion of the first region of the primer to generate an extension segment composed of nucleotides downstream (i.e. 3') of the cleavable site.

In all of the exemplary embodiments described above, cleavage of the cleavable site results in the release of newly synthesized primer extension products containing little or none of the nucleotide bases originally present in the modified primer.

4.2.2 Introduction of the Cleavable Site

The cleavable site (composed of a modified nucleotide) is typically introduced into an oligonucleotide probe by using one of following synthetic approaches although many other approaches as may be contemplated by those of skill in the art are also encompassed by the present invention. Depending upon the choice of cleavable site to be introduced, either a functiionalized nucleotide or a modified nucleotide dimer (or larger multimer) may first be prepared, and then selectively introduced into a growing oligonucleotide fragment during the course of primer synthesis. The primer containing the cleavable site may be prepared using solution synthesis, or preferably, employing automated solid phase synthesis conditions using a DNA synthesizer.

In forming a modified dimer, two suitably protected nucleotides are coupled to each other to form a modified 3'-5'-internucleotide linkage. The dimer containing the cleavable site (or a protected form thereof) is then incorporated into the oligonucleotide primer during synthesis to form a modified oligonucleotide containing a cleavable site. The cleavable site is chemically cleavable under select conditions but is stable under standard solid phase DNA synthesis, solid support attachment, primer extension and hybridization conditions.

Alternatively, functionalization is carried out on a single nucleotide to introduce a reactive group suitable for forming a cleavable site upon reaction with a second nucleotide molecule or during primer synthesis.

Although functionalization may take place at sites within the base or the sugar of the nucleotide, typically, modification will be carried out to result in an oligonucleotide primer containing a specific cleavable site in place of one of the phosphodiester linkages of the resulting polymer or oligonucleotide. Preferred non-internucleotide locations for modification or introduction of a cleavable site include C(5) of thymine and N(4) of cytosine, as these two base sites are readily chemically manipulated without preventing base pairing.

Figure 1A:
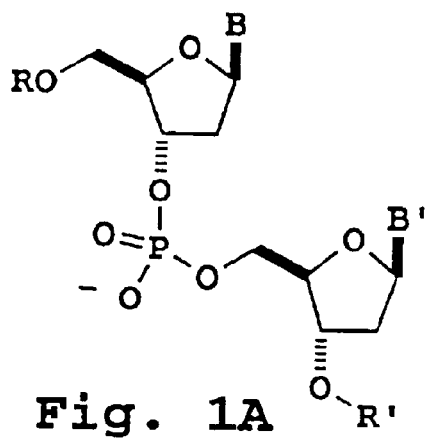
Figure 1B:
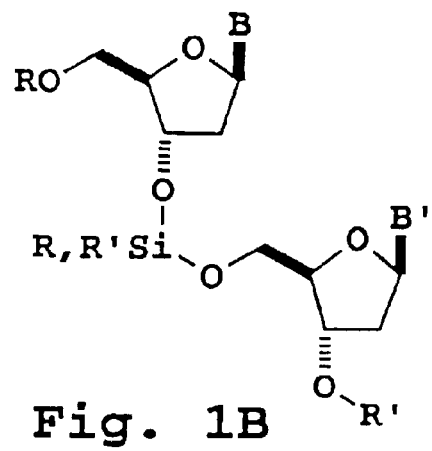
Figure 1C:
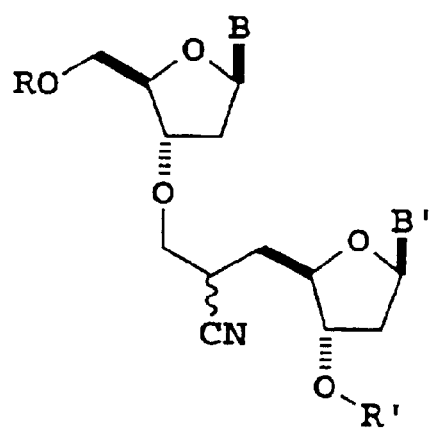
Figure 1D:
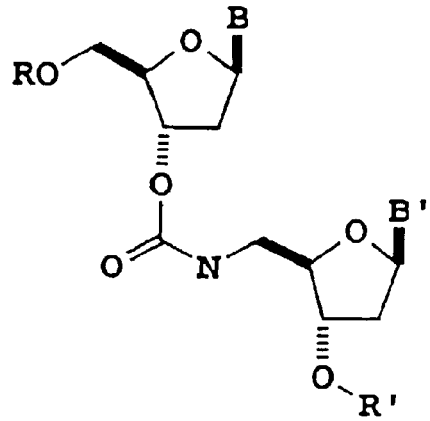
Figure 1E:
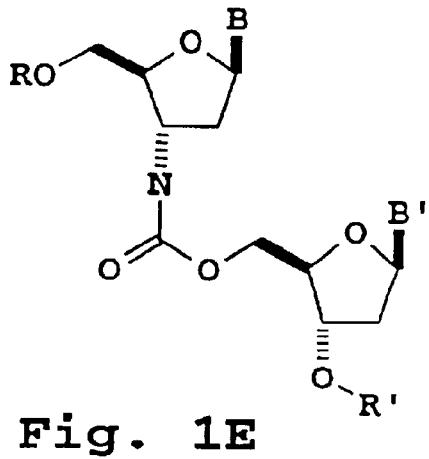
Figure 1F:
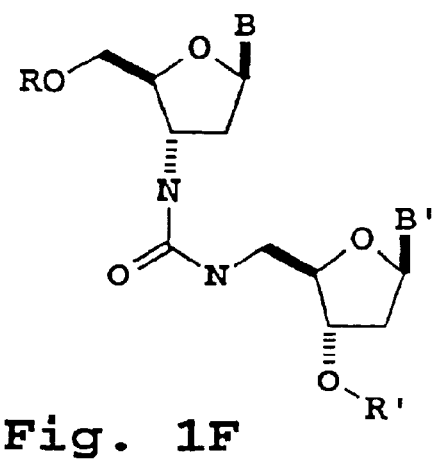
Figure 1G:
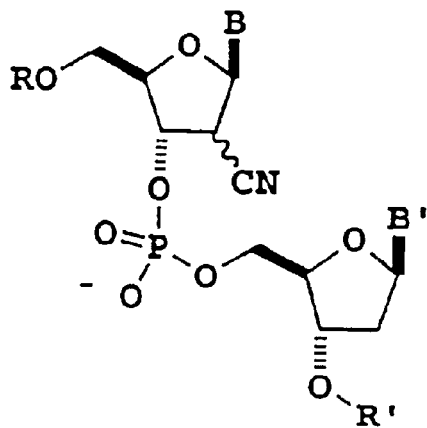
Figure 1H:
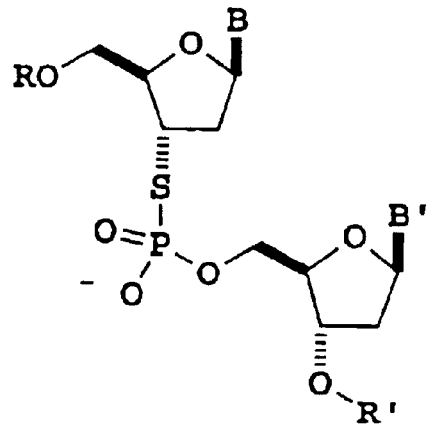
Figure 1I:
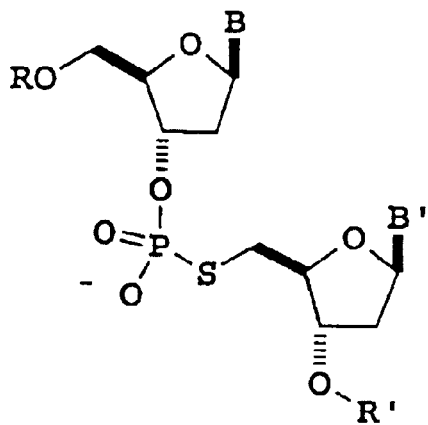
Figure 1J:
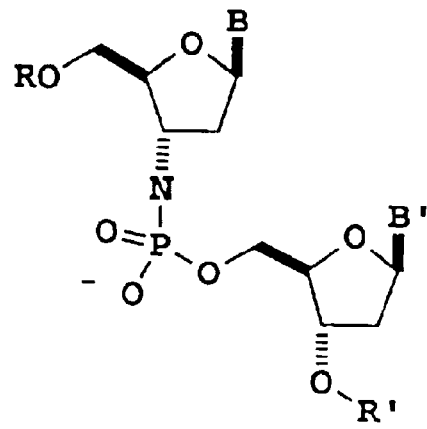
Figure 1K:
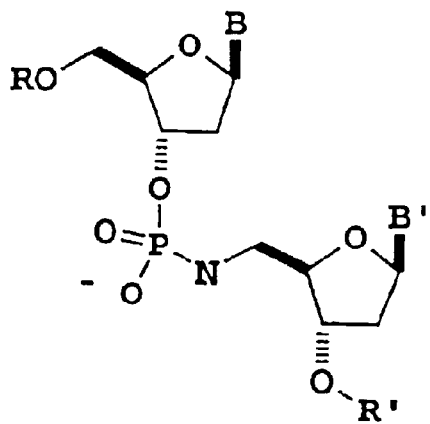
Figure 1L:
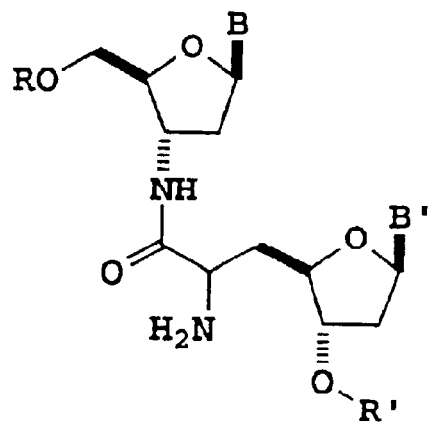
Figure 1M:
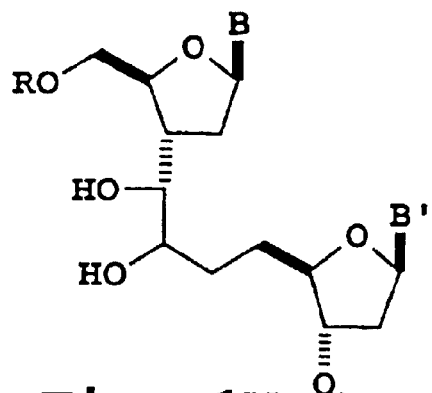
Figure 1N:
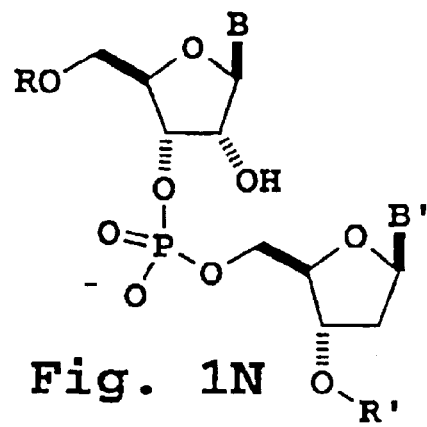
Figure 1O:
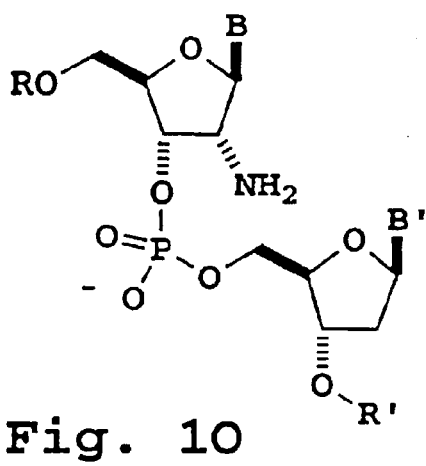
Figure 1P:
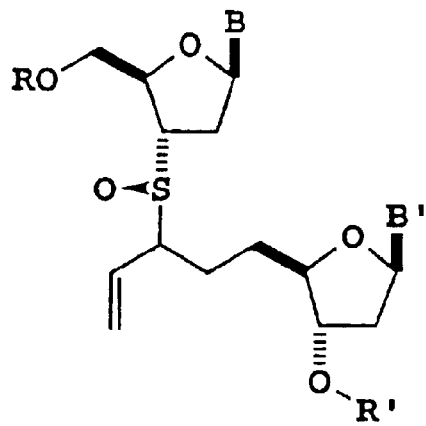
Figure 1Q:
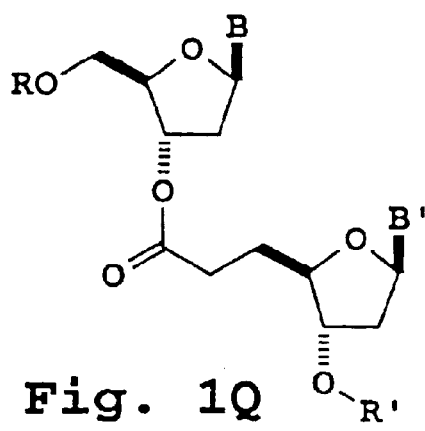
Figure 1R:
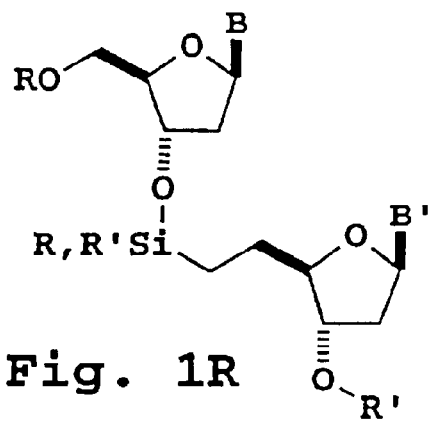
Figure 1S:
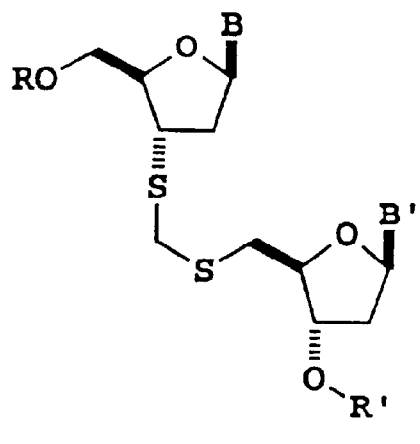
Figure 1T:
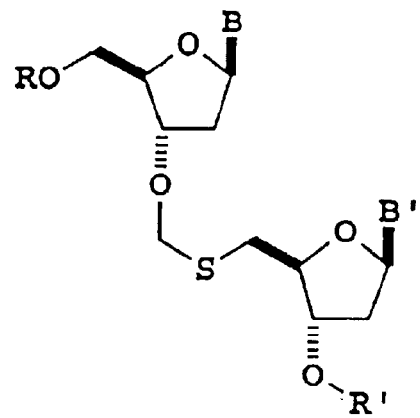
Figure 1U:
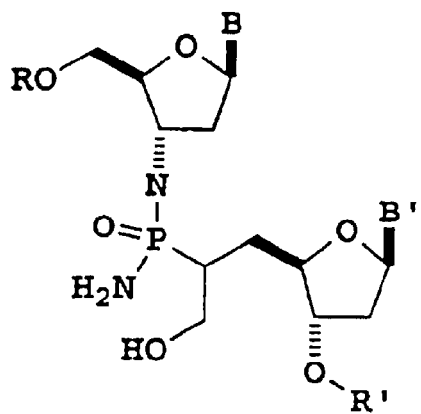
Figure 1V:
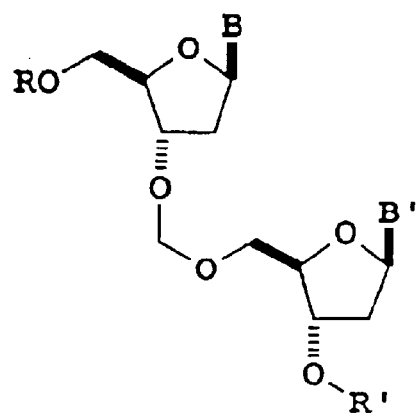
Figure 1W:
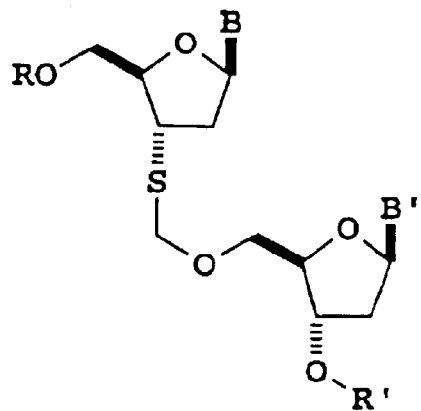

A number of exemplary internucleoside cleavable sites for use in the oligonucleotide composition of the present invention are illustrated in FIGS. 1B–1W. FIG. 1A is an illustration of an unmodified, native 3,-5,-phosphodiester linkage. A cleavable site or linkage for use in the invention is one which may be introduced at a specific position within the oligonucleotide sequence, preferably at or within about five nucleotides from the 3' end of the primer, and is selectively cleaved under conditions which do not permit cleavage of the immobilization attachment site. In one preferred embodiment, the cleavable site is located at the 3' end of the primer The cleavable linkage should also be one that is chemically accessible.

Chemically cleavable internucleotide linkages for use in the present invention include but are not limited to the following, as illustrated in FIGS. 1B–1W, respectively: dialkoxysilane, FIG. 1B; β-cyano ether, FIG. 1C; 5'-deoxy-5'-aminocarbamate, FIG. 1D; 3'deoxy-3'-aminocarbamate, FIG. 1E; urea, FIG. 1F; 2'cyano-3',5'-phosphodiester, FIG. 1G; 3'-(S)-phosphorothioate, FIG. 1H; 5'-(S)-phosphorothioate, FIG. 1I; 3'-(N)-phosphoramidate, FIG. 1J; 5'-(N)-phosphoramidate, FIG. 1K; α-amino amide, FIG. 1L; vicinal diol, FIG. 1M; ribonucleoside insertion, FIG. 1N; 2'-amino-3',5'-phosphodiester, FIG. 1O; allylic sulfoxide, FIG. 1P; ester, FIG. 1Q; silyl ether, FIG. 1R; dithioacetal, FIG. 1S; 5'-thio-formal, FIG. 1T; α-hydroxy-methyl-phosphonic bisamide, FIG. 1U; acetal, FIG. 1V; and 3'-thio-formal, FIG. 1W. Other chemically cleavable linkages include methylphosphonate and phosphotriester. Cleavable linkages suitable for non-chemical cleavage methods such as photolysis or thermolysis include nitrobenzyl ether (NBE), cis-syn thymidine dimer (Nadji et al, 1992), and cyclohexene.

Nucleoside dimers containing the cleavable linkages illustrated in FIGS. 1B–1W are synthesized using standard nucleic acid chemistry known to one of skill in the art (Hobbs, 1990; Townsend et al., 1986). Alternatively, one may directly synthesize a modified nucleoside containing either a 5'-or 3'-reactive group (or protected form thereof) for use in standard solid phase synthesis to introduce the desired cleavable linkage. 2'-Functionalized nucleosides are typically prepared from the corresponding ribonucleoside starting materials. An internucleotide β-cyano ether linkage, as shown in FIG. 1C, may be formed by reaction of a suitably protected nucleoside with a 5'-(2-cyanoallyl) functionalized 3'-phosphoramidite. Selective cleavage is effected by a β-elimination reaction upon treatment with base, promoted by the presence of the β-cyano substituent. A nucleoside dimer containing a 3'-(O)-carbamate internucleoside bond is prepared by any of a number of synthetic approaches including reaction between the corresponding 3'-acyl chloride and a 5'-amino-modified nucleoside. Alternatively, a 3'-modified isocyanate nucleoside is prepared and subsequently reacted with the 5'-hydroxyl of a suitably protected nucleoside. A nucleoside dimer containing a 5'-(O)-carbamate cleavable linkage is prepared from the imidazole carbamate precursor.

Oligonucleosides containing methyl phosphonate linkages are prepared using solid support based synthesis with phosphonamidite reagents used in place of the standard phosphoramidites (Agrawal and Goodchild, 1987). Phosphotriesters are somewhat labile under basic deblocking conditions, however, this cleavable group may be introduced into an oligonucleotide backbone by using mild reaction conditions or more labile amine protecting groups (Miller et al., 1971). Methanol or ethanol in the presence of tosyl chloride is used to esterify the internucleoside phosphate group (Moody et al., 1989); methyl methanesulfonate may also be used as a methylating agent (Koole et al., 1987).

Preferred cleavable sites for use in the modified oligonucleotide composition include dialkoxysilane, ribose, 3'-and 5'-phosphoramidate, and 3'-and 5'-phosphorothioate.

In one embodiment of the present invention, the cleavable site contained in the modified oligonucleotide primer is dialkoxysilane (Ogilvie et al., 1986; Seliger et al., 1987; Cormier et al., 1988). Synthesis of a primer containing a dialkoxysilane internucleotide linkage is described in Example 1A. Although the preparation of a diisopropylsilyl-linked dinucleoside is described in Example 1A, alkyl groups for use as substituents on silicon are not limited to isopropyl and may be either straight chain or branched alkyl groups. Further, the two alkyl substituents on silicon may be identical, as in the case of diisopropylsilyl, or may be different. A variety of dialkylsilylating reagents are available from Petrarch Systems, Bertram, Pa.

In the synthetic approach outlined in Example 1A, a reactive 3'-O-silyl ether intermediate is first prepared, followed by formation of a nucleoside dimer containing a 3'-5'-diisopropylsilyl internucleoside bridging group. Formation of a 3'-silyl triflate intermediate is carried out by reacting a 5'-(O)-dimethoxytrityl(DMT)-protected nucleoside, such as 5'-(O)-DMT-thymidine or the N-protected nucleosides N6-benzoyl-2'-deoxy-5'-(O)-DMT-adenosine, N4-benzoyl-2'-deoxy-5'-(O)DMT-cytidine, or N2-isobutryl-2'-deoxy-5'-(O)-DMT-guanosine, with an O-protected silane reagent.

In Example 1A, the protected nucleoside is treated with the reactive silane, bis(trifluoromethane-sulfonyl)diisopropylsilane, in the presence of the sterically hindered base, 2,6-di-tert-butyl-4-methylpyridine, to promote formation of the desired 3'-(O)-diisopropylsilyl triflate intermediate. Use of a bulky base such as the tri-substituted pyridine reagent helps to prevent formation of the undesired symmetrical nucleoside dimer formed by condensation of unreacted nucleoside with the triflate intermediate (Saha et al., 1993).

Following introduction of the desire 3'-0-silyl ether group, the 3'-O-diisopropylsilyl triflate intermediate is reacted with unprotected nucleoside to form the desired nucleoside dimer containing a 3'(O),5'(O)-dialkoxysilane cleavable site. The protected dimer may then be further functionalized, for instance, by conversion of the 3'-hydroxyl to the corresponding 2-cyanoethyl-N,N-diisopropylphosphoramidite for use in automated solid phase synthesis utilizing standard phosphoramidite chemistry to provide the desired primer sequence. Selective cleavage of the dialkoxysilane site is effected by treatment with fluoride ion (Corey and Snider, 1972).

Another preferred selectively cleavable functionality for use in the invention is phosphorothioate. The preparation of primers containing a 3'(S)-phosphorothioate or a 5'(S)-phosphorothioate internucleotide linkage is described in Examples 1B and 1C, respectively. In accordance with the modified oligonucleotide composition of the invention, the phosphorothioate internucleotide linkage is selectively cleaved under mild oxidative conditions (Cosstick et al., 1989).

In one synthetic approach for preparing primers containing a 3'(S)-phosphorothioate cleavable site as described in Example 1B, a protected 3'-thio-substituted nucleoside starting material, such as 5-O-MMT-3'-S-benzoyl-3'-thymidine (Cosstick et al., 1988), is first deprotected by treatment with base to form the debenzoylated thiol, 5'-(O)-MMT-3'-thiothymidine, followed by conversion to the corresponding reactive thiophosphoramidite by reaction with 2-cyanoethyl-N,N-diisopropylaminophosphormonochloriditie. The reactive thiophosphoramidite is coupled to a second nucleoside molecule to form the corresponding thiophosphite dimer, followed by oxidation of the phosphorus center to form the fully protected 3'-(S)-phosphorothioate-linked dimer.

In order to promote coupling of the thiophosphoramidite to a second nucleoside molecule such as 3'-O-acetylthymidine and prevent undesired self-condensation side reactions, an acidic activating agent, 5-(para-nitrophenyl)tetrazole, is used. The thiophosphite dimer is oxidized with a suitable oxidant such as tetrabutylammonium oxone or tetrabutylammonium periodate to form the fully protected (P-(O)-2-cyanoethyl-3'-acetyl) dimer containing a protected form of the desired internucleoside linkage. Deprotection is readily carried out under standard conditions as described in Example 1B. As discussed above, the nucleoside dimer, containing a 3'-(S)phosphorothioate cleavable linkage may be readily incorporated into an oligonucleotide primer using standard solid phase phosphoramidite chemistry.

Alternatively, one may use the reactive thiophosphoramidite directly to introduce the desired 3'-(S)-phosphorothioate linkage into an oligonucleotide primer during solid phase synthesis. For introduction of a functionalized nucleoside containing a 3'-(S)-thiophosphoramidite during solid phase synthesis on controlled pore glass, during the coupling cycle for introducing the thio-modified nucleoside, the thio-modified nucleoside, dissolved in acetonitrile saturated with 5-(para-nitrophenyl)tetrazole, is injected into the column containing the solid support, and the coupling efficiency is monitored by release of trityl cations.

After preparing the desired immobilized, cleavable primer in accordance with the present invention, and carrying out the desired hybridization and primer extension reactions, the phosphorothioate internucleotide site is cleaved by treatment with a mild oxidizing agent such as aqueous silver nitrate.

Preparation of the corresponding 5-(S)-phosphorothioate modified oligonucleotide is carried out in a somewhat different fashion than that described above for the 3'-(S)-phosphorothioate and is described in detail in Example 1C. The approach makes use of a key 5-thio-modified nucleoside intermediate for incorporation of the desired 5'-(S)-phosphorothioate cleavable linkage during solid phase oligonucleotide synthesis (Mag et al., 1991; Sproat et al., 1987).

Synthesis of the nucleoside building block containing a protected 5'-thio group is carried out by first preparing the 5'-tosylate of thymidine by treatment with tosyl chloride, followed by conversion of the 5'-tosylate to 5'-(S-trityl)-mercapto-5'-deoxythymidine. 5'-Tosyl-thymidine is converted to 5'-(S-trityl)-mercapto-5'-deoxythymidine by treatment with a five-fold excess of sodium tritylthiolate, which is prepared in-situ by deprotonation of tritylmercaptan with sodium hydroxide. In the above synthetic step, a sulfur atom is introduced into the 5'-position of a nucleoside, forming the S-trityl precursor of the desired key intermediate. Subsequent phosphitylation at the 3'-position with 2-cyanoethoxy-bis-(N,N-diisopropylamino)phosphine in the presence of tetrazole results in the desired functionalized nucleoside, 5'-(S-trityl)-mercapto-5'-deoxythymidine-3'-O-(2-cyanoethyl-N,N-diisopropylamino)phosphite.

The 5'-(S)-protected nucleoside intermediate is introduced into an oligonucleotide primer using standard solid-phase phosphoramidite chemistry by first coupling it to a deprotected polymer-bound oligonucleotide. The phosphite linkage is then oxidized with aqueous $I_2$, and the S-trityl group is cleaved with silver nitrate and reduced with dithiothreitol to form a reactive thiol. The thiol is then coupled to a 2'-deoxynucleoside-3'-phosphoramidite, followed by oxidation of the thiophosphite linkage to yield the desired 5'-phosphorothioate cleavable site.

Selective cleavage of the phosphorothioate site may also be effected by treatment with an aqueous solution of either silver nitrate ($AgNO_3$) or mercuric chloride ($HgCl_2$).

Another functional group for use as a cleavable site in the modified oligonucleotide composition of the invention is phosphoramidate. Oligonucleotides bearing phosphoramidate internucleotide linkages can be prepared chemically by standard, solid phase DNA synthesis (Bannwarth, 1988). Preparation of primers containing a 5'-(N)-phosphoramidate internucleotide linkage is described in Example 1D. In the synthetic approach described in Example 1D, a 5'-amino-modified nucleoside is either purchase commercially or synthesized by conversion of the 5'-hydroxyl group to the corresponding azide, followed by reduction over a palladium/carbon catalyst (Yamamoto et al., 1980).

The 5'-amino group is then protected by treatment with 4-methoxytritylchloride, followed by reaction with bis (diisopropylammonium)tetrazolide and (2-cyanoethoxy)bis (diisopropylamino)phosphine to form the corresponding 3'-(2-cyanoethyl) -N,N-diisopropylphosphoramidite-functionalized nucleoside. This reactive nucleoside, containing a 5'-protected amino function, is then selectively introduced into an oligonucleotide fragment during standard solid phase DNA synthesis utilizing phosphoramidite chemistry, to form the desired 5'-phosphoramidate bond. Selective cleavage of the phosphoramidate bond is carried out under mild acidic conditions, such as by treatment with 80% acetic acid. Phosphoramidate linkages are more labile in the ribo series than in the deoxyribo series (Tomasz et al., 1981).

Another functional group for use as a cleavable site in the present oligonucleotide composition is ribose. Modified primers containing a cleavable ribose are described in Examples 3–5. Ribose, containing suitable O-protecting groups, is selectively introduced into a growing oligomer fragment during automated solid phase synthesis using standard phosphoramidite chemistry. Selective cleavage is carried out by treatment with dilute ammonium hydroxide, as described in Examples 3 and 5.

4.2.3 Attachment to Solid Support

In accordance with one aspect of the invention, the oligonucleotide primers (i) may be designed for attachment to a solid support in a manner that does not block the ability to extend the primer from its 3' end, and (ii) incorporate a cleavable moiety so that a 3' portion of the primer (linked to an extension product) can be released from an optionally immobilized 5' portion.

The oligonucleotide primers of the invention are preferably designed for binding to a solid support material directly, through an intervening spacer arm, or by specific hybridization to an intermediary oligonucleotide which is bound to a solid support (SPBIO). Immobilization may occur at a location upstream (i.e. 5' to) or downstream (i.e. 3' to) of the cleavable site.

Attachment to a solid phase may also take place via an attachment site (i) contained within a nucleic acid extension segment resulting from an enzymatic extension reaction, or, (ii) contained within a target nucleic acid.

The immobilization attachment site can be a select functional group for covalent bonding to a solid support, such as those representative functional groups shown in FIGS. 2A–2K, and FIG. 2M. The immobilization attachment site can also be a ligand such as biotin, for attachment via a high-affinity non-covalent interaction with a solid support.

Further, the immobilization attachment site can also be composed of a series of bases complementary to an intermediary oligonucleotide bound to a solid support, as illustrated in FIG. 8 and FIG. 9.

Referring now to FIG. 8, a primer having a cleavable site 17 as described above is (i) hybridized to a single stranded, target DNA sequence 21 utilizing conditions under which the target will anneal stably to the primer, and (ii) enzymatically extended to form an extension segment 19. The extension product is then exposed to an intermediary oligonucleotide which is bound to a solid support 23. The intermediary oligonucleotide is complementary to all or at least the first region of the primer.

In the embodiment illustrated in FIG. 8, the sequence of the intermediary oligonucleotide is homologous with at least a portion of the target molecule 21, so that both the intermediary oligonucleotide and the target are competing to hybridize to an overlapping region of the primer. In instances in which the sequence of the extension product is known, the sequence of the intermediary oligonucleotide may be designed to be complementary to a portion of the extension segment rather than to the primer, or, to a region containing portions of both the primer and the extension segment.

In employing this approach for immobilization, the concentration of target molecule relative to intermediary oligonucleotide is preferably reduced in order to favor hybridization of the primer extension product to the intermediary oligonucleotide. Hybridization of the extension product to template is thermodynamically favored, since the template is capable of hybridizing to the full length of the extension product. The concentration of target nucleic acid can be reduced by a number of methods, including specific chemical or enzymatic digestion which leaves the primer extension product intact.

Selective digestion of the template may be effected by any of a number of methods, including the following: (i) use of a deoxyuridine-containing template; (ii) use of an RNA template to provide DNA extension products; (iii) use of a template containing modified internucleoside linkages; or (iv) exonuclease-promoted digestion of template. Each is described in greater detail below.

In employing the first approach, a nucleic acid fragment which has been site selectively modified (Longo et al., 1990) to contain deoxyuridine in place of deoxythymidine is used as a template for the primer extension reaction. Following enzymatic extension, the template-containing reaction mixture is treated with uracil DNA glycosylase (Amersham Life Sciences, Arlington Heights, Ill.) to fragment the template molecule at positions modified to contain deoxyuridine. Uracil DNA glycosylase excises deoxyuracil from dU-containing DNA by cleaving the N-glycosidic bond between the uracil base and the sugar phosphate backbone.

In the second approach, an RNA template is used to provide DNA extension products. The template is then selectively removed by digestion using RNase, such as RNase A.

Alternatively, as indicated by (iii) above, a template molecule containing modified internucleoside linkages such as a phosphoramidate or phosphorothioate is used. Following extension of the primer, the template is digested by chemically-promoted cleavage at the modified linkage positions. The choice of template-modified internucleoside linkage and template-digestion reagent will depend upon the type of cleavable site present in the primer. Digestion of template is typically carried out under conditions which leave the primer cleavable site intact. Cleavage of a phosphorothioate linkage (5'-(O)—P(S)O$_2$) can be effected by treatment with glycidol or iodoethanol (Olsen, 1992), while selective cleavage of a phosphoramidate bond is typically carried out under mild acidic conditions, such as by treatment with 80% acetic acid.

In utilizing exonuclease-promoted digestion of template (as indicated by (iv) above), the primer extension product is modified to contain a suitable exonuclease-resistant blocking group as described previously. Upon exonuclease treatment with either a 3'-5' specific or a 5'-3' specific exonuclease, the "protected" prime extension product then remains intact, due to the presence of the blocking group. In utilizing a 3'-5' exonuclease (e.g. snake venom phosphodiesterase or exonuclease III), a suitable blocking group is placed at the 3' terminus of the extension product to prevent enzyme-promoted degradation.

The relative concentration of template to solid-bound intermediary oligonucleotide, can also be minimized, for example, (i) by performing cycle synthesis procedures with limited amounts of template (e.g., cycle sequencing or strand displacement amplification), or (ii) adding a large excess (e.g., 10 to 100-fold) of intermediary oligonucleotide to the reaction mixture.

Returning now to FIG. 8, under conditions which favor hybridization. of the primer extension product to the solid phase bound intermediary oligonucleotide, the primer extension product is immobilized by hybridization to the solid phase bound intermediary oligonucleotide 23 to form captured product 27 and free (i.e. single stranded template). The 5' end of the solid phase bound intermediary oligonucleotide may terminate before or after the cleavable site of the modified primer. After immobilization as described above, excess reaction products are removed by washing 29 to provide a purified immobilized product 31. The immobilized product is cleaved 33 to release the extension segment 35 for subsequent analysis.

In accordance with the present invention, immobilization of a cleavable extended primer by hybridization to an intermediary solid phase bound oligonucleotide is described in Example 6.

Briefly, a modified M13 reverse primer containing a 5'-(S)-thymidine cleavable group (SEQ ID NO:12) was (i) hybridized to a single stranded target, and (ii) enzymatically extended in the presence of dideoxythymidine to produce a set of dideoxythymidine-terminated extension fragments at a 8:1 ratio of primer to template. The single stranded extension products were then annealed to an intermediary oligonucleotide (SEQ ID NO:13) complementary to the M13 reverse primer and biotinylated at the 3' end. The extension product-intermediary oligonucleotide hybrids were then immobilized by addition of streptavidin-coated magnetic beads, washed, and the extension product released by silver-nitrate promoted cleavage of the 5'-(S)-thymidine cleavable group. The extension segments were analyzed by MALDI time-of-flight mass spectrometry, as shown in FIG. 13. As can be seen, extension segments with read lengths up to at least about 33 base pairs can be detected with good resolution.

In a variation of the above approach as shown in FIG. 9, the primer 39 is designed to contain an immobilization attachment site 38 contained in the first primer region composed of a series of bases complementary to an intermediary oligonucleotide bound to a solid support. However, in this embodiment, the intermediary oligonucleotide does not share homology with the template molecule 45, so that the intermediary oligonucleotide and template do not compete with one another for hybridization to the primer. As illustrated in FIG. 9, following enzymatic extension to form extension segment 43, the primer is immobilized by specific hybridization to the solid phase bound intermediary oligonucleotide 37. This design of primer, template, and intermediary oligonucleotide allows for simultaneous, non-competitive hybridization of the primer to both the template and intermediary oligonucleotide. The solid phase bound extension product is washed and the template is eliminated 47 to provide a purified immobilized product 49, which is then cleaved 51 at cleavable site 41 to release extension segment 53 for subsequent size and/or sequence analysis as described for FIG. 8 above.

Alternatively, a primer of the present invention may be bound to a solid phase via hybridization to a target nucleic acid which is immobilized, as shown in FIG. 10. In utilizing this approach, the target molecule 61 acts as both a template for enzymatic extension of the primer 55 and as an intermediary for solid phase binding of the primer. The template can be attached to the solid phase either before or after carrying out enzymatic extension of the primer to form the extended primer segment 59. As has been described, immobilization of the primer extension product allows for ready removal of excess enzyme, salts, etc., 63, to provide a purified immobilized primer extension product 65. Prior to analysis, the extended primer is denatured from the template 67 and released into solution. Cleavage at the cleavable site 57 promotes release of an extension segment 71 and a fragment composed of the first primer region 69. Depending upon the design of the primer and the mode of product analysis, the presence of primer fragment 69 may adversely impact the quality of the subsequent product analysis. In these instances, the same methods used to eliminate template, as described above, may be used to eliminate fragment 69. In cases in which the extension segment is sized by mass spectrometry, the mass of fragment 69 can, in some instances, be selected to avoid interference with product peaks in the resulting mass spectra, and may also be used to provide an internal mass standard.

Upon attachment of the immobilization attachment site to a solid support, the resulting immobilization linkage is generally one which remains stable under the conditions employed for cleaving the cleavable site and does not inhibit base pair hybridization nor block the ability to extend the primer from its 3' end.

In the modified primer of the invention, the immobilization attachment site is typically separated from the cleavable site by at least three nucleotides. In a preferred embodiment, upon selective cleavage of the cleavable site, a large portion of the primer fragment remains affixed to the solid support. This enables the release of primer extension products that typically contain about five or fewer base pairs of the primer sequence, to provide more useful sequence information per fragment than extension products containing the entire primer.

The modified primers of the present invention may, for example, be used for detecting a genetic disorder for which the nucleotide sequence of both the wild type and mutant alleles are known. A modified primer for this purpose will have a 5' end and a 3' end and contain from about 8–30 base pairs complementary to the gene sequence upstream from the known mutation site. Preferably, the 3' end of the primer is complementary to a site upstream from the known mutation region by at least about ten base pairs, to provide verifying sequence information on either side of the mutation region.

In accordance with one aspect of the invention, the modified primer also contains (i) an immobilization site for attachment to a solid support and (ii) a cleavable site. One primer design according to the present invention is one in which the immobilization site is located 5' of the cleavable site which is preferably located at or within about five base pairs from the 3' end of the primer.

This modified primer is then used as a probe to distinguish the presence of DNA containing the mutant sequence of interest. The primer is (i) hybridized to an unknown, single stranded, target DNA sequence utilizing conditions under which both the mutant and the normal sequences will anneal stably to the primer, and (ii) enzymatically extended. Primer immobilization may optionally take place either before or after chain extension. Following chain extension and release of the immobilized primer extension products by selective cleavage of the cleavable linkage, the primer extension products are analyzed to determine the sequence across the known mutation region and identification of the genetic disorder, if present.

An exemplary modified primer containing 20 deoxy-nucleotide residues and specific for its ability to detect a known genetic disorder is shown in FIG. 6A and FIG. 6B. As indicated, the modified primer contains a first region containing an immobilization attachment site, "I", that is 5' of the cleavable site, "X", and consists of a total of 16 nucleotide residues. The second region contains the 3' end of the primer and contains 4 nucleotides (C-T-G-C). The cleavable linkage, X, connects the first and second regions.

In illustrating this aspect of the invention, the modified primer as shown in FIG. 6A (top) and having the sequence presented as SEQ ID NO:2, is first hybridized to a single stranded DNA target having the sequence presented SEQ ID NO:3, as shown in FIG. 6A. Typically, the hybridization medium contains (i) denatured, unknown (target) DNA from a human or other biological source, (ii) the modified probe, and (iii) annealing buffer, such as 5X "SEQUENASE" Buffer (200 mM Tris-HCl, pH 7.5, 100 mM $MgCl_2$, 250 mM NaCl) (United States Biochemical Corporation, Cleveland, Ohio). The annealing reaction is carried out by warming the above mixture to 65° C. for two minutes, and then allowing the mixture to cool slowly to room temperature over a period of about thirty minutes (Maniatis et al., 1982; Ausubel et al., 1989).

Following hybridization, the modified primer is extended on the single stranded template with deoxynucleotides and randomly terminated with dideoxynucleosides using DNA polymerase (e.g., "SEQUENASE" DNA Polymerase, Version 1.0 or 2.0) to perform DNA synthesis (Primings et al., 1980; Sanger, 1975). As indicated in FIG. 6A, extension occurs from the 3' end of the modified primer. The primer extension products are denatured from the target, typically using heat or a chemical denaturant such as formamide, to provide a mixture of both primer extension products and target DNA. (See, for example, "PROTOCOLS FOR DNA SEQUENCING WITH SEQUENASE T7 DNA POLYMERASE", Version 1.0 or 2.0, 4th ed., United States Biochemical, or "CIRCUMVENT THERMAL CYCLE DIDEOXY DNA SEQUENCING KIT INSTRUCTION MANUAL", New England Biolabs, Inc., Beverly, Mass.).

As shown in FIG. 6B, the primer extension products are then bound to the solid support at the immobilization attachment site, although immobilization may optionally be carried out prior to enzymatic extension and/or denaturation. By immobilizing the extended primers, the target DNA strands which remain free in solution are readily removed, along with excess reagents, ions, enzymes and the like, in a series of wash steps. Generally, the solid substrate is washed with large volumes of a wash solution (e.g., 10 mM Tris HCl, 1 mM EDTA; or pure water) at room temperature.

The solid particles, containing immobilized primer extension products and free of impurities, are then submitted to conditions effective to selectively cleave the cleavable site while maintaining the first primer region having the sequence presented as SEQ ID NO:4 affixed to the solid support as shown in FIG. 6B. As indicated in the particular embodiment illustrated in FIG. 6B, selective cleavage results in release of primer extension products containing only four nucleotides from the original modified primer. The supernatant containing the released extension segments is suitable for subsequent analysis.

Immobilization simplifies purification of the primer extension products for subsequent analysis. As discussed above, undesirable enzymes, salts, reagents, and sequencing targets are washed away prior to selective cleavage of the extension product.

In immobilizing the modified primers of the present invention, the first region of the primer may be attached to the solid support material either prior to or after introduction of the cleavable site. Any of a number of methods commonly employed in the art may be utilized to immobilize an oligonucleotide on a solid support (Saiki et al., 1989; Zhang et. al., 1991; Kremsky et al., 1987; Van Ness et al., 1991; Ghosh et al., 1987; Gingeras et. al., 1987; Khrapko et al., 1991). Solid support materials for use in the invention include cellulose, nitrocellulose, nylon membranes, controlled-pore glass beads, acrylamide gels, polystyrene matrices, activated dextran, avidin/streptavidin-coated polystyrene beads, agarose, polyethylene, functionalized plastics, glass, silicon, aluminum, steel, iron, copper, nickel, silver and gold.

Some substrates may require functionalization prior to attachment of an oligonucleotide. Solid substrates that may require such surface modification include aluminum, steel, iron, copper, nickel, gold, and silicon. In one approach, the solid substrate material is functionalized by reaction with a coupling agent, such as zircoaluminate.

Zircoaluminates generally contain both oxo and hydroxy bridges and are characterized by high thermal and hydrolytic stability. Such compounds, due to their highly metallic nature, are particularly reactive with metal surfaces such as the metallic solid supports described above. Bi-functional zircoaluminates containing a variety of organofunctional groups are commercially available (e.g., "MANCHEM" Zircoaluminates, Rhône-Poulenc Latex & Specialty Polymers, Cranbury, N.J.).

Upon attachment to a solid support, the oligonucleotide, typically DNA, should couple efficiently to the solid support material. Further, the immobilized DNA should be both stable upon immobilization and accessible for base hybridization and other potential derivatization reactions. The immobilization attachment site should remain stable under the conditions employed for selectively cleaving the cleavable site in the modified oligonucleotide composition of the invention.

Coupling of an oligonucleotide to solid support may be carried out through a variety of immobilization attachment functional groups. Immobilization attachment sites for use in the present invention include those illustrated in FIGS. 2A–2M. Attachment of the support material to the oligonucleotide may occur by reaction between the reactive site on the support and a reactive site contained within the oligonucleotide or via an intervening linker or spacer molecule.

Figure 2A:
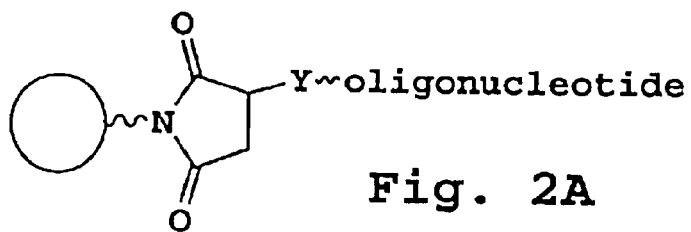
Figure 2B:
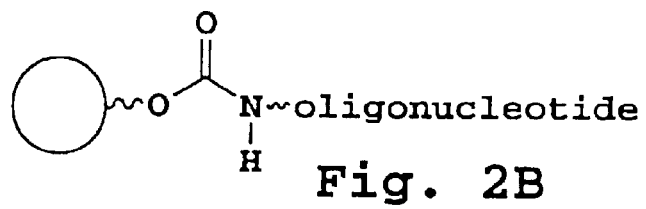
Figure 2C:
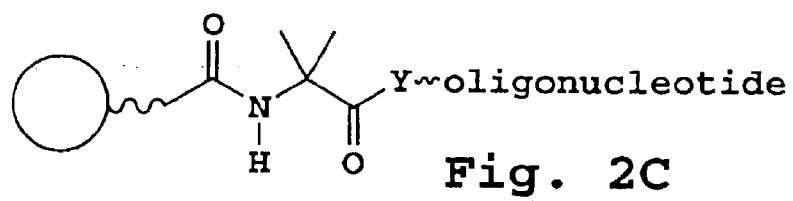
Figure 2D:
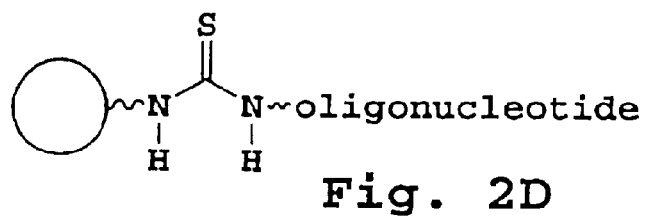
Figure 2E:
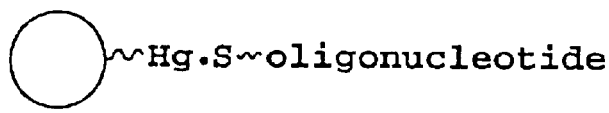
Figure 2F:
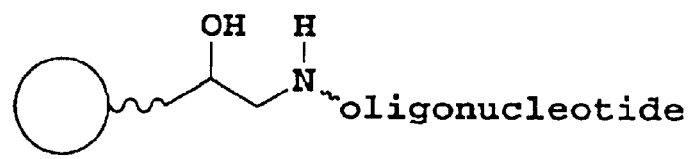
Figure 2G:
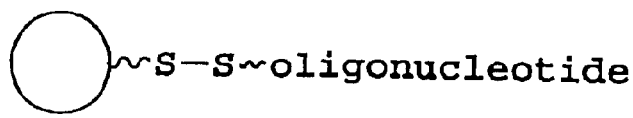
Figure 2H:
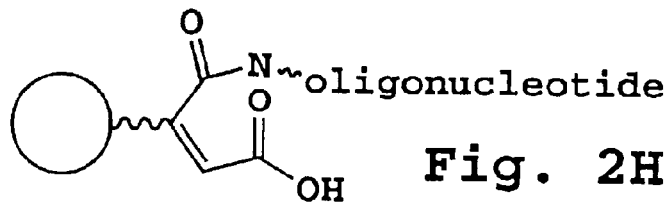
Figure 2I:
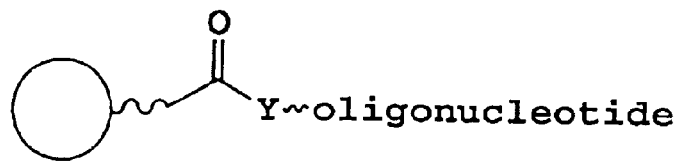
Figure 2J:
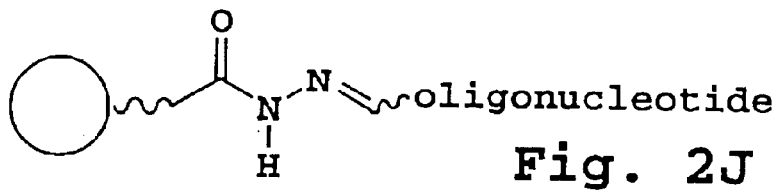
Figure 2K:

Although any suitable functional group fulfilling the desired criteria above may be used to attach the oligonucleotide to the support, preferred linkages include disulfide (FIG. 2G), carbamate (FIG. 2B), hydrazone (FIG. 2J), ester (FIG. 2C, FIG. 2I and FIG. 2K, where Y equals oxygen), (N)-functionalized thiourea (FIG. 2D), functionalized maleimide (FIG. 2A, where Y equals sulfur, oxygen, or nitrogen), streptavidin or avidin/biotin (FIG. 2L), mercuric-sulfide (FIG. 2E), gold-sulfide (FIG. 2M), amide (FIG. 2C, FIG. 2L and FIG. 2K, where Y equals nitrogen), thiolester (FIG. 2C, FIG. 2L and FIG. 2K, where Y equals sulfur). Other suitable functionalities for attaching to a solid support material include azo, ether, and amino.

The immobilization attachment site may be located (i) as a substituent along the modified primer backbone (e.g., derivatization occurring at a terminal 5'-hydroxyl position), (ii) as a substituent on one of the bases or sugars of the modified primer, (iii) in the first region of the primer, composed of a series of bases complementary to a solid phase bound intermediary oligonucleotide, (iv) within a nucleic acid extension segment resulting from an enzymatic extension reaction, or (v) contained within a target nucleic acid.

Immobilization via a base pairing interaction between the primer and a solid phase bound intermediary oligonucleotide (SPBIO) is shown in FIG. 8 and FIG. 9. Indirect immobilization of the primer extension product via a base pairing interaction solid phase bound template is shown in FIG. 10.

Solid support materials for use in coupling to an oligonucleotide include functionalized supports such as the 1,1'-carbonyldiimidazole activated supports available from Pierce (Rockford, Ill.) or functionalized supports such as those commercially available from Chiron Corp. (Emeryville, Calif.). Solid supports for use in the present invention include matrix materials such as 6% cross-linked agarose, Trisacryl GF-2000 (a hydrophilic matrix material) and TSK HW-65F, all activated with 1,1'-carbonyldiimidazole (Pierce). Immobilization is typically carried out by reacting a free amino group of an amino-modified oligonucleotide with the reactive imidazole carbamate of the solid support. Displacement of the imidazole group results in formation of a stable N-alkyl carbamate linkage between oligonucleotide and the support as shown in FIG. 2B. Coupling is usually carried out at pHs ranging from 9–11 although a pH range from 9.5–10 is preferable. Coupling to pH sensitive materials may be carried out in buffer at pHs around 8.5.

Amino-modified oligonucleotides for use in attaching to a solid support may be synthesized using standard solid phase DNA synthesis methodologies employing, for example,. the modified nucleoside phosphoramidite Amino-Modifier-dT (Glen Research, Sterling, Va.), which contains a base labile trifluoroacetyl group protecting a primary amine attached to thymine via a 10-atom spacer arm, phosphoramidite 5'-Amino-Modifier C6 (Glen Research, Sterling, Va.), which contains a primary amino group protected with an acid labile monomethoxytrityl group, or N-trifluoroacetyl-6-aminohexyl-2-cyanoethylN',N'-isopropylphosphoramidite (Applied Biosystems, Foster City, Calif.). Although amino-containing oligonucleotides are most commonly prepared using phosphoramidite chemistry, any other method which leads to oligonucleotides containing primary amine groups may also be used.

Amino-modified oligonucleotides are readily transformed to the corresponding thiol or carboxyl-terminated derivatives for use in immobilization or spacer arm attachment reactions requiring 5'-functionalities other than amino. Amino-modified oligonucleotides may be converted to the corresponding carboxyl derivatives by reaction with succinic anhydride (Bischoff et al., 1987). If desired, the carboxyl-derivatized primer may be coupled to a bifunctional linker such as 1,6-diaminohexane prior to attachment to the solid support by carrying out the coupling reaction in the presence of an activating agent such as a water soluble carbodiimide.

Thiol-modified oligonucleotides may be prepared by treating the deprotected 5'-amino group of a functionalized oligonucleotide with dithiobis(succinimidylpriopionate), followed by sulfhydryl deprotection with dithioerythritol (Bischoff et al., 1987).

Oligonucleotides containing free amino, thiol, and hydroxyl functions may also be coupled to supports by utilizing epoxide ring-opening reactions (Maskos et al., 1992). One such exemplary epoxy-activated solid support is available from Pierce (Rockford, Ill.) and contains 1,4-butanediol diglycidyl ether-activated agarose. Coupling reactions are typically carried out at pHs from 7.5–13, depending upon the stability of the molecule to be immobilized. In immobilization reactions carried out with the above Pierce support, the resulting immobilized oligonucleotide is separated from the solid support by a 13-atom hydrophilic spacer arm.

In another immobilization approach, aldehyde groups of a modified oligonucleotide are coupled to hydrazide groups on a solid matrix as shown in FIG. 2J. A primary hydroxyl group on an oligonucleotide is first oxidized to the corresponding aldehyde, typically with a mild oxidant such as sodium periodate. The oligonucleotide is then coupled to a hydrazide-containing matrix such as Pierce's CarboLink™ Hydrazide. The coupling reaction is performed at neutral pH.

Figure 2M:
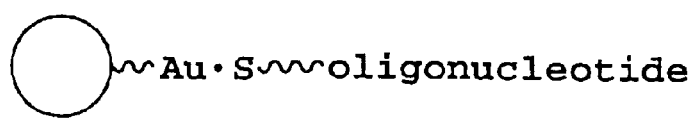

Alternatively, the immobilization reaction is carried out using a thiol-derivatized oligonucleotide which is coupled to a functionalized matrix such as Pierce's Immobilized p-Chloromercuribenzoate (FIG. 2E). The support is a cross-linked agarose containing an ethylene diamine spacer and coupling takes place via affinity binding between the mercury and sulfur atoms. Similarly, as shown in FIG. 2M, immobilization may be carried out by anchoring a 5'-thiolated primer to a gold surface (Hegner et al., 1993a). Using this approach, the modified primer is chemisorbed onto a gold surface e.g., the solid support) via thiolate bonding. The preparation of polycrystalline gold surface has been previously described (Hegner et al., 1993b).

Functionalization may also be carried out using a homo- or hetero-bifunctional cross-linker, such as Pierce's Sulfo- SMCC. Cross-linkers for use in the present invention will typically contain spacer arms between about 3–20 angstroms in length. Cross-linkers for use in coupling an oligonucleotide to a solid support will typically contain functional groups for targeting reactive primary amines, sulfhydryls, carbonyls, and carboxyls. Cross-linking agents for reaction with primary amino groups will typically contain terminal amidoester groups or N-hydroxysuccinimidyl esters. An exemplary linker such as Pierce's Sulfo-SMCC contains a reactive carboxyl group at one end for coupling to amine-derivatized solid supports such as hexylamine-derivatized polystyrene beads. The other end of the linker molecule contains a reactive maleimide molecule which readily reacts with oligonucleotides containing nucleophilic groups such as hydroxy, thio, or amino. Cross-linkers for reaction with sulfhydryl groups typically contain terminal maleimide groups, alkyl or aryl halides, α-haloacyls or pyridyl disulfides. A variety of chemical cross-linking agents are available from Pierce (Rockford, Ill.).

Alternatively, coated plates, such as those available from Pierce, may be used to immobilize the modified oligonucleotide. Examples of plates for use in immobilizing the oligonucleotides of the invention include activated plates such as Pierce's Reacti-Bind™ Maleic Anhydride Activated Polystyrene Plates and Reacti-Bind™ Streptavidin Coated Polystyrene Plates. A primary amino-containing oligonucleotide is immobilized on the former plate surface by covalent attachment through a stable amide bond formed by reaction between the free amino group of the oligonucleotide and the reactive anhydride (FIG. 2H). The latter plates are effective for affinity binding of biotinylated oligonucleotides. Gold-coated plates may also be utilized for binding to thiol-derivatized primers.

Biotinylated oligonucleotides for use in immobilization to streptavidin or avidin-coated solid supports are prepared as described in Example 2A and shown in FIG. 2L. A variety of biotinylation reagents are commercially available (e.g., Pierce) which are functiionalized to react with molecules such as modified oligonucleotides containing primary amino, sulfhydryl, or carbohydrate groups.

Returning to Example 2A, an amino-modified primer is treated with biotin or with a modified form of biotin containing an intervening spacer arm, such as NHS-SS-Biotin (Pierce), or NHS-LC-Biotin (Pierce), a biotin derivative containing an eleven carbon spacer arm between biotin and a terminal N-hydroxylsuccinimide activated carboxyl group. The biotinylated primer is then immobilized by attachment to a streptavidin-coated support. Due to the strong non-covalent biotin/streptavidin interaction, the immobilized primer is considered to be essentially irreversibly bound to the solid support. This is one preferred immobilization attachment for use in the present invention, as the resulting immobilized complex is unaffected by most extremes of pH, organic solvents, and other denaturing agents (Green, 1975). An alternative to avidin(streptavidin)-biotin immobilization is incorporation of a digoxigenin molecule (Sigma, St. Louis, Mo.) in the modified primer with subsequent capture using anti-digoxigenin antibodies.

Enzymatic methods may also be utilized for coupling an oligonucleotide to a solid support (Goldkorn et al., 1986). In one exemplary embodiment, a poly(da) tail is added to the 3' ends of a double stranded DNA using 3' terminal transferase. The (dA)-tailed DNA is then hybridized to oligo(dT)-cellulose. To covalently link the DNA to the solid support, the hybridized sample is first reacted with a Klenow fragment of DNA polymerase I, followed by treatment with T4 DNA ligase. The unligated strand of DNA is separated from the immobilized strand by heating followed by extensive washing. The method results in ssDNA covalently linked by its 5' end to a solid support.

The modified primers of the present invention may also be affixed onto a gold surface. In utilizing this immobilization approach, oligonucleotides modified at the 5'-end with a linker arm terminating in a thiol group are chemisorbed with high affinity onto gold surfaces (Hegner et al., 1993a). Thiolated primers, available through post solid-phase synthesis modification using commercially available reagents (Pierce, Rockford Ill.), are immobilized on a thin layer of gold either prior to or following enzymatic extension. The gold layer is deposited onto the sample stage for direct analysis by mass spectrometry following internal cleavage and evaporation. Alternatively, the resulting extension segments may be transferred onto an alternate surface prior to analysis.

4.3 Reactions Employing the Immobilized Cleavable Oligonucleotide Composition 4.3.1 Hybridization and Extension The methods employed for determining the sequence of a target oligonucleotide strand will often involve Sanger-type sequencing using the modified cleavable primers of the present invention. Immobilization of the modified primer on the solid support may take place either before or after the enzymatic extension reactions.

Utilizing the Sanger DNA sequencing procedure, dideoxynucleosides of each of the four bases are obtained for inclusion into the reaction mixture. The dideoxy nucleotides are incorporated into DNA by, for example, E. coli DNA polymerase since they have a normal 5' triphosphate group. Once incorporated into the growing DNA strand, the dideoxynucleoside triphosphate (ddNTP) cannot form a phosphodiester bond with the next incoming dNTP and growth of the DNA chain is terminated.

A typical DNA sequencing reaction using the Sanger method proceeds as follows. The reaction consists of a target DNA strand be sequenced, a modified primer containing a cleavable site in accordance with the invention, and that is complementary to the end of the target strand, a carefully controlled ratio of one particular dideoxynucleoside with its normal deoxynucleotide counterpart, and the three other deoxynucleoside triphosphates. The modified primer may or may not be immobilized to solid support at this point. (immobilization may occur either before or after the enzymatic extension reactions, depending on a number of experimental factors).

DNA polymerase is added and normal polymerization begins from the primer. Upon incorporation of a ddNTP, the growth of the chain is stopped. A series of different strands results, the lengths of which are dependent on the location of a particular base relative to the end of the DNA. The target strand is usually distributed into four DNA polymerase reactions, each containing one of the four ddNTPs and a modified primer of the present invention. The extension reaction is then carried out as described above. Sanger-type DNA sequencing is generally carried out using a DNA sequencing kit such as "SEQUENASE" Version 1.0 or Version 2.0 T7 DNA Polymerase (United States Biochemical, Cleveland, Ohio). The "SEQUENASE" Version 1.0 kit uses a chemically-modified DNA polymerase derived from bacteriophage T7 DNA polymerase in which the high 3'-5' exonuclease activity of the native T7 DNA polymerase is inactivated.

In using the USB "SEQUENASE" kit, double stranded templates are first denatured (if one is using double stranded template), and the primer is then hybridized or annealed to the target by heating for 2 min at 65° C., followed by low cooling to less than 35° C. over about 15–30 min. Supercoiled plasmid DNAs are denatured by treatment with sodium hydroxide, neutralized, and ethanol-precipitated in order to anneal the primer for sequencing.

Termination mixtures containing the different ddNTPs are prepared for use in the termination reactions. The annealed DNA mixture is optionally labeled, and the labeled reaction mixture is added to each of the four termination tubes. In the present invention, extension reactions are carried out to produce a distribution of products ranging from near zero to several hundreds of base pairs in length. Optionally, a stop solution (containing formamide, EDTA, bromophenol blue, and xylene cyanol FF) is added to stop the reactions prior to analysis of the resultant samples.

For reactions in which the modified primers were not immobilized to a solid support prior to enzymatic extension, immobilization is carried out as described in Section 4.2.2 above.

The immobilized extended primers are then washed to remove excess enzymes, ions, salts, and other impurities. In one embodiment, the extended primers are immobilized onto the surface of microtitre wells. Immobilization to the solid support facilitates product purification and subsequent isolation by cleavage of the timer at the cleavage site followed by removal in the supernatant.

Alternatively, DNA sequencing may be carried out using deoxynucleotide α-thiotriphosphates, dNTPαSs (available from United States Biochemical, Cleveland, Ohio), followed by limited exonuclease-promoted base-specific digestion, such as with Exonuclease III (New England BioLabs, Beverly, Mass.) or snake venom phosphodiesterase (Boehringer Mannheim, Mannheim, Germany)(Olsen et al., 1993). Cleavage of DNA fragments specifically at positions of incorporated phosphorothioate groups may also be carried out using chemical reagents such as 2-iodoethanol or 2,3-epoxy-1-propanol (Nakamaye et al., 1988).

Briefly, the sequencing of a target DNA sequence using the modified primers of the present invention via the incorporation of phosphorothioate nucleosides is carried out as follows. A target DNA sequence is hybridized with modified primer as described above. The primer is then extended enzymatically in the presence of one deoxynucleotide α-thiotriphosphate (dNTPαS) to generate a mixture of prime extension products containing phosphorothioate linkages. The primer extension products are then treated with a reagent that (i)cleaves specifically at the phosphorothioate linkages such as 2-iodoethanol or 2,3-epoxy-l-propanol, or (ii) digests the DNA downstream from the phosphorothioate linkage, such as a 3'-5' exonuclease, under conditions resulting in the production of a nested set of base-specific primer extension degradation products.

Optionally, the primer extension degradation products are immobilized at the immobilization attachment sites to produce immobilized primer extension degradation products, each containing a primer and an extension segment. Alternatively, immobilization may be carried out (i) prior to enzymatic extension, (ii) after enzymatic extension, or (iii) prior to treating the phosphorothioate-containing primer extension products with a phosphorothioate-specific cleaving reagent.

Subsequent to immobilization, the primer extension degradation products are washed to remove non-immobilized species. Cleavage at the cleavable site results in the release of extension segments, which are then sized by mass spectrometry. Using the sequencing method of this aspect of the invention, the read length of any given extension segment is increased relative to the read length of its corresponding primer extension degradation product.

The steps of hybridization, enzymatic extension, treatment with a phosphorothioate-cleaving reagent, immobilization, washing, cleaving, and sizing are then repeated with a second, third, an fourth of the four different dNTPαS analogs to determine the sequence of the target DNA by comparison of the sizes of the extension segments obtained from each of the four extension reactions.

The methods and modified primers described herein may also be used for obtaining a fingerprint of a target oligonucleotide. As described herein, fingerprinting refers to a method of determining the positions of no more than two different bases in a target oligonucleotide strand, as opposed to sequencing, which refers to a determination of the complete nucleotide sequence of (and also, in the case of a gene exon, the corresponding amino acid sequence encoded by) a target nucleic acid, including the identity and position of each nucleotide present in the target strand or its complement. DNA or RNA fingerprinting, which requires less reagents, can provide a rapid and cost effective alternative to sequencing, and may be used in a number of different applications, e.g., identification of one or more infectious agents in a genomic sample from a subject, screening cDNA libraries, screening genes from human or non-human genomes to detect mutations and polymorphisms and for forensic applications. One preferred method for determining a single 2-base fingerprint of an oligonucleotide extension segment, generated using the modified primers of the present invention, is mass spectrometry.

In determining a fingerprint of a target oligonucleotide, a base-specific nested fragment set, containing base-specific terminated fragments derived from the target molecule, is produced for subsequent analysis. As referred to herein, a nested set is defined as a mixture of biopolymers (e.g., DNA, RNA, peptides, or carbohydrates) for which all of the components of the mixture have a common terminus and are produced from a single polymeric sequence. The base-specific nested fragment set may be produced, for example, by base-specific chain termination using the Sanger method or by selective chemical cleavage, to be described below. In instances where amplification of a target molecule is desired, amplification is carried out using any of a number of conventional amplification methods including PCR™, SPA (single primer amplification, NASBA (nucleic acid sequence-based amplification), TMA (transcription-mediated amplification), and SDA (strand-displacement amplification).

In fingerprinting methods employing a size fractionating device for product analysis, such as a mass spectrometer, the resulting single-base fingerprint can often provide indirect information regarding the other bases present in the target sequence. For example, the difference in mass (Δm) corresponding to the positions of two peaks in a mass spectrum may also reveal the composition of the intervening bases, to be described as follows.

To determine a single base fingerprint of a target oligonucleotide, such as a thymidine fingerprint, a thymidine-specific nested fragment set is produced as described above. The resulting fragment family, containing a number of thymidine-terminated nucleotide fragments, is typically purified and analyzed by a size fractionation method, such as mass spectrometry. To increase mass spectrometric performance, mass-modified nucleotides can be utilized. The resulting mass spectrum contains a number of peaks, each corresponding to the mass of a particular thymidine-terminated fragment present in the product mixture. The differences in mass between the various thymidine-terminated fragments is then correlated with the calculated mass of various combinations of nucleotides, preferably with the assistance of a computer program containing the molecular weights of the modified primer, the portion of the primer 3' of the cleavable site, and each of the various nucleotides, to identify the combination of nucleotides intervening between the known thymidine positions.

As an illustration, in considering the difference in mass between two given fragment peaks, an exemplary mass difference of 1,276 mass units corresponds uniquely to the following base composition: (two G)+A+T. A single base fingerprint can thus be used to (i) identify the locations of a particular base within a target sequence and (ii) determine the base composition within localized regions of a target sequence.

For applications requiring a greater level of detail, a second base-specific nested set is produced and analyzed to produce a second fingerprint as described above. Different base-specific nested sets can be produced in single reaction vessel, or in separate reactions, depending upon the method utilized and the corresponding reagents required. The different base-specific nested sets (e.g.,thymidine-terminate fragments and cytidine-terminated fragments) may be analyzed separately, or as a mixture.

Use of a single base fingerprint for detection of a point mutation is illustrated in Example 7. Briefly, the cytosine fingerprints of two distinct single stranded DNA targets (SEQ ID NO:14 and SEQ ID NO:15) having sequences differing only at positions 16 and 19, relative to the 3' end (counting upstream after the priming region), were determined using dideoxycytosine triphosphate to produce a family of cytosine-terminated nucleotide fragments, followed by analysis of the resulting reaction product mixtures by mass spectrometry (FIG. 14A and FIG. 14B). The exact mass values corresponding to the differences between select peaks in each of the spectra were calculated, confirming the presence of two single nucleotide substitutions (point mutations) at positions 16 and 19.

In an alternative approach, a base-specific nested fragment set is produced by selectively cleaving a DNA or RNA molecule modified to contain selectively cleavable groups (e.g., dUTP or amino functionalized nucleoside triphosphates) at positions corresponding to a particular base. The resulting uridine-modified oligonucleotide is then treated with uracil DNA glycosylase to form a set of fragments, preferably a nested set captured onto a solid phase. Similarly, a 5'-amino-modified target molecule is cleaved by treatment with acid.

Preferably, the above fingerprinting method employs the cleavable primers of the invention to remove the majority of the primer from the primer extension fragments. By reducing the mass of the analyte fragments, the distribution of products is shifted into the region where mass spectrometry has higher mass accuracy and resolution. Additionally, it may be useful to mass modify the different nucleotides by introducing any of a number of mass modifying functionalities (e.g., by replacing thymidine with 5'-bromouridine, or utilizing an immobilization attachment site, spacer arm, or alternative internucleotide linkage, as described above) to enhance the mass difference between the different nucleotides.

In a second fingerprinting approach, a restriction endonuclease is used to generate a non-random fragmentation pattern, useful, for example, for detecting mutations.

In an alternate embodiment of the invention, target DNA for sequencing or fingerprinting is amplified using the polymerase chain reaction or PCR™ (Mullis 1987; Mullis et al., 1987; Kusukawa et.al., 1990; Gyllensten, 1989). Briefly, PCR™ amplification is typically carried out by thermal cycling a cocktail containing the target DNA of interest, a mixture of deoxynucleotide triphosphates (dNTPs), a reaction buffer, each of two primers, and an extension enzyme such as Taq DNA polymerase (United States Biochemical, Cleveland, Ohio) (Erlich, 1989; Innis, 1990). A PCR™ run profile typically consists of a 5-min denaturation step at 94° C., followed by 30 cycles of 15 sec at 94° C., 15 sec at the annealing temperature, and 1 min at 72° C. Following thermal cycling, the samples can be maintained at 4° C. until removal from the thermal cycler. Annealing temperatures range from out 55° C. to 65° C., although most target sequences amplify well at 60° C.

Amplification is followed by hybridization with the modified primers of the present invention, enzymatic extension and sequencing of the products as described above.

FIG. 12 illustrates PCR™ amplification of a template molecule using the modified primers of the present invention.

As an alternative to using dideoxy chain terminators, PCR™ can be combined with dUTP incorporation to produce a nested set terminated at the sites of dUTP incorporation by treatment with uracil DNA-glycosylase. PCR™ can also be combined with phosphorothioate methods, as described above.

In accordance with the present invention, amplification can be carried out using first and second primers, where one of the primers, i.e. the first primer 95, contains a cleavable site 99, and another primer, i.e. the second primer 105, contains an immobilization attachment site for binding to a solid support. The second primer is composed of a 5' end and a 3' end, is homologous to the target nucleic acid, and includes a first segment containing the 3' end of the second primer, and a second segment containing the 5' end of the primer and an immobilization attachment site.

These first and second primers are combined with a target nucleic acid 103 to generate primer/nucleic acid complexes and are converted to double stranded fragments 109 in the presence of a polymerase and deoxynucleoside triphosphates, as indicated at 107. The sizing method can be carried out using a large excess of target nucleic acid to generate substantial amounts of primer extension product, or alternatively, may be coupled with various rounds of amplification. Upon achieving a desired amount of product 109, extension products containing the second primer are immobilized 117 by attachment the immobilization attachment site, either before or after cleavage at the cleavable site. The extension product is then cleaved 111 at the cleavable site to generate a mixture which includes double stranded product 115. Non-immobilized cleaved fragments are removed 119, preferably by washing, and the purified double stranded product 121 is denatured 123 to release the extension segment 125, which is sized by mass spectrometry, where the read length of the extension segment is increased relative to the read length of the primer/nucleic double stranded fragments.

As will be appreciated, the cleavable site of the first primer and the immobilization attachment site of the second primer include those the types described above.

In the exemplary embodiment illustrated in FIG. 12, the first primer 95 contains a restriction enzyme recognition site 97 in the first primer region 101, and a cleavable site 99 in the second primer region, and the second primer contains an immobilization attachment site for attachment to a solid support. Cleavage at the cleavable site is carried out by addition of a restriction endonuclease selective for the recognition site contained in the first primer region to provide (i) released fragments containing the first region of the first primer and (ii) a double stranded product, which is immobilized prior to denaturing for release of the desired extension segment. As illustrated in FIG. 12, restriction endonuclease-promoted cleavage results in the release of a double stranded product 115 and a short double stranded fragment 113 containing the first region of the primer.

4.3.2 Cleavage

Cleavage of the selectively cleavable site may be carried out as described in Section 4.2.1 and in Examples 1A–D and Example 3. Returning to this aspect of the invention, internucleoside silyl groups such as trialkylsilyl ether and dialkoxysilane are cleaved by treatment with fluoride ion. Base-cleavable sites for use in the present invention include β-cyano ether, 5'-deoxy-5'-aminocarbamate, 3'-deoxy-3'-aminocarbamate, urea, 2'-cyano-3',5'-phosphodiester, 2'-amino-3',5'-phosphodiester, ester and ribose. Thio-containing internucleotide bonds such as 3'-(S)-phosphorothioate and 5'-(S)-phosphorothioate are cleaved by treatment with silver nitrate or mercuric chloride. Acid cleavable sites for use in the present invention include 3'-(N)-phosphoramidate, 5'-(N)-phosphoramidate, dithioacetal, acetal and phosphonic bisamide. An α-aminoamide internucleoside bond is cleavable by treatment with isothiocyanate, and titanium is used to cleave a 2'-amino-3',5'-phosphodiester-O-ortho-benzyl internucleoside bond. Vicinal diol linkages are cleavable by treatment with periodate. Thermally cleavable groups include allylic sulfoxide and cyclohexene while photo-labile linkages include nitrobenzylether and thymidine dimer.

Cleavage conditions are utilized which leave the immobilization attachment site intact, so that a major portion of the primer remains affixed to the solid support. Preferably, cleavage of the cleavable site results in primer extension products containing five or fewer base pairs from the primer sequence. This maximizes the amount of sequence information provided upon subsequent analysis.

4.3.3 Analysis

Any of a number of size fractionating devices may be used to determine the sequence of a target oligonucleotide fragment. Size fractionation methods for use in the present invention include gel electrophoresis, such as polyacrylamide or agarose gel electrophoresis, capillary electrophoresis, mass spectrometry, and HPLC.

In methods employing gel electrophoresis sizing and analysis, the DNA fragments are typically labeled with either radioisotopes or with attached fluorophores, and visualized using autoradiography or fluorescence detection, respectively.

The modified primers of the present invention are particularly advantageous when they are used to generate oligonucleotide fragments whose sizes are to be resolved using technologies that currently have difficulty resolving fragments of over about 100 base pairs differing by one nucleotide in length, such as mass spectrometry.

One preferred method for oligonucleotide analysis using the modified oligonucleotide composition of the invention is mass spectrometry, and particularly matrix-assisted laser desorption ionization (MALDI) mass spectrometry, preferably carried out on a time-of-flight (TOF) mass spectrometer (Wu et al., 1993). MALDI mass spectrometry provides a rapid and efficient method for oligonucleotide sequencing.

MALDI-TOF mass spectrometry may be used to provide unfragmented mass spectra of mixed-base oligonucleotides containing more than 100 base pairs. Moreover, mass spectral resolution of sequences currently to at least about 40 base pairs in length may be attained.

In this method, pulsed ultraviolet laser light is used to desorb an oligonucleotide out of an absorbing solid matrix, which causes creation of free, unfragmented, charged oligomers. Mass analysis is done in a time-of-flight mass spectrometer. Singly charged molecular ions are typically the most abundant species and fragment ions are minimized.

In preparing the sample for analysis the analyte is mixed into a matrix of molecules which resonantly absorb at the laser wavelength. Solid matrix materials for this use include 3-hydroxypicolinic acid (Wu et al., 1993), α-cyano-4-hydroxycinnamic acid (Youngquist et al., 1994), nicotinic acid (Hillenkamp, 1988), and ice (Nelson et al., 1989), although a preferred material is 3-hydroxypicolinic acid.

Examples 4 and 5 include detailed descriptions of MALDI-TOF mass spectral analyses of modified oligonucleotide compositions according to the present invention. Example 8, in conjunction with FIG. 15A and FIG. 15B, illustrates the difference in fragment information obtained for cleaved primer extension segments according to the invention (FIG. 15B) versus non-cleaved full primer-extension segments (FIG. 15A).

Figures 3A, 3B:
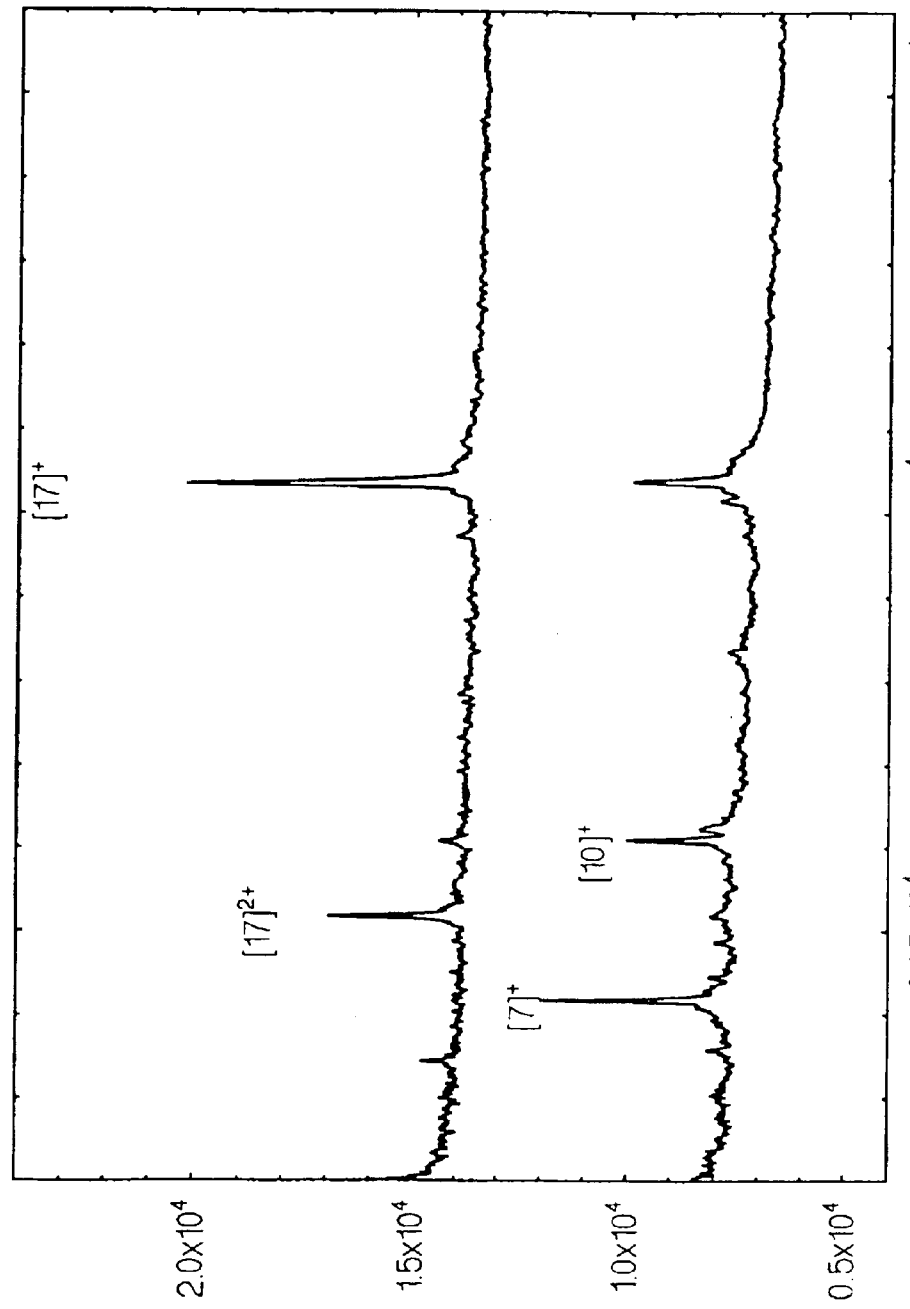
FIGS. 3A and 3B illustrate time-of-flight mass spectra for samples of a modified oligonucleotide primer containing a cleavable ribose desorbed from a solid matrix of 3-hydroxypicolinic acid both before (FIG. 3A) and after (FIG. 3B) selective cleavage.

As described in Example 3, a synthetic 17-mer DNA probe containing a cleavable ribose in the 7-position was selectively cleaved by ammonium hydroxide treatment. Mass spectra of the intact mixed base primer prior to (FIG. 3A) and after (FIG. 3B) ammonium hydroxide treatment reveal the selective cleavage of the ribose linkage. As shown in FIG. 3A, two sizable peaks were observed for the intact 17-mer corresponding to the di-protonated molecular ion $[M+2H]^{2+}$ and the protonated molecular ion $[M+H]^{+}$. Following ammonium hydroxide treatment, peaks corresponding to the expected cleavage products, the 7-mer, the 10-mer, and intact 17-mer, were readily observable and identifiable, as illustrated in FIG. 3B.

Figure 4:
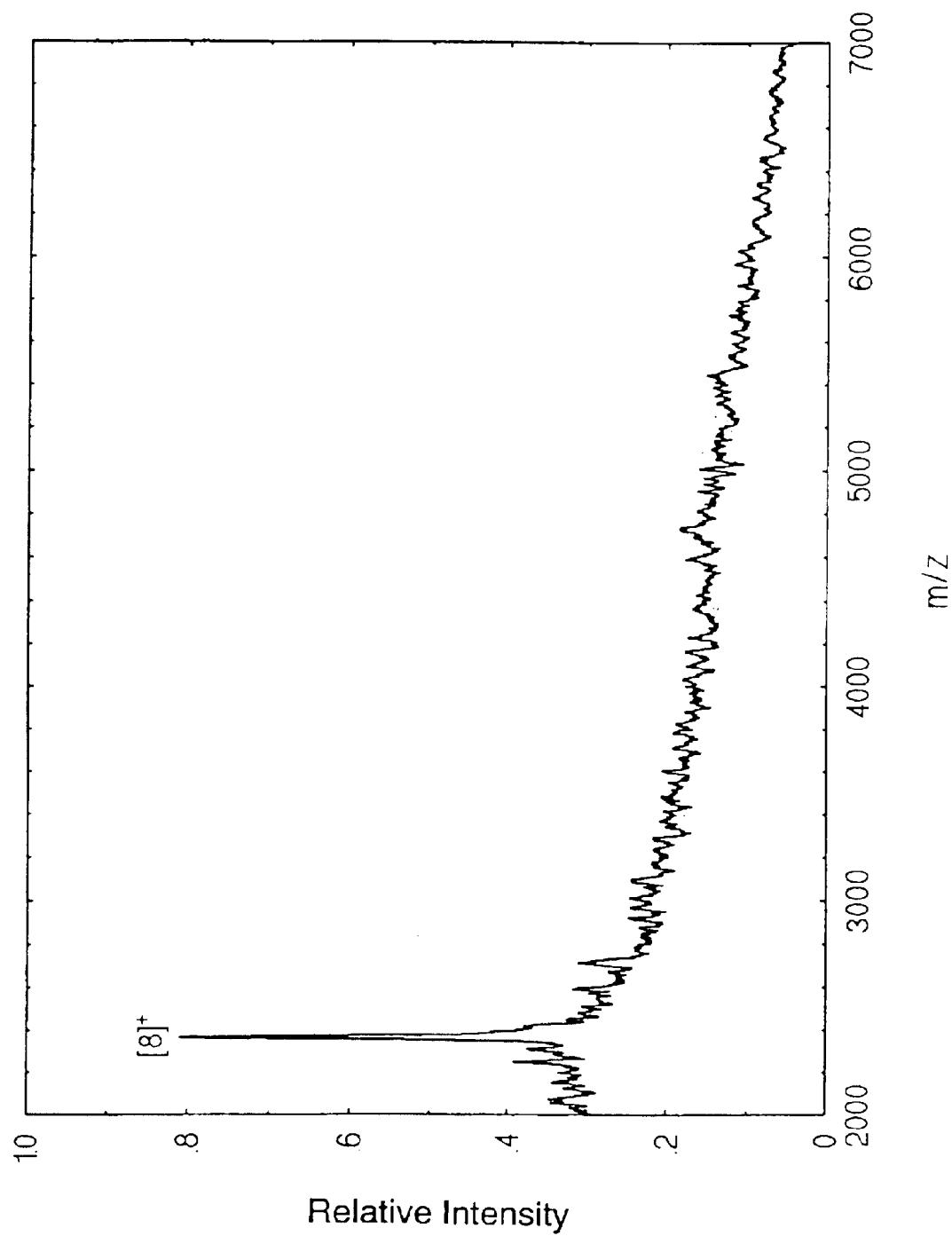
FIG. 4 is a time-of-flight mass spectrum of the cleavage product of an immobilized 18-mer containing a cleavable ribose at the 10-position.

Similarly, mass spectral analysis was carried out on a biotinylated 18-mer containing a ribose in the 10 position and captured on streptavidin-coated beads, as described in Example 5. The immobilized primer was washed after surface binding, followed by treatment with ammonium hydroxide to effect selective cleavage of the immobilized primer at the ribose site. FIG. 4 illustrates the mass spectrum of the 8-mer resulting from selective cleavage of the ribose site within the immobilized primer.

4.4 Utility

4.4.1 Genomic Sequencing

The method of the present invention may be used for both "shotgun-type" sequence analysis and "directed walk". In the shotgun approach, a random sequence of DNA is selected and used to prime on an unknown target. This approach uses large numbers of primers to increase the possibility of successfully hybridizing with an unknown target sequence. In one embodiment of this approach, a multi-well assay format is used where each well has a different primer and the same substrate (i.e. the target DNA molecule) is added to each well under hybridization conditions. The primers in the wells are the modified primers of the present invention where immobilization to the well surface is through the primer immobilization site. Primer extension reactions are carried out. Extension products are only formed in wells where complementary sequences exist between the primer and the substrate. Each well is examined for the presence of extension products. Extension products are then sequenced and sequences assembled for any given target DNA molecule based on the known sequences of the primers that yielded extension products and base sequence overlap from the extension product sequences (i.e. alignment of the extension product sequences). In using the modified primers of the present invention, the amount of sequence information for the extension segments is maximized over that obtained with similar techniques employing conventional primers, due to cleavage and removal of a large portion of the primer prior to fragment analysis (e.g., increased read lengths). Further, the method, when coupled with analysis by mass spectrometry, is fast and can provide large amounts of data in a relatively short period of time.

In a related approach, the present method may be used to sequence or fingerprint short reads of cDNA inserts for purposes of gene mapping and identification. These short reads identify each insert uniquely and are called Expressed Sequence Tags (ESTs) or Expressed Fingerprint Tags (EFTs). In preparing a cDNA library, cDNA copies of mRNAs are first inserted into a standard cloning vector such as pBlueScript. A modified primer according to the present invention is designed to hybridize to the pBlueScript vector sequence with its 3' end immediately adjacent to the cDNA insert. Primer extension and sequencing or fingerprinting reactions are then carried out which read into the insert and identify its sequence or fingerprint. In order to identify a unique length of sequence, a minimum read length for the extension segment is typically 30 bases, although a preferred read length is at least about 40 bases.

In an alternative embodiment, an array of the immobilized, cleavable primers can be formulated (Fodor et al., 1991; Southern et al., 1992). In this aspect of the invention, the array consists of the modified primers of the present invention where the cleavable linkage is, for example, a photocleavable linkage (e.g., backbone nitrobenzyl group) and the primer is attached to the support matrix through the immobilization site of the modified primer. In this embodiment, the target DNA molecule is hybridized to the primers, primer extension reactions are carried out and the different sequence primers are sequentially cleaved and the presence or absence of an extension product is determined. When extension products are detected their sequences can be determined as described above.

In the directed walk approach, a known DNA sequence is used as the primer sequence, thus providing an initiation point for sequencing in both directions away from the known region. Each newly identified sequence is then used to direct the synthesis of new primers to enable progression of the sequence walk.

4.4.2 Diagnostics

A number of synthetic oligonucleotides are available or may be readily synthesized which are complementary to target nucleic acid sequences (e g., RNA or DNA) and may be used as probes to detect the presence of certain bacteria, viruses, fungi, parasites and the like.

The oligonucleotide compositions of the present invention may be used, for example, to detect the presence of specific DNA or RNA sequences or fingerprints corresponding to the following targets (i) herpes viruses such as cytomegalovirus (CMT), Epstein Barr, and Simplex Herpesvirus; (ii) hepatitis viruses such as hepatitis A, B, G, and D; (iii) papillomaviruses such as human papilloma virus 6, 11, 16, 18, and 33; (iv) retroviruses such as human immunodeficiency virus 1 (HIV I), HIV II, human T-cell lymphoblastic virus I (HTLV I), HTLV II; (v) animal viruses such as pig parvovirus and pig mycoplasma hypneumoniae, parvoviruses such as parvovirus B 19; (vi) picornavirus such as rhinovirus (enterovirus) and rhinovirus HRV 2–14; (vii) bacteria such as mycobacterium avium, mycobacterium tuberculosis, chlamydia trachomatis, *Escherichia coli*, streptococci and staphylococci; and (viii) parasites such as trypanosoma, toxoplasma, and plasmodia.

Modified primers of the present invention having a primer sequence, such as a sequence specifically hybridizable to a nucleic acid from the microorganism of interest, are hybridized to nucleic acids in a sample. Primer extension reactions and isolation of extension products is carried out as described above. Presence of the extension product indicates the presence of a nucleic acid from the microorganism in the sample. The modified primers and sizing method of the present invention provide a method for rapid, high throughput screening for the presence of specific, target sequences or fingerprints using mass spectrometry.

In a related embodiment, the modified primers of the invention can be used to identify pathogens by direct sequencing or fingerprinting. In one such approach, a particular region of genomic DNA is identified which has segments that are common among a large population of pathogens (e.g., conserved regions) located next to regions that contain unique sequences for each pathogen (e.g., variable regions). One such exemplary sequence is from DNA that is transcribed into bacterial 16 S ribosomal RNA, or 16 S rRNA (Olsen et al., 1992). All 16 S-like rRNAs contain the same core structure. Nucleotides which are conserved in 90% of the available bacterial 16 S rRNA sequence have been identified (Schmidt et al., 1994).

Pathogen identification using rRNA as described above is carried out as follows. In accordance with the present invention, a primer is constructed to hybridize to a select region of the 16 S rRNA consensus sequence, for example, sequence 1047–1065 in 16 S rRNA, where (i) the primer has the sequence 5'-ACGACANCCATGCANCACC-3' (SEQ ID NO:9) or 5'-ACGACATCCATGCATCACC-3' (SEQ ID NO:19), and (ii) reads into the hypervariable region, e.g., sequence 995–1046. Upon analysis of the primer extension segments by mass spectrometry, a single pathogen, if present, can be uniquely identified by determining the sequence or fingerprint along the hypervariable region, with a desirable read length of at least 20 bases, and preferably, at least 40.

Alternatively, instead of selecting a conserved region adjacent a hypervariable region, a series of unique primers can be created that will hybridize to a hypervariable or unique region of a selected pathogen. Enzymatic extension of these primers provides sequence or fingerprint information about an adjacent segment of hypervariable region. This methodology enables specific identification of each pathogen present in a mixed population. Utilizing this approach, one may target different hypervariable regions for each target pathogen. This approach may be preferred for identifying viruses for which there is often very little conservation among other viruses or bacteria.

In addition to determining the presence of a nucleic acid in a sample from such microorganisms, the present invention facilitates the determination of the specific sequences or fingerprints present in a sample. For example, specific variants of HIV or trypanosomes can be identified by fingerprinting or sequencing as well as the presence or absence of genes responsible for antibiotic resistance.

The modified primers can likewise be used in diagnostic methods where mutant sequences are distinguished from wild-type sequences by sequence variations, such as, deletions, insertions, point mutations. Numerous potential target sites can be evaluated by this method including target sites selected from DNA sequences that vary in length (e.g., BCR/ABL) as well as those that vary in sequence (e.g., sickle cell anemia). The sizing methodology of the present invention is particularly suited for the former application (e.g., target sites of varying length). Hybridizations of the modified primers to target nucleic acids are carried out according to standard procedures, with suitable adjustment of the hybridization conditions to allow modified primer hybridization to the target region.

Exemplary genetic disorders for detection using the modified primers of the present invention include sickle cell anemia and α1-antitrypsin deficiency (Watson et al., 1992). As shown in FIG. 7A, sickle cell anemia results from a mutation that changes a glutamic acid residue (coded by the triplet GAG) for a valine residue (coded by GTG) at position 6 in the β-globin chain of hemoglobin. This base change (A to T) destroys the recognition sequence for a umber of restriction enzymes, including MstII. A modified primer for detecting this disorder would typically contain a cleavable site as indicate in FIG. 7A, located about 2 nucleotides from the end of the primer and preferably about 10–20 nucleotides upstream from the known mutation site.

Also detectable using the modified primers of the present invention is α1-antitrypsin deficiency, a disorder characterized by uninhibited production of elastase, a protease which destroys the elastic fibers of the lung causing patients to suffer from pulmonary emphysema. The α1-antitrypsin gene has been cloned and as shown in FIG. 7B, the mutant gene, a fragment of which is presented by SEQ ID NO:7, corresponds to a single base change that leads to an amino acid substitution (glutamine to lysine) at residue 342 as indicated by SEQ ID NO:8. A portion of the wild-type α1-antitrypsin gene, as shown in FIG. 7B (top), is presented by SEQ ID NO:5. A fragment of the protein produced in individuals having the wild type α1-antitrypsin gene is presented by SEQ ID NO:6. Other diseases for which the corresponding gene mutations have been identified and which may be detected using the modified primers of the present invention include Duchenne muscular dystrophy, factor X deficiency, hemophilia and phenylketonuria. Modified primers used for detecting such disorders typically contain a cleavable site located near the end of the primer, where the end of the primer is upstream from the known mutation site (e.g., within about 20 base pairs from a mutation site detected in a 40-mer).

Detection of a point mutation using the methods described herein is provided in Example 7 and further illustrated in FIG. 14A and FIG. 14B.

Another diagnostic example is the detection of BCR-ABL transcripts, which are found in the majority of chronic myelogenous leukemia (CML) patients and in $Ph^+$ acute lymphocytic leukemia patients, and are believed to be necessary for the maintenance of leukemic phenotype (Szczylik et al., 1991; Gale et al., 1984; Collins et al., 1984; Daley et al., 1988). The BCR-ABL transcripts are the result of a translocation of the proto-oncogene ABL (chromosome 9) to the breakpoint cluster region (BCR) (chromosome 22), resulting in the formation of BCR-ABL hybrid genes. In this embodiment, the modified primers of the present invention would have their 3' end before the breakpoint region. Primer extension reactions would then proceed across the breakpoint region if present, or continue through the normal transcript region if no breakpoint was present. The sequence of such primer extension products are diagnostic of whether a breakpoint fusion exists in any given sample of nucleic acids.

The modified primers can also be employed in DNA amplification reactions (e.g., Mullis, 1987a; Mullis et al., 1987b) for detecting the presence of specific sequences in samples by sizing or sequencing or for preparing quantities of DNA for sequencing reactions. In this embodiment of the invention, modified primers containing immobilization sites that can be attached to the solid support following amplification are particularly useful (e.g., biotin and digoxigenin). Amplified products can be captured, the modified primers cleaved, and the resulting amplification products isolated.

In particular, the present method may be utilized to identify pathogens by the sizing of PCR™ products. Briefly, primers are first selected to hybridize with a sequence unique to the target pathogen(s) of interest. The primers are chosen for use in a multiplex situation (e.g., one in which several different pathogens may be present) to produce PCR™ products of varying sizes, with each size correlating to a unique PCR™ product for a specific pathogen.

Such a study for determining the presence of three different pathogens (e.g., *Pseudomonas aeruginosa*, *Escherichia coli*, and *Staphylococcus aureus*) is carried out by adding to a sample containing, in addition to a DNA analyte, modified primers for each of the above pathogens designed to produce PCR™ amplification products having sizes of, for example, 65, 70, and 75 base pairs, respectively.

The PCR™ products are reduced in size by as many as 20–25 nucleotides by cleavage at the cleavable site (in the modified primer). This results in shifting the corresponding peaks into a more readily resolvable range of the mass spectrometer and permits multiplexing of greater numbers of PCR™ products.

The cleaved-amplification products are detected and sized using mass spectrometry, according to the method of the present invention.

The following examples illustrate, but in no way are intended to limit the scope of the present invention.

Materials and Methods

Protected nucleotide H-phosphonates such as Bz-DMT-deoxyadenosine H-phosphonate, iBu-DMT-deoxyguanosine H-phosphonate, fully protected deoxynucleoside phosphoramidites, protected deoxynucleoside diesters and triesters, nucleotide dimers, and solid phase supports may be obtained from Sigma Chemical Co. (St. Louis, Mo.). Bis (trifluoromethanesulfonyl)diisopropylsilane may be obtained from Petrach System Inc. (Bertram, Pa.). Phosphoramidites may be obtained from Applied Biosystems (Foster City, Calif.). Standard chemical reagents and solvents may be obtained from Aldrich Chemical Company (St. Louis, Mo.).

EXAMPLE 1

Preparation of a Modified Oligonucleotide Containing a 3'-5'-Cleavable Linkage

Nucleoside dimers containing the following 3'-5'-internucleoside cleavable linkages are prepared as follows.

A. 3',5'-Dialkoxysilane Internucleoside Linkage

The 3'-O-functionalized nucleoside intermediate, 3'-O-(diisopropylsilyl)-2'-deoxynucleoside triflate (1) is prepared by first adding bis(trifluoromethanesulfonyl) diisopropylsilane (1 mmol) to an equimolar amount of the sterically hindered base, 2,6-di-tert-butyl-4-methylpyridine, dissolved in dry acetonitrile, under an inert atmosphere. The resulting solution is cooled to −40° C. in a cooling bath, to which is added a solution of a 5'-(O)-protected nucleoside, 5'-dimethoxytrityl)-2'-deoxynucleoside (0.9 mmol) and 2,6di-tert-butyl-4-methylpyridine (0.2 mmol). in dimethylformamide over a 10 min period. The resulting reaction mixture is stored at 40° C. for 1 h and then allowed to warm to room temperature. The 3'-O-diisopropylsilyl triflate product is isolated by precipitation from water, with yields typically ranging from 90–100%. Isolation is not required, and preferably, the reactive intermediate is coupled directly with unprotected nucleoside to form the desired dimer.

The above procedure is used to form the 3'-silyl derivatives of the protected nucleosides 5'-(O)-dimethoxytrityl-thymidine, N6-benzoyl-2'-deoxy-5'-(O)-DMT-adenosine, N4-benzoyl-2'-deoxy-5'-(O)-DMT-cytidine, and N2-isobutyl-2'-deoxy-5'-(O)-dimethoxytrityl-guanosine with minimal formation of the undesired 3',3' symmetrical dimers.

Intermediate (1) is reacted with nucleoside, such as thymidine, by stirring a mixture of (1). and nucleoside for approximately 1 h at room temperature. The coupled dimer is isolated by adding the reaction mixture dropwise to a vigorously-stirred ice/water mixture. The mixture is filtered to give a white solid, which is then dried and purified by column chromatography on silica gel (eluent: ethyl acetate/hexane gradient). The protected dimer, 5'-(O)-DMT-3'-(O)-(5'-(O)-nucleosidyldiisopropylsilyl)thymidine (2), is typically isolated in yields ranging from 50–5%

The prepared dimers are then functionalized for use in automated solid phase synthesis to form primers containing a dialkoxysilane cleavable site.

The dimer, such as (2) above, is converted to the corresponding 3'-(2-cyanoethyl-N,N-diisopropylphosphoramidite) by dissolving the 5'-DMT dimer in tetrahydrofuran and adding the resulting solution dropwise to a stirred solution containing 4-DMAP (4-dimethylaminopyridine), diisopropylethylamine and 2-cyanoethyl-N,N-diisopropylphosphoramidochloridite in THF under nitrogen and maintained at room temperature. The reaction mixture is stirred for 2 h, added to ethyl acetate, washed with brine, and dried over magnesium sulfate. The crude product is then purified by column chromatography on silica using 1:1 ethyl acetate/hexane as the eluent.

The phosphoramidite-functionalized primer then employed for use in automated solid phase synthesis using a programmable DNA synthesizer to form an oligonucleotide primer containing a 3'-5'-diisopropylsilyl ether cleavable site.

Cleavage: After carrying out the desired hybridization and extension reactions with an immobilized primer containing a dialkoxysilane internucleotide linkage as described above, the silyl-ether (Si—O) linkage is selectively cleaved by treatment with fluoride ion (Green, 1975) to release the extension product, typically containing no more than about five nucleotides derived from the modified primer molecule.

B. 3'(S)-Phosphorothioate Internucleoside Linkage

The functionalized nucleoside, 5'-(O)-monomethoxytrityl-3'-(S)-thiophosphoramidite, is prepared as follows. The 3'-S-functionalized starting material, 5'-(O)-monomethoxytrityl-3'-(S)-benzoyl-thymidine (3), is prepared according to the method of Cosstick et al. (1988). Debenzoylation is carried out by treating a solution of 5'-(O)-monomethoxytrityl-3'-(S)-benzoylthymidine dissolved in argon-saturated ethanol and maintained at 5° C. with 1ON sodium hydroxide. The resulting solution is stirred for approximately 1 h. The product, 5'-O-MMT-3'-thiothymidine (4), is purified by column chromatography on silica gel. The 5'-(O)-MMT-3'-(S)-thymidine (4) is then converted to the corresponding thiophosphoramidite by reaction with 2-cyanoethyl-N,N-diisopropylaminophosphomonochloridite under standard conditions (McBride et al., 1983). The 3'-(S)-phosphoramidite (5) is suitable for coupling to a second nucleoside to form a dimer containing a cleavable phosphorothioate site or for use in automated solid phase synthesis to prepare an oligonucleotide containing a phosphorothioate internucleoside linkage.

Chemical synthesis of the phosphorothioate dimer is carried out as follows. A solution of 3'-(O)acetylthymidine in acetonitrile is added dropwise over a 20 min period to a stirred solution of the 3'-(S)-phosphoramidite (5) in acetonitrile saturated with 5-(4-nitrophenyl)tetrazole. Use of the tetrazole activating agent reduces the probability of the self-condensation reaction occurring between two thiophosphoramidite molecules. The resulting thiophosphite dimer (6) is oxidized in situ by quenching the reaction mixture with 2,6-lutidine, followed by addition of an oxidant such as TBA periodate in dichloromethane. The fully protected phosphorothioate dimer (7) is deprotected by treatment with t-butylamine, 80% aqueous acetic acid, followed by concentrated aqueous ammonia to yield the 3-(S)-phosphorothioate-linked thymidine dimer (8).

Formation of an oligonucleotide probe containing a 3'-(S)-phosphorothioate cleavable linkage is performed by solid phase synthesis on controlled pore glass using a DNA synthesizer. The protocol and reaction conditions for conducting the solid phase reaction cycle are adjusted according to the primer products desired using standard solid phase phosphoramidite procedures. The functionalized 3'-(S)-phosphoramidite nucleoside (5), prepared as described above, is utilized to introduce the 3'-(S)-phosphorothioate moiety into the oligonucleotide primer in the presence of the functionalized tetrazole reagent, 5-(para-nitrophenyl) tetrazole.

Cleavage: After carrying out hybridization, extension, and washing of an immobilized modified primer containing a 3'-(S)-phosphorothioate internucleotide bond, selective cleavage of the phosphorus-sulfur bond is carried out by treatment with aqueous silver nitrate.

C. 5'(S)-Phosphorothioate Internucleoside Linkage

Synthesis of an oligonucleotide containing a 5'-phosphorothioate internucleoside linkage is carried out by first synthesizing a derivatized phosphoramidite, 5'-(S)-trityl-deoxythymidine-3'-(O)-(2-cyanoethyl-N,N-diisopropylamino)phosphite as described below.

5'-(O)-p-toluenesulfonyl thymidine (9) is prepared by reacting thymidine with one equivalent of p-toluenesulfonyl chloride in pyridine. The reaction mixture is stirred for 3 h at room temperature, cooled in ice and quenched by addition of water. Following dissolution in ethyl acetate, and sequential washing with sodium bicarbonate and brine, the solution is dried over sodium sulfate and the solvent is removed in vacuo. The desired 5'-tosylate product (9) is readily recrystallized from ethyl acetate/methanol, thus avoiding the need for a protecting group at the 3'-OH position.

The 5'-tosylate is then converted to the corresponding 5'-S)-trityl-deoxythymidine (10). A solution of the 5'-(O) tosylthymidine (9) in ethanol is added to a reaction flask containing a five-fold molar excess of 7.0 M sodium hydroxide and triphenylmethyl mercaptan in ethanol (which generates the corresponding reactive thiolate in situ). The reaction mixture is refluxed for 8 h under an inert atmosphere, filtered to remove residual solids, dissolved in ethyl acetate, and the solution is washed, dried, and evaporated in vacuo. The crude product is purified by chromatography on silica gel using a methanol/methylene chloride gradient.

The desired reactive nucleoside phosphoramidate, 5'-(S)-trityl-deoxythymidine-3'-(O)-(2-cyanoethyl-N,N-diisopropylamino)phosphite (11), is prepared by treating a solution of the protected nucleoside, 5'-(S)-trityl)- deoxythymidine (10), in dry 1:1 acetonitrile/methylene chloride with an equimolar amount of tetrazole, followed by addition of a 1.5 molar excess of 2-cyanoethyoxy-bis-(N,N-diisopropylamino)phosphine. The reaction mixture is stirred for about 1 h at room temperature and subsequently quenched by addition of butanol. The solution is diluted with ethyl acetate, washed, dried over anhydrous sodium sulfate, filtered, and evaporated to dryness. The crude product is purified by flash chromatography.

Incorporation of the desired 5'(S)-phosphorothioate cleavable site into an oligonucleotide probe is carried out by utilizing standard solid phase phosphoramidite chemistry.

D. 5'(N)-Phosphoramidate Internucleoside Linkage

Oligonucleotide fragments containing a 5'-(N) phosphoramidate internucleotide bond are prepared as follows.

Thymidine is transformed to the corresponding 5'-azide derivative (12) by treatment with sodium azide and triphenylphosphine in carbon tetrabromide according to the procedure of Hasa et al. (1976). Reduction of 5'-azido-deoxythymidine (12) is then carried out by hydrogenation over Pd/C catalyst to form the corresponding 5'-amino derivative (13).

Formation of the corresponding 5'-N-protected nucleoside is carried out by dissolving (13) (25 mmol) in anhydrous pyridine (150 ml), to which is added 4-DMAP (17 mmol), triethylamine (17 mmol), and 4-methoxytrityl chloride (60 mmol), and the resulting reaction mixture is stirred for 2 h at room temperature. Methanol is added to the reaction flask and the resulting mixture is added to a solution of saturated sodium bicarbonate, extracted with chloroform, and the organic extracts dried over anhydrous sodium sulfate. The organic layer is evaporated to dryness and the resulting crude residue is purified by column chromatography over silica gel to yield 5'-amino-5'-deoxy-5'-(N)-(4-methoxytrityl)thymidine (13). (Cleavage of the N-MeOTr protecting group is carried out by treatment with 3% dichloroacetic acid in 1,2-dichloroethane).

The desired functiionalized nucleoside, 5'-amino-5'-deoxy-5'-(N)-(4-methoxytrityl)thymidine-3'-(2-cyanoethyl-N,N-diisopropylphosphoramidite (14), containing a reactive phosphoramidite moiety suitable for incorporation into an oligonucleotide fragment is synthesized as follows.

The 5'-amino-protected thymidine (13) (4 mmol) is dissolved in anhydrous methylene chloride (60 ml), to which is added dry bis(diisopropylammonium)tetrazolide (3 mmol) and (2-cyanoethoxy)bis(diisopropylamino)phosphine, (8 mmol). The mixture is stirred for 1 h at room temperature, poured into a saturated sodium bicarbonate solution, and extracted several times with chloroform. The combined organic extracts are rinsed with brine, dried, and evaporated to dryness. The crude residue is dissolved in a minimal amount of methylene chloride and precipitated by addition of pentane to yield a mixture of the diastereomeric product, 14.

The functionalized nucleoside 14 is then selectively introduced into an oligonucleotide fragment to form an oligonucleotide containing a 5'-(N)-phosphoramidate cleavable site. The 5'-amino nitrogen of thymidine derivative 14 is the reactive center at which phosphoramidate bond formation takes place. The modified nucleoside 14 is introduced in the course of a standard cycle into a growing DNA fragment synthesized on a solid support as follows. Insertion of the phosphoramidate group is performed at a specific site to form the desired nucleotide fragment containing a selectively cleavable site.

Formation of the following modified exemplary sequence: d(T-T-C-A-T-G-C-A-A-(phosphoramidate)-T-C-C-G-A-T-G) (SEQ ID NO:1) is performed as follows. The DNA fragment is synthesized in a stepwise fashion beginning from the hexamer sequence d(C-C-G-A-T-G) (Gromova, 1987). The hexamer is synthesized on controlled pore glass as solid support using standard procedures (Bannwarth et al., 1986; Bannwarth, 1987). The introduction of key intermediate 14 is performed during a standard cycle utilizing slightly longer times for the coupling of 14 and for deblocking of the 4-methoxytrityl protecting group. Following cleavage of the 5'-MeOTr group of 14, the synthesis is continued using standard phosphoramidites as the building units to form the desired 16-mer sequence.

The support material is treated with concentrated ammonia at 56° C. overnight to cleave the 16-mer product from the solid support. Following removal of the support material, the ammonia is removed by vacuum evaporation, and the remaining residue is dissolved in water/dioxane and subsequently precipitated by addition of THF. The resulting 16-mer is then purified by either gel electrophoresis or HPLC.

Selective chemical cleavage of the phosphoramidate internucleotide bond is carried out under mild acidic conditions to form the corresponding phosphate and amino-functionalized fragments. Treatment with 80% acetic acid at room temperature for between 2–6 h results in selective cleavage of the internucleotide phosphoramidate bond while leaving the unmodified portion of the DNA fragment intact.

EXAMPLE 2

Attachment to the Solid Support

A. Streptavidin Affinity Immobilization

A modified primer from Example 1 above containing a cleavable site is immobilized by attachment to a functiionalized solid support material. In some cases the cleavable site-containing primer is modified as described below.

For attaching an oligonucleotide primer to a streptavidin-coated support a biotinylated primer is typically used. Biotinylation is carried out as follows.

A primer containing a cleavable site is prepared as in Example 1, with a minor modification: the primer is synthesized to contain a reactive amino site for biotinylation. An amino group is introduced during solid phase synthesis using a standard DNA synthesizer, such as Applied Biosystems 393 DNA/RNA Synthesizer.

To selectively introduce the internal amino function, the modified nucleoside phosphoramidite Amino-Modifier dT, containing a base labile trifluoroacetyl group protecting a primary amine attached to thymine with a 10 atom spacer arm, is added at an appropriate phase of the DNA synthesis cycle. Upon completion of the oligonucleotide synthesis, the primer is cleaved from the support by standard methods. The remaining base-protecting groups as well as the trifluoroacetyl amino protecting group are removed by treatment with fresh, concentrated ammonium hydroxide at 40° for 15–17 h. The solution is dried by rotary evaporation, and the residue is redissolved in 200 μl of water.

The amino-modified primer (approximately 0.25 μmol) is reacted with NHS-LC-Biotin (Pierce, Rockford, Ill.) which has an 11 carbon spacer between the biotin group and the N-hydroxylsuccinimide activated carboxyl group. Aliquots of a 50 MM NHS-LC-biotin solution in DMF are added to the primer solution containing 0.1 M sodium bicarbonate/sodium carbonate buffer at pH 9 over a 1 h period. The solution is maintained at room temperature overnight and the biotinylated primer is then purified by reverse phase HPLC.

The biotinylated primer is then immobilized by attachment to streptavidin-coupled magnetic beads (Dynabeads M-280, Dynal, Inc., Great Neck, N.Y.) as described in Dynabeads M-280 Technical Handbook: Magnetic DNA Technology 6, Dynal, Inc. A neodymium-iron-boron magnet is used to immobilize the beads during supernatant removal and washing steps.

B. Immobilization via a Thiourea Linkage

5'-Amino-modified oligonucleotide primers containing a cleavable linkage are prepared as described in Examples 1 and 2A above.

Glass slides are activated in a two-stage process for coupling to amino-functionalized oligonucleotides. The glass surface is first functionalized by reaction with aminopropyltrimethoxysilane to form an amino-derivatized surface. To carry out the amino-functionalization, clean microscope slides are immersed for 2 min in a 1% solution of 3-aminopropyltrimethoxysilane solution in 95% acetone/water. The slides are then washed several times with acetone (5 min per wash), and dried for 45 min at 110° C.

Following amino-derivatization, the glass slides are treated with excess p-phenylenediisothiocyanate to convert the amino groups to amino-reactive phenylisothiocyanate groups suitable for coupling to amino-functionalized oligonucleotides. The amino-derivatized glass plates are treated for 2 h with solution of 0.2% 1,4-phenylene diisothiocyanate solution in 10% pyridine/DMF, followed washing with methanol and acetone.

A 2 mM solution of the amino-modified primer in sodium carbonate/bicarbonate buffer (2 $\mu$L) is applied directly to the activated glass plate surface and the resulting slides are then incubated at 37° C. in a covered Petri dish containing a minimal amount of water for about 2 h. The plates containing thiourea-linked primer are then washed sequentially with 1% ammonium hydroxide, and water, followed by air drying at room temperature.

C. Immobilization via Hg-S Affinity Binding

An amino-modified oligonucleotide primer is prepared as described above. Conversion of the 5'-amino group to a thiol is carried out by reacting 5.0 $A_{260}$ units of the amine-containing primer dissolved in 1.0 ml of 0.2 molar 4-(2-hydroxyethyl)-1-piperazineethanesulfonic acid (pH 7.7) with 1.6 ml of 10 mM dithiobis(succinimidylpropionate) in dry acetonitrile for 1 h at 20° C. An additional 1.0 ml of 10 mM dithiobis(succinimidylpropionate) in acetonitrile is then added to the reaction vessel and the resulting mixture is stirred for an additional hour. Addition of dithioerythritol (3.5 ml of a 20 mM solution in 0.2 M Tris buffer) is followed by stirring for 1 h at 37° C. The thiol-derivatized primer solution is concentrated under vacuum to form a concentrate which is further purified using reverse phase HPLC followed by lyophilization.

In an alternate approach for synthesizing thiol-modified oligonucleotide primers, the 5'-phosphate of an oligonucleotide primer is esterified with 6-mercapto-hexanol using a β-cyanoethyl-phosphoramidite C6-Thiol-Modifier (Clontech Laboratories, Inc., Palo Alto, Calif.).

The thiol-derivatized primer is then immobilized on p-chloromercuribenzoate derivatized agarose by mixing a solution of the thiol-derivatized primer (0.25 $A_{260}$ units) dissolved in 140 $\mu$l of 1.0 M sodium chloride, 1.0 mM ethylenediaminetetraacetic acid disodium salt (EDTA), and 50 mM Tris HCl (pH 8) with 50 $\mu$l of p-chloromercuribenzoate derivatized agarose for 3 min at 20° C.

EXAMPLE 3

Selective Cleavage of a Synthetic DNA Probe Containing: Cleavable Ribose

A synthetic DNA probe containing a cleavable ribose site was selectively cleaved by ammonium hydroxide treatment. The 17-mer, having the sequence: 5'-AAA TAC ATC riboGCT TGA AC-3' (SEQ ID NO:10) was prepared to contain a cleavable ribose in the 7-position. The modified probe was treated with aqueous 3% ammonium hydroxide for 15 min at room temperature (pH 10) to effect selective cleavage of the ribose moiety.

EXAMPLE 4

Mass Spectral Analysis of the Selective Cleavage Products of a Ribose-Containing DNA Probe The cleavage products from Example 3 were analyzed using matrix assisted laser desorption with concomitant ionization (MALDI) in conjunction with time-of-flight (TOF) mass spectrometry.

The experimental apparatus used for analyzing the sample fragments was composed of an excitation source, a sample manipulator and a TOF mass spectrometer. The excitation sources used for desorption were a Nd:YAG laser (model DCR-1, Spectra-Physics, Mountain View, Calif.) with spatially filtered 5 ns pulses frequently tripled to 355 nm or quadrupled to 266 nm and a 35-ps pulse Nd:YAG laser (model PY610C-10, Continuum, Santa Clara, Calif.) operating at 355 nm. Both of the lasers were operated at a 10 Hz repetition rate, with a 5 nm pulse width. The desorption laser beam maintained at an incident angle of 45° was focused onto the sample with a 250 mm focal length quart lens to an elliptical spot size of approximately 100 by 150 $\mu$m. A Glan-laser polarizer (Newport Corporation, Fountain Valley, Calif.) was placed in a rotation stage in the beam path for continuously variable attenuation, allowing adjustment of the polarized Nd:YAG laser energy density from below 1 mJ/cm$^2$ to 100 MJ/cm$^2$. The optimum energy density for desorption was found to be in the range of 2 to 20 mJ/cm$^2$.

Sample preparation was carried out as follows. The oligonucleotide fragments were dissolved in deionized water at room temperature to concentrations of about 50 $\mu$mol/liter. A separate saturated solution of 3-hydroxypicolinic acid (3-HPA) in 50% water/acetonitrile was freshly prepared, and the two solutions were mixed to provide a sample solution containing 3-HPA and analyte in a molar ratio of about 10,000:1. A 2 $\mu$L aliquot of the sample solution was pipetted onto the sample stage and spread to an area of 2 mm diameter. The sample was dried under a gentle flow of nitrogen prior to insertion into the vacuum system.

The sample stage, consisting of either a smooth silver foil or a polished silicon wafer, was mounted on a manipulator which allows three translational and one rotational degrees of freedom. The studies were carried out at room temperature. The sample region was evacuated by a 300 liter per second turbomolecular pump. The drift and detection regions were evacuated using a cryopump with nominal 1500 liter per second pumping speed. The base pressure of the chamber was $3\times10^{-9}$ Torr, and the normal working pressure, within about five minutes of sample introduction, was $5\times10^{-8}$ Torr.

The ions produced during desorption were extracted perpendicular to the sample surface into the time-of-flight mass spectrometer by biasing the sample with a voltage of 28 kV, with the drift and extraction potentials at ground. The sample-extractor distance was 5 mm, and an einzel lens about 5 cm from the sample was used to focus the ions. Both linear and reflecting TOF mass spectrometric geometries were examined. For reflecting TOF-MS, a two stage electrostatic reflector was used and the effective drift path was 2.0 m. A dualmicrochannel plate detector was used. The detector was placed beside the electrostatic deflector due to space constraints of the vacuum chamber. Deflecting voltage was applied to horizontal deflecting plates and the beam path was bent in order to direct the ions to the detector for the linear geometry. The total flight distance was 1 m for the linear geometry. The four degree bend was sufficient to block the line-of-sight between the ion creation region and the detector to prevent any energetic neutral flux created in the ionization region from reaching the detector. For reflecting TOF measurements, the beam path was bent in the opposite direction. To avoid detector saturation caused by the high abundance of ionized matrix molecules in studies performed at higher laser powers, the low mass matrix ions were deflected away from the detector by a pulsed electric field of 200 V/cm.

The signal output of the microchannel plates was amplified and then digitized with a time resolution of 10 to 50 ns/channel and typically summed over 100 laser pulses. Mass calibration was performed by analyzing a variety of known masses, such as alkalis at low mass, isotopically resolved fullerenes, mixtures of gramicidin S, bovine insulin, horse heart cytochrome C, and horse heart myoglobin.

The resulting time-of-flight mass spectra are illustrated in FIG. 3A and FIG. 3B. FIG. 3A is a mass spectrum of the 17-mer synthetic mixed base primer containing a cleavable ribose linkage prior to ammonium hydroxide treatment. Two sizable peaks were observed for the intact 17-mer corresponding to the di-protonated molecular ion $[M+2H]^{2+}$ and the protonated molecular ion, $[M+H]^+$.

The resulting oligomer fragments obtained following ammonium hydroxide treatment were then analyzed, as shown in FIG. 3. As indicated in the mass spectrum, peaks corresponding to the expected cleavage products, the 7-mer, the 10-mer, and intact 17-mer, were readily observable (and identifiable).

EXAMPLE 5

Capture and Selective Cleavage of a Biotinylated Primer Having a Cleavable Ribose in the 10 Position A biotinylated 18-mer containing a ribose in the 10 position, 5'-biotin-ATCTTCCTG-ribo-GCAAACTCA-3', SEQ ID NO:11, (keystone Laboratories, Inc., Menlo Park, Calif.), was captured on streptavidin-coated beads (DynaBeads M-280, Dynal, Inc., Great Neck, N.Y.). The immobilized primer was then washed after surface binding, followed by treatment with ammonium hydroxide as described in Example 3 above to effect selective cleavage of the immobilized primer at the ribose site.

The modified primer, containing the biotin immobilization attachment site and the cleavable ribose site, was analyzed both prior to capture and subsequent to selective cleavage. The samples were analyzed using MALDI in conjunction with TOF mass spectrometry, as described in Example 4 above. FIG. 4 illustrates the mass spectrum of the 8-mer resulting from selective cleavage of the ribose site within the immobilized primer.

EXAMPLE 6

Immobilization of a Cleavable Extended Primer by Hybridization to an Intermediary Solid-Phase 1 Bound Oligonucleotide A modified M13 reverse primer containing a 5'-(S)-thymidine located 5 nucleotides from 35 the 3' end, having the sequence presented herein as SEQ ID NO:12, was hybridized to a single stranded target molecule (SEQ ID NO:14) in hybridization medium containing annealing buffer, 10X "THERMOSEQUENASE" Buffer (260 mM Tris-HCl, pH 9.5, 65 mM $MgCl_2$) (Amersham Life Sciences, Arlington Heights, Ill.). The annealing reaction was carried out by warming the above mixture to 65° C. for two minutes, and then allowing the mixture to cool slowly to room temperature over a period of about thirty minutes (Maniatis et al., 1982; Ausubel et al., 1989).

Following hybridization, the modified primer was extended using DNA polymerase ("THERMOSEQUENASE" DNA Polymerase) in the presence of a mixture of deoxynucleotides and dideoxynucleosides to produce a set of oligonucleotide fragments corresponding to the locations of adenine within the target (i.e. thymidine within the reaction product). The reaction was performed using standard cycle sequencing protocols and an 8:1 ratio of primer to template. Due to the primer-to-template ratio employed, the resulting set of primer extension products were primarily (89%) in single stranded form.

Following primer extension, an intermediary oligonucleotide complementary to the M13 reverse primer and biotinylated at the 3' end, having SEQ ID NO:13, was added to the mixture and annealed to the primer using a standard heat/cool annealing process: 95° C. for 2 min 30 sec; 25 cycles at 95° C. for 15 sec, 45° C. for 20 sec, 55° C. for 10 sec, 70° for 20 sec), 5 cycles at 95° C. for 30 sec, and 70° C. for 20 sec, followed by cooling from 95° C. to 70° C. for 1 min at the rate 0.1° C. per second, and subsequent maintenance of the sample at 4° C. Streptavidin coated magnetic beads (MPG-Steptavidin, CPG, Inc., Lincoln Park, N.J.) were then added to the mixture to capture the biotinylated intermediary oligonucleotide/extended primer hybrid. The immobilized product was washed to remove enzymes, triphosphates and salts in a multistep wash process. The sample was then treated with silver nitrate (5 µL, 0.02 mM, Aldrich, Milwaukee, Wis.) and DTT to release the extension segments into solution. This solution was (i) separated from the solid phase bound intermediary oligonucleotide-first primer region complex, (ii) mixed with 3-hydroxypicolinic acid, (iii) dried onto a silicon plate and (iv) analyzed by MALDI TOF. mass spectrometry as described in Example 4 above. The released extension segments are shown in FIG. 13.

As seen in FIG. 13, the method allows detection of oligonucleotide extension segments with read lengths up to at least about 33 base pairs with good resolution.

EXAMPLE 7

Detection of Point Mutation(s) Using a Single Base Fingerprint

Two DNA templates, one a synthetic 73-mer (presented herein as SEQ ID NO:14) with a sequence identical to wild-type M13 plasmid, corresponding to template "16-C/19-G", and the other a mutant plasmid, (having a partial sequence included herein as SEQ ID NO:15), referred to as template "16-A/19-T", were used in primer extension reactions. The sequences of the templates differed only at base positions 16 and 19, relative to the 3' end (counting upstream from the end of the priming region), with the first template possessing a cytosine at position 16 and a guanine at position 19, as presented in SEQ ID NO:14, while the second template, corresponding to SEQ ID NO:15, contained an adenine and a thymine substituted at positions 16 and 19, respectively.

Each of the templates was subjected to enzymatic extension in the presence of ddC using a primer with the sequence presented herein as SEQ ID NO:16. The resulting product mixtures, containing ddC-terminated oligonucleotide fragments derived from the parent templates, were then analyzed by MALDI TOF mass spectrometry as described above and illustrated in FIG. 14A (corresponding to the reaction product(s) derived from template 16-C/19-G, SEQ ID NO:17) and FIG. 14B (corresponding to the reaction product(s) derived from template 16-A/19-T, SEQ ID NO:18).

As can be seen from the resulting spectra of the reaction products, the exact mass values corresponding to the differences between select peaks in each of the spectra were calculated, confirming the presence of two single nucleotide substitutions at positions 16 and 19 from the 5' end. As demonstrated in FIG. 14A–14B, the measured mass values for the peak-to-peak differences are shown in large type, while the actual/theoretical mass values are shown in small type. The G-to-T base substitution is indicated by the difference in the $\Delta m$ values for template 16-C/19-G (mass peak b–mass peak a=618.9) versus template 16-A/19-T (mass peak b–mass peak a=593). The observed mass difference of 25 (618.9 minus 593.4) corresponds to the difference in mass between guanine (MW=51) and thymine (MW=126). Confirmation of a single base substitution occurring at position 19 as a result of a C to A mutation was similarly determined (e.g., $\Delta m_{d-b}$ versus $\Delta m_{g-f}$). The single base substitution at position 19 was further confirmed by the absence of a peak at position 19 in the spectrum corresponding to template 16-A/19-T (FIG. 14B).

EXAMPLE 8

Comparison of Primer Extension Reactions Using Cleavable Versus Full Primer A modified M13 reverse primer containing a 5'-biotin group and a thiol-thymidine located 5 nucleotides from the 3' end of the primer (SEQ ID NO:16) was hybridized to a single stranded target molecule (SEQ ID NO:14), followed by enzymatic extension in the presence of a mixture of deoxynucleotides and dideoxy-T to produce a set of oligonucleotide fragments corresponding to the locations of adenine within the target, following the procedure described in Example 6. Following the ddT extension reaction, the biotinylated primer/extension product was captured (immobilized) on streptavidin-coated magnetic beads. The bead-immobilized primer/extension products were then subjected to a series of wash steps to remove template, enzyme, triphosphates and additional salts. The streptavidin-coated magnetic beads, now containing immobilized primer/extension products, were then divided into two tubes. The contents of the first tube was treated with silver nitrate and DTT, to cleave the primer at the thiol-thymidine located 5 nucleotides from the 5'-end of the primer and to release the extension segments into solution. The contents of the second tube were boiled to effect disruption of the biotin/streptavidin bond and release the full primer/extension products into solution. The two samples were then separately mixed with 3-hydroxypicolinic acid, dried, and analyzed by MALDI TOF mass spectrometry as described above.

The resulting mass spectra are shown in FIG. 15A (full length primer-extension segments) and FIG. 15B (cleaved primer-extension segments having increased read length). As can be seen, the resolution quality and read length of spectra of cleaved primer-extension segment samples (FIG. 15B) according to the present method are superior to those of the full primer-boil/release sample (FIG. 15A). The broad peak centered around base No. 15 in the uncleaved primer sample (FIG. 15A) is due to primer dimerization, and is an artifact that occasionally occurs when the sample includes a large amount of primer. Cleavage of the primer removes this artifact, as can be seen in FIG. 15B.

While the invention has been described with reference to specific methods and embodiments, it will be appreciated that various modifications and changes may be made without departing from the invention.

REFERENCES

The following references, to the extent that they provide exemplary procedural or other details supplementary to those set forth herein, are specifically incorporated herein by reference.

Agrawal and Goodchild, *Tetrahedron Lett.*, 28:3539–3542, 1987.
Ausubel et al., In: Current Protocols in Molecular Biology, John Wiley and Sons, Inc., Media, PA, 1989.
Bannwarth et al, *DNA*, 5:413, 1986.
Bannwarth, *Chimia*, 41:302, 1987.
Bannwarth, *Helvetica Chimica Acta*, 71:1517–1527, 1988.
Bischoff et al., *Analytical Biochemistry*, 164:336–344, 1987.
Collins et al., *Science*, 225:72, 1984.
Cormier et al., *Nucl. Acids Res.*, 16:4583–4594, 1988.
Corey and Snider, *J. Am. Chem. Soc.*, 94:2549–2550, 1972.
Cosstick et al., *J. Chem. Soc., Chem. Comm.*, 992, 1988.
Cosstick et al., *Tetrahedron Lett.*, 30(35):4693–4696, 1989.
Daley et al., *Proc. Natl. Acad. Sci. USA*, 85:9312–9316, 1988.
Dattagupta, U.S. Pat. No. 4,818,681, 1989.
Erlich, In: PCR Technology, Stockton, New York, 1989.
Fodor et al., *Science*, 251:767–773, 1991.
Gale et al., *Proc. Natl. Acad Sci. USA*, 81:5648, 1984.
Ghosh et al., *Nucl. Acids Res.*, 15:5353–5372, 1987.
Gingeras et al., *Nucl. Acids Res.*, 15:5373–5390, 1987.
Glazer et al., *Nature*, 359:859–861, 1992.
Goldkorn et al., *Nucl. Acids Res.*, 14(22):9171–9191, 1986.
Green, In: Advances in Protein Chemistry, (Avidin, Ed.) Academic Press, New York, N.Y., p 29, 85–133, 1975.
Gromova, *Bioorg. Khim.*, 13:269, 1987.
Gyllensten, *BioTechniques*, 7:700, 1989.
Hasa et al., *Chem. Lett.*, 601, 1976.
Hegner et al., *FEBS Letters*, 336:452–456, 1993a.
Hegner et al., *Surface Sci.*, 291:39–46, 1993b.
Hillenkamp, *Adv. Mass Spectrometry*, 11A:354–361, 1988.
Hobbs, *Oranophosphorous Chem.*, 21:201–321, 1990.
Innis et al., In: PCR Protocols, Academic Press, San Diego, Calif., 1990.
Khrapko et al., *DNA Sequence*, 1:375–388, 1991.
Koole et al., *Proc. K Ned. Akad. Wet.*, B91:205–209, 1988.
Kremsky et al., *Nucl. Acids Res.*, 15:2891–2909, 1987.
Kusukawa et al., *BioTechniques*, 9:66, 1990.
Longo et al., *Gene*, 93:125, 1990.
Mag et al., *Nucl. Acids Res.*, 19(7):1437–1441, 1991.
Maniatis et al., In: Molecular Cloning: A Laboratory Manual, Cold Spring Harbor Laboratory, 1982.
Maskos et al., *Nuc. Acids Res.*, 20(7):1679–1684, 1992.
McBride et al., *Tetrahedron Lett.*, 24:245, 1983.
Miller et al., *J. Am. Chem. Soc.*, 93:6657–6665, 1971.
Moody et al., *Nucl. Acids Res.*, 12:4769–4782, 1989.
Mullis et al., U.S. Pat. No. 4,683,195, issued 28 Jul. 1987.
Mullis, U.S. Pat. No. 4,683,202, issued 28 Jul. 1987.
Nadjii et al., *J. Am. Chem. Soc.*, 114:9299–9269, 1992.
Nakamaye et al., *Nucl. Acids Res.*, 16:9947–9959, 1988.
Nelson et al., *Science*, 246:1585–1587, 1989.
Ogilvie et al., *Tetrahedron Lett.*, 26:4159–4162, 1986.

Olsen et al., *Methods Enzymol.,* 218:79–92, 1993.
Olsen et al., *Nucl. Acids Res.,* 20:2199, 1992.
Primings et al., *Methods Enzymol.,* 65:561–580, 1980.
Saha et al., *J. Org. Chem.,* 58:7827–7831, 1975.
Sanger et al., *J. Mol. Biol.,* 94:441–448, 1975.
Saiki et al., *Proc. Natl. Acad. Sci. USA,* 86:6230–6234, 1989.
Schmidt et al., *Methods Enzymol.,* 235:205–222, 1994.
Seliger et al., *Nucleosides Nucleotides,* 6:483–484, 1987.
Southern et al., *Genomics,* 13:1008–1017, 1992.
Sproat et al., Nucl. Acids Res., 15:4837, 1987.
Szczylik et al., *Science,* 253:562–565, 1991.
Szybalski, *Gene.,* 40:169–173, 19985.
Tomasz et al., *Tetrahedron Lett.,* 22:3905–3908, 1981.
Townsend et al., (Eds.), In: *Nucleic Acid Chemistry: Improved and New Synthetic Procedures, Methods and Techniques,* John Wiley and Sons, New York, N.Y., p 337, 1986.
Van Ness et al., *Nucl. Acids Res.,* 19:3345–3350, 1991.
Wu et al., *Rapid Comm. Mass Spectrometry,* 7:142–146, 1993.
Watson et al., In: *Recombinant DNA,* Second Edition, Scientific American, Inc., Chapter 27, 1992.
Yamamoto et al., *J. Chem. Soc.,* Perkin Trans. 11:306, 1980.
Youngquist et al., *Rapid Comm. Mass Spectrometry,* 8:77–81, 1994.
Zhang et al, *Nucl. Acids Res.,* 19:3929–3933, 1991.

What is claimed is:

1. A nucleic acid primer having a 5' end and a 3' end, comprising:
   (a) a first region containing the 5' end of the primer and an immobilization attachment site; and
   (b) a second region containing the 3' end of the primer including a free 3' hydroxyl and a selectively chemically cleavable site, wherein:

the 3' end is capable of being extended by an enzyme to generate an extension segment, whereby, when the primer is immobilized via the immobilization attachment site, and the selectively chemically cleavable site is cleaved, the remainder of the primer remains immobilized; and the selectively chemically cleavable site comprises a modified sugar or a chemically cleavable group incorporated into the phosphate backbone.

2. The primer of claim 1, wherein the selectively chemically cleavable site is located at or within about five nucleotides from the 3' end of the primer.

3. The primer of claim 2, wherein the second region of the primer comprises a single nucleotide.

4. The primer of claim 3, wherein the second region comprises a ribonucleotide.

5. The primer of claim 1, wherein the selectively chemically cleavable site comprises a chemically cleavable group incorporated into the phosphate backbone.

6. The primer of claim 1, wherein the selectively chemically cleavable site comprises a modified sugar.

7. The primer of claim 1, where the selectively chemically cleavable group is selected from the group consisting of dialkoxysilane, 3'-(S)-phosphorothioate, 5'-(S)-phosphorothioate, 3'-(N)-phosphoramidate, 5'-(N)-phosphoramidate, uracil, and ribose.

8. The primer of claim 7, wherein the selectively chemically cleavable group is 3'-(S)-phosphorothioate or 5'-(S)-phosphorothioate.

9. The primer of claim 1, wherein the enzyme is a DNA polymerase.

10. The primer of claim 1, wherein the enzyme is a ligase.

11. The primer of claim 1, further comprising a solid support attached to the immobilization attachment site.

12. The primer of claim 11, wherein the immobilization attachment site is attached to an intervening spacer arm bound to the solid support.

13. The primer of claim 12, wherein the intervening spacer arm is six or more atoms in length.

14. The primer of claim 11, wherein the solid support is selected from the group consisting of glass, silicon, polystyrene, aluminum, steel, iron, copper, nickel, silver and gold.

15. The primer of claim 11, wherein the solid support comprises a functionality selected from the group of avidin and streptavidin.

16. The primer of claim 11, wherein the solid support comprises an antibody.

17. The primer of claim 16, wherein the antibody comprises anti-digoxigenin.

18. The primer of claim 1, wherein the immobilization attachment site is a substituent on one of the bases or sugars of the primer.

19. The primer of claim 1, wherein the immobilization attachment site is biotin or digoxigenin.

20. The primer of claim 1, wherein the immobilization attachment site comprises a single-stranded nucleic acid.

21. The primer of claim 20, further comprising a solid support, wherein the single stranded nucleic acid is complementary to an intermediary oligonucleotide bound to the solid support and wherein the primer is attached to the solid support by hybridization of the immobilization attachment site to the intermediary oligonucleotide.

22. The primer of claim 5, wherein the chemically cleavable group incorporated into the phosphate backbone is selected from the group consisting of dialkoxysilane; β-cyano ether; 5'-deoxy-5'-aminocarbamate; 3'-deoxy-3'-aminocarbamate; urea; 2'-cyano-3',5'-phospho-diester; 3'-(S)-phosphorothioate; 5'-(S)-phosphorothioate; 3'-(N)-phosphoramidate; 5'-(N)-phosphoramidate; α-amino amide; vicinal diol; ribonucleoside; 2'-amino-3',5'-phosphodiester; allylic sulfoxide; ester; silyl ether; dithioacetal; 5'-thio-formal; α-hydroxy-methyl-phosphonic bisamide; acetal; and 3'-thio-formal.

* * * * *